(12) United States Patent
Vlahov et al.

(10) Patent No.: US 9,555,139 B2
(45) Date of Patent: Jan. 31, 2017

(54) BINDING LIGAND LINKED DRUG DELIVERY CONJUGATES OF TUBULYSINS

(75) Inventors: Iontcho Radoslavov Vlahov, West Lafayette, IN (US); Christopher Paul Leamon, West Lafayette, IN (US); Yu Wang, Fishers, IN (US)

(73) Assignee: Endocyte, Inc., West Lafayette, IN (US)

( * ) Notice: Subject to any disclaimer, the term of this patent is extended or adjusted under 35 U.S.C. 154(b) by 459 days.

(21) Appl. No.: 12/530,952

(22) PCT Filed: Mar. 13, 2008

(86) PCT No.: PCT/US2008/056824
§ 371 (c)(1),
(2), (4) Date: Sep. 11, 2009

(87) PCT Pub. No.: WO2008/112873
PCT Pub. Date: Sep. 18, 2008

(65) Prior Publication Data
US 2010/0048490 A1 Feb. 25, 2010

Related U.S. Application Data

(60) Provisional application No. 60/894,901, filed on Mar. 14, 2007, provisional application No. 60/911,551, filed on Apr. 13, 2007.

(51) Int. Cl.
*A61K 47/48* (2006.01)
*A61K 38/00* (2006.01)
*A61K 51/04* (2006.01)

(52) U.S. Cl.
CPC ......... *A61K 51/0497* (2013.01); *A61K 47/481* (2013.01); *A61K 47/48107* (2013.01); *A61K 47/48246* (2013.01)

(58) Field of Classification Search
CPC ............ A61K 47/481; A61K 47/48107; A61K 47/48246; A61K 51/0497
See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 3,632,622 A | 1/1972 | Moore et al. |
| 3,641,109 A | 2/1972 | Emerson et al. |
| 4,166,810 A | 9/1979 | Cullinan et al. |
| 4,203,898 A | 5/1980 | Cullinan et al. |
| 4,316,885 A | 2/1982 | Rakhit |
| 4,337,339 A | 6/1982 | Farina et al. |
| 4,639,456 A | 1/1987 | Trouet et al. |
| 4,650,803 A | 3/1987 | Stella et al. |
| 4,691,024 A | 9/1987 | Sirahata |
| 4,713,249 A | 12/1987 | Schroder |
| 4,801,688 A | 1/1989 | Laguzza et al. |
| 4,866,180 A | 9/1989 | Vyas et al. |
| 4,870,162 A | 9/1989 | Trouet et al. |
| 5,006,652 A | 4/1991 | Cullinan et al. |
| 5,094,849 A | 3/1992 | Cullinan et al. |
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,266,333 A | 11/1993 | Cady et al. |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,416,016 A | 5/1995 | Low et al. |
| 5,417,982 A | 5/1995 | Modi |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

Machine translation of WO2004005326, Jan. 15, 2004, pp. 1-5.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut~ons in Each Repeat, J. Mol. BIoL (2002) 324, 373-386.*
Definition of moiety, from http://dictionary.reference.com/browse/moiety, pp. 1-3. Accessed Aug. 26, 2010.*

(Continued)

*Primary Examiner* — Julie Ha
*Assistant Examiner* — Li Ni Komatsu
(74) *Attorney, Agent, or Firm* — Barnes & Thornburg LLP

(57) ABSTRACT

Described herein are compounds, pharmaceutical compositions and methods for treating pathogenic cell populations. The compounds described herein include conjugates of tubulysins and vitamin receptor binding ligands. The conjugates also include a releasable bivalent linker.

15 Claims, 7 Drawing Sheets

(56) References Cited

U.S. PATENT DOCUMENTS

| | | | |
|---|---|---|---|
| 5,463,048 A | 10/1995 | Skotnicki et al. |
| 5,491,231 A | 2/1996 | Nelson et al. |
| 5,547,668 A | 8/1996 | Kranz et al. |
| 5,552,545 A | 9/1996 | Pearce et al. |
| 5,562,907 A | 10/1996 | Arnon |
| 5,583,020 A | 12/1996 | Sullivan |
| 5,627,165 A | 5/1997 | Glazier |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden et al. |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,342,244 B1 | 1/2002 | Zalipsky et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Mulnar-Kimber et al. |
| 6,548,505 B1 | 4/2003 | Martin et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,279,562 B2 | 10/2007 | Molnar-Kimber et al. |
| 7,582,744 B2 | 9/2009 | Manoharan et al. |
| 7,601,332 B2 | 10/2009 | Vlahov et al. |
| 7,754,885 B2 * | 7/2010 | Hoefle et al. ............. 546/208 |
| 7,776,814 B2 | 8/2010 | Dömling et al. |
| 7,816,377 B2 | 10/2010 | Dömling et al. |
| 7,875,612 B2 | 1/2011 | Green et al. |
| 7,910,594 B2 | 3/2011 | Vlahov |
| 8,044,200 B2 | 10/2011 | Xu et al. |
| 8,105,568 B2 | 1/2012 | Vlahov |
| 8,288,557 B2 | 10/2012 | Vlahov et al. |
| 8,349,901 B2 | 1/2013 | Satyam |
| 8,383,122 B2 | 2/2013 | Dai et al. |
| 8,394,922 B2 | 3/2013 | Cheng et al. |
| 8,465,724 B2 | 6/2013 | Vlahov et al. |
| 8,470,822 B2 | 6/2013 | Green et al. |
| 8,476,451 B2 | 7/2013 | Ellman et al. |
| 8,497,365 B2 | 7/2013 | Davis et al. |
| 8,546,425 B2 | 10/2013 | Leamon et al. |
| 8,580,820 B2 | 11/2013 | Zanda et al. |
| 8,765,096 B2 | 7/2014 | Leamon et al. |
| 8,802,632 B2 | 8/2014 | Cheng et al. |
| 9,138,484 B2 | 9/2015 | Leamon |
| 9,192,682 B2 | 11/2015 | Vlahov |
| 2001/0031252 A1 | 10/2001 | Low et al. |
| 2002/0151088 A1 | 10/2002 | Molnar-Kimber et al. |
| 2003/0086900 A1 | 5/2003 | Low et al. |
| 2003/0162234 A1 | 8/2003 | Jallad |
| 2003/0194409 A1 | 10/2003 | Rothman et al. |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2004/0242582 A1 | 12/2004 | Green et al. |
| 2004/0247614 A1 | 12/2004 | Dorr et al. |
| 2005/0002942 A1 | 1/2005 | Vlahov et al. |
| 2005/0004010 A1 | 1/2005 | Collins et al. |
| 2005/0026068 A1 | 2/2005 | Gogolides et al. |
| 2005/0107325 A1 | 5/2005 | Mancharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2005/0249740 A1 | 11/2005 | Doemling |
| 2006/0019911 A1 | 1/2006 | Papisov |
| 2006/0058266 A1 | 3/2006 | Manoharan et al. |
| 2006/0105975 A1 | 5/2006 | Pendergrast et al. |
| 2006/0128754 A1 | 6/2006 | Hoefle et al. |
| 2006/0217360 A1 | 9/2006 | Hoefle et al. |
| 2006/0222653 A1 | 10/2006 | Abel et al. |
| 2007/0009434 A1 | 1/2007 | Low et al. |
| 2007/0134332 A1 | 6/2007 | Turnell et al. |
| 2007/0275904 A1 | 11/2007 | Vite |
| 2008/0096893 A1 | 4/2008 | Zebala |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2009/0247614 A1 | 10/2009 | Manoharan et al. |
| 2010/0004276 A1 | 1/2010 | Vlahov et al. |
| 2010/0040669 A1 | 2/2010 | Higuchi |
| 2010/0074863 A1 | 3/2010 | Or et al. |
| 2010/0104626 A1 | 4/2010 | Leamon |
| 2010/0129314 A1 | 5/2010 | Singh et al. |
| 2010/0144647 A1 | 6/2010 | Kratz et al. |
| 2010/0240701 A1 | 9/2010 | Vlahov |
| 2010/0323973 A1 | 12/2010 | Leamon |
| 2011/0027274 A1 | 2/2011 | Cheng et al. |
| 2011/0166319 A1 | 7/2011 | Dai et al. |
| 2011/0172254 A1 | 7/2011 | Leamon et al. |
| 2011/0245295 A1 | 10/2011 | Chai et al. |
| 2012/0022245 A1 | 1/2012 | Low |
| 2012/0065149 A1 | 3/2012 | Vlahov et al. |
| 2012/0129779 A1 | 5/2012 | Richter |
| 2012/0252738 A1 | 10/2012 | Richter |
| 2012/0252739 A1 | 10/2012 | Richter |
| 2012/0258905 A1 | 10/2012 | Leamon |
| 2012/0259100 A1 | 10/2012 | Jin |
| 2012/0322741 A1 | 12/2012 | Low et al. |
| 2013/0029900 A1 | 1/2013 | Widdison |
| 2013/0116195 A1 | 5/2013 | Leamon |
| 2013/0137139 A1 | 5/2013 | Vlahov et al. |
| 2013/0158271 A1 | 6/2013 | Vlahov |
| 2013/0184435 A1 | 7/2013 | Vlahov |
| 2013/0203680 A1 | 8/2013 | Leamon |
| 2013/0217638 A1 | 8/2013 | Wessjohann et al. |
| 2013/0224228 A1 | 8/2013 | Jackson et al. |
| 2013/0281678 A1 | 10/2013 | Dai et al. |
| 2014/0058063 A1 | 2/2014 | Vlahov |
| 2014/0058064 A1 | 2/2014 | Vlahov |
| 2014/0066594 A1 | 3/2014 | Vlahov |
| 2014/0073761 A1 | 3/2014 | Leamon |
| 2014/0073763 A1 | 3/2014 | Low et al. |
| 2014/0080175 A1 | 3/2014 | Vlahov |
| 2014/0107316 A1 | 4/2014 | Vlahov |
| 2014/0193437 A1 | 7/2014 | Lin et al. |
| 2014/0227295 A1 | 8/2014 | Cong et al. |

(56) References Cited

U.S. PATENT DOCUMENTS

| | | |
|---|---|---|
| 2014/0227298 A1 | 8/2014 | Cong et al. |
| 2014/0249315 A1 | 9/2014 | Vlahov |
| 2014/0309406 A1 | 10/2014 | Li et al. |
| 2014/0323690 A1 | 10/2014 | Cheng et al. |
| 2015/0258203 A1 | 9/2015 | Vlahov et al. |
| 2015/0314015 A1 | 11/2015 | Leamon et al. |
| 2016/0002167 A1 | 1/2016 | Vlahov et al. |
| 2016/0168183 A1 | 6/2016 | Leamon et al. |

FOREIGN PATENT DOCUMENTS

| | | |
|---|---|---|
| EP | 0 116 208 A1 | 8/1984 |
| EP | 0 163 550 A2 | 12/1985 |
| EP | 0 247 792 | 12/1987 |
| EP | 0116208 | 3/1988 |
| EP | 0 280 741 A1 | 9/1988 |
| EP | 0 354 728 | 2/1990 |
| IL | 93983 | 2/1997 |
| WO | WO/85/05554 | 12/1985 |
| WO | WO 88/01622 | 3/1988 |
| WO | WO 90/12095 | 10/1990 |
| WO | WO 90/12096 | 10/1990 |
| WO | WO91/07418 | 5/1991 |
| WO | WO95/15335 | 6/1995 |
| WO | WO96/36367 | 11/1996 |
| WO | WO 98/08382 | 3/1998 |
| WO | WO 98/08859 | 3/1998 |
| WO | WO 98/10651 A1 | 3/1998 |
| WO | WO 99/20626 A1 | 4/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO01/13957 | 3/2001 |
| WO | WO 01/28592 | 4/2001 |
| WO | WO 01/74382 | 10/2001 |
| WO | WO02/059272 | 8/2002 |
| WO | WO02/085908 | 10/2002 |
| WO | WO 02/087424 | 11/2002 |
| WO | WO 02/098868 | 12/2002 |
| WO | WO03/050295 | 6/2003 |
| WO | WO03/092742 | 11/2003 |
| WO | WO 03/097647 | 11/2003 |
| WO | WO2004/005326 | 1/2004 |
| WO | WO2004/005327 | 1/2004 |
| WO | WO 2004/012735 | 2/2004 |
| WO | WO/2004/022099 | 3/2004 |
| WO | WO/2004/037210 | 5/2004 |
| WO | WO2004/046170 | 6/2004 |
| WO | WO 2004/054622 | 7/2004 |
| WO | WO 2004/069159 | 8/2004 |
| WO | WO2004/100983 | 11/2004 |
| WO | WO 2005/074901 | 8/2005 |
| WO | WO2005/112919 | 12/2005 |
| WO | WO2005/115912 | 12/2005 |
| WO | WO 2006/012527 | 2/2006 |
| WO | WO 2006/042146 | 4/2006 |
| WO | WO/2006/089007 | 8/2006 |
| WO | WO 2006/101845 | 9/2006 |
| WO | WO2006/105141 | 10/2006 |
| WO | WO2007/002222 | 1/2007 |
| WO | WO 2007/022493 | 2/2007 |
| WO | WO2007/022494 | 2/2007 |
| WO | WO2007/022512 | 2/2007 |
| WO | WO2007/140298 | 12/2007 |
| WO | WO2008/057437 | 5/2008 |
| WO | WO 2008/101231 | 8/2008 |
| WO | WO 2008/112873 | 9/2008 |
| WO | WO2009/002993 | 12/2008 |
| WO | WO2009/055562 | 4/2009 |
| WO | WO 2010/045598 | 4/2010 |
| WO | WO 2010/033733 | 5/2010 |
| WO | WO 2011/069116 | 6/2011 |
| WO | WO2011/106639 | 9/2011 |
| WO | WO 2011/130598 | 10/2011 |
| WO | WO2012/019123 | 2/2012 |
| WO | WO 2012/047525 | 4/2012 |
| WO | WO 2012/090104 | 7/2012 |
| WO | WO 2013/126797 | 8/2013 |
| WO | WO 2013/130776 | 9/2013 |
| WO | WO 2013/149185 | 10/2013 |
| WO | WO 2013/170272 | 11/2013 |
| WO | WO 2013/173392 | 11/2013 |
| WO | WO 2013/173393 | 11/2013 |
| WO | WO 2014/009774 | 1/2014 |
| WO | WO 2014/040752 | 3/2014 |
| WO | WO 2014/062697 | 4/2014 |
| WO | WO 2014/078484 | 5/2014 |
| WO | WO 2014/080251 | 5/2014 |
| WO | WO2015/106599 | 7/2015 |

OTHER PUBLICATIONS

Muller, Prodrug Approaches for Enhancing the Bioavailability of Drugs eith Low Solubility, Chemistry & Biodiversity, 2009, 6, pp. 2071-2083.*

Beaumont, et, al, Design of Ester Prodrugs to Enhance Oral Absorption of Poorly Permeable Compounds: Challenges to the Discovery Scientist, Current Drug Metabolism, 2003, 4, 461-485.*

Hyo-Kyung Han, Targeted Prodrug Design to Optimize Drug Delivery, AAPS Pharmsci 2000; 2 (1) article 6 pp. 1-11.*

Yashveer Singh et al, Recent Trends in Targeted Anticancer Prodrug and Conjugate Design, Curr Med Chem. 2008 ; 15(18): 1802-1826.*

Testa B., Prodrug Research: Futile or Fertile?, Biochem. Pharm., 2004, 68, pp. 2097-2106.*

Ettmayer, P. et al, Lessons Learned from Marketed and Investigational Prodrugs,J. Med. Chem., 2004, 47 (10), pp. 2393-2404.*

Defination of derivative and analog, from http://cancerweb.ncl.ac.uk/cgi-bin/omd?query=derivative and http://cancerweb.ncl.ac.uk/cgi-bin/omd?query=analog, pp. 1-5, accessed Jul. 7, 2005.*

Chae et al, Recombinant Expression, Isotope Labeling and Purification of the Vitamin D Receptor Binding Peptide, Bull. Korean Chem. Soc. 2011, 32, pp. 4337-4340.*

Water, from http://www.biology-online.org/dictionary/Water, pp. 1-3, accessed Apr. 24, 2014.*

NIOSH List of Antineoplastic and Other Hazardous Drugs in Healthcare Settings 2010, pp. 1-16, published Sep. 2010.*

De Vita, V. T., et al., "*Biologic Therapy of Cancer*", 1995, 2d ed. J. B. Lippincott Company Philadelphia.

Domling, Alexander, et al., "Myxobacterial Epothilones and Tubulysins as Promising Anticancer Agents", 2005, *Molecular Diversity*, No. 9, pp. 141-147.

Hofle, G., et al., "Semisynthesis and Degradation of the Tubulin Inhibitors Epothilone and Tubulysin", 2003, *Pure Appl. Chem.*, vol. 75, Nos. 2-3, pp. 167-178.

Lee, Francis Y. F., et al., "BMS-247550: A Novel Epothilone Analog With a Mode of Action Similar to Paclitaxel But Possessing Superior Antitumor Efficacy", 2001, *Clin Cancer Res*, No. 7, pp. 1429-1437.

Melby, E.L., et al., "Entry of Protein Toxins in Polarized Epithelial Cells", 1993, *Cancer Res.*, No. 53, vol. 8, pp. 1755-1760.

Olsnes, S., et al., Immunotoxins-Entry into Cells and Mechanisms of Action, 1989, *Immunol. Today*, No. 10, pp. 291-295.

Peltier, Hillary M., et al., "The Total Synthesis of Tubulysin D," 2006, *J. Am. Chem. Soc.* No. 128, pp. 16018-16019.

Raghavan, Bhooma, et al., "Cytotoxic Simplified Tubulysin Analogues", Mar. 4, 2008, *J. Med.. Chem. Soc*, 10.1021/jm701321p; pp. A-D.

Rose, William C., "Taxol-Based Combination Chemotherapy and Other In Vivo Preclinical Antitumor Studies", 1993, *J Nail Cancer Inst Monogr*, No. 15, pp. 47-53.

Sasse, Florenz, et al., "Tubulysins, New Cytostatic Peptides from Myxobacteria Acting on Microtubuli Production, Isolation, Physico-Chemical and Biological Properties", Sep. 2000, *The Journal of Antibiotics*, vol. 53, No. 9, pp. 879-885.

Steinmetz, Heinrich, et al., "Isolation, Crystal and Solution Structure Determination, and Biosynthesis of Tubulysins—Powerful

(56) References Cited

OTHER PUBLICATIONS

Inhibitors of Tubulin Polymerization from Microbacteria", 2004, *Agnew. Chem. Int. Ed.* No. 43, pp. 4888-4892.
Westerhof, G. R., et al. "Carrier- and Receptor-Mediated Transport of Folate Antagonists Trageting Folate-Dependent Enzymes: Correlates of Molecular-Structure and Biological Activity", 1995, *Mol. Pharm.* No. 48, pp. 459-471.
Agoston E.S. et al., "Vitamin D Analogs as Anti-Carcinogenic Agents," *Anti-Cancer Agents in Medicinal Chemistry*, 2006; 6(1): 53-71.
Anderson et al., "Potocytosis: Sequestration and transport of small molecules by caveolae," *Science*, 1992; 255: 410-411.
Antony A.C., "Folate receptors," *Annu Rev Nutr*, 1996; 16: 501-21.
Antony A.C., "The biological chemistry of folate receptors," *Blood*, 1992; 79(11):2807-2820.
Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.
Archer M.C. et al., "Separation of Folic Acid Derivatives and Pterins by High-Performance Liquid Chromatography," *Methods in Enzymology*, 1980; 66: pp: 452-459.
Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.
Ayers W.A., "Effect of Vitamin B12 and Analogs on the Respiration of a Marine Bacterium," *Archives of Biochemistry and Biophysics*, 1962, vol. 96, pp. 210-215.
Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).
Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.
Bavetsias, V., et al., "The design and synthesis of water-soluble analogues of CB30865, a quinazolin-4-one-based antitumor agent," J Med Chem, 2002; 45(17): 3692-3702.
Birinberg E. M. et al., "Synthesis and antimetabolic activity of pyrimidine analogs of folic and pteroic acids," *Pharmaceutical Chemistry Journal*, 1969; 3(6): pp. 331-333.
Bock et al., "Sulfonamide structure-activity relationships in a cell-free system. 2. Proof for the formation of a sulfonamide-containing folate analog," *Journal of Medical Chemistry*, 17: 23-28 (1974).
Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.
Campbell et al., "Folate-binding protein is a marker for ovarian cancer," *Cancer Res.*, 1991; 51: 5329-5338.
Cho et al., "Single-chain Fv/folate conjugates mediate efficient lysis of folate-receptor-positive tumor cells," *Bioconjug. Chem.* 8(3): 338-346 (1997).
Christensen et al., "Membrane receptors for endocytosis in the renal proximal tubule," *Int. Rev. Cytol.*, 1998; 180: 237-284.
Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.
Citro G. et al., "Inhibition of leukemia cell proliferation by folic acid-polylysine-mediated introduction of c-*myb* antisense oligodeoxynucelotides into HL-60 cells," *Br. J. Cancer*, 1994; 69: 463-467.
Cope A.C. et al., "Thermal Rearrangement of Allyl-type Sulfoxides, Sulfones and Sulfinates," *J. Am. Chem. Soc.*, 1950; 72; 59-67.
Cosulich D.B. et al., "Analogs of Pteroylglutamic Acid. I. N10-Alkylpteroic Acid and Derivatives," *JACS*, 1948, 70 (5), pp. 1922-1926.

Douglas J.T. et al., "Targeted Gene Delivery by Tropism-Modified Adenoviral Vectors," *Nat. Biotechnol.*, 1996, vol. 14, pp. 1574-1578.
Eichman, J.D. et al., "The Use of PAMAM Dendrimers in the Efficient Transfer of Genetic Material Into Cells", Jul. 2000, PSTT, vol. 3, No. 7, pp. 232-245.
Foong, L.Y. et al., "Development of a Novel Thiol Reagent for Probing Ion Channel Structure: Studies in a Model System," Biochemistry, 1997, vol. 36, pp. 1343-1348.
U.S. Appl. No. 60/946,092, filed Jun. 25, 2007, Vlahov et al.
U.S. Appl. No. 60/982,595, filed Oct. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.
Frankel AE., "Immunotoxin therapy of cancer," *Oncology*, 1993; 7(5): 69-78.
Shealy Y.F., "Synthesis and Evaluation of Some New Retinoids for Cancer Chemoprevention," *Preventive Medicine*, 1989, vol. 18, pp. 624-645.
Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.
Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).
GE Healthcare, Instructions 71/7104-00 AD.
Gibbs, DD et al., "BGC 945, a novel tumor-selective thymidylate synthase inhibitor targeted to alpha-folate receptor-overexpressing tumors," Cancer Res, 2005; 65(24): 11721-11728.
Gottschalk S. et al., "Folate receptor mediated DNA delivery into tumor cells: potosomal disruption results in enhanced gene expression," *Gene Therapy*, 1994; 1(3): 185-191.
Greene T.E. et al., "Protective Groups in Organic Synthesis," 2d edition, John Wiley & Sons, Inc. New York (1991).
U.S. Appl. No. 12/739,579, filed Apr. 23, 2010, Vlahov et al.
U.S. Appl. No. 12/775,824, filed May 7, 2010, Green et al.
Hanck A.B. et al., "Dexpanthenol (Ro 01-4709) in the treatment of constipation," *Acta Vitaminol Enzymol*, 1982; vol. 4 (1-2), pp. 87-97 (abstract only).
Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.
Henderson, E.A. et al., Targeting the alpha-folate receptor with cyclopenta[g]quinazoline-based inhibitors of thymidylate synthase, Bioorg Med Chem, 2006; 14(14): 5020-5042.
Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.
Hofland et al., "Folate-targeted gene transfer in vivo," *Mol Ther* 5(6): 739-744 (2002).
Holladay et al., "Riboflavin-mediated delivery of a macromolecule into cultured human cells," *Biochim Biophys Acta*, 1426(1): 195-204 (1999).
Holm, J. et al., "Folate receptors in malignant and benign tissues of human female genital tract," *BioSci. Rep.*, 17(4): 415-427 (1997).
Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).
U.S. Appl. No. 12/666,712, filed Dec. 24, 2009, Leamon et al.
Hosomi A. et al., "Affinity for a-tocopherol transfer protein as a determinant of the biological activities of vitamin E analogs," *Federation of European Biochemical Societies Letters*, 1997, vol. 409, pp. 105-108.
Houlihan, C. M. et al., "Preparation and Purification of Pteroic Acid from Folic Acid," *Analytical Biochemistry*, 1972, vol. 46, pp. 1-6.
Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," Adv Drug Deliv Rev, 2004; 56(8): 1111-1125.

(56) References Cited

OTHER PUBLICATIONS

Jones T.R. et al., "A potent antitumour quinazoline inhibitor of thymidylate synthetase: synthesis, biological properties and therapeutic results in mice," *Eur J Cancer*, 1981; 17(1):11-9.
Jones T.R. et al., "Quinazoline antifolates inhibiting thymidylate synthase: variation of the amino acid," *J Med Chem*, 1986; 29(6):1114-8.
Jung K.H. et al., "Intramolecular o-glycoside bond formation," *Chem. Rev.*, 2000, 100, 4423-42.
Kagechika H et al., "Synthetic Retinoids: Recent Developments Concerning Structure and Clinical Utility," *Journal of Medicinal Chemistry*, 2005; vol. 48, No. 19, pp. 5875-5883.
Kamen et al., "Delivery of folates to the cytoplasm fo MA104 cells is mediated by a surface receptor that recycles," *J. Biol. Chem.*, 263: 13602-13609 (1988).
Kamen et al., "The folate receptor works in tandem with a probenecid-sensitive carrier MA104 cells in vitro," *J. Clin. Invest.*, 87(4): 1442-1449 (1991).
Kamen, B. A. et al., "Receptor-mediated folate accumulation is regulated by the cellular folate content," *Proc. Natl. Acad. Sci. USA*, 83: 5983-5987 (1986).
Kandiko C.T. et al., "Inhibition of Rat Brain Pyruvate Dehydrogenase by Thiamine Analogs," *Biochemical Pharmacology*, 1988; vol. 37, No. 22, pp. 4375-4380.
Kane et al., "The influence of extracellular folate concentration on methotrexate uptake by human KB cells. Partial characterization of a membrane-associated methotrexate binding protein," *J. Biol. Chem.*, 261: 44-49 (1986).
Kim et al., "Synthesis and biological activity of 10-thia-10-deaza analogs of folic acid, pteroic acid, and related compounds", *Journal of Medical Chemistry*, 18: 776-780 (1975).
Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.
Kumar H.P. et al., "Folate transport in Lactobacillus salivarius. Characterization of the transport mechanism and purification and properties of the binding component," *J. Biol. Chem..* 1987; 262(15):7171-7179.
Ladino et al., "Folate-maytansinoids: target-selective drugs of low molecular weight," *Int. J. Cancer*, 73(6): 859 864 (1997).
Lambooy J. P., "Riboflavin Analogs Utilized for Metabolism by a Lactobacillus Casei Mutant," Int. J. Biochem., vol. 16, No. 2, 1984, pp. 231-234.
Landuer W. et al., "The Interaction in Teratogenic Activity of the Two Niacin Analogs 3-acetylpyridine and 6-aminonicotinamide," *J Exp Zool*, 151(3):253-258 (1962).
Langone, J.J., et al., "Radioimmunoassays for the Vinca Alkaloids, Vinblastine and Vincristine", 1979, *Analytical Biochemistry*, No. 95, pp. 214-221.
Larock R.C., "Comprehensive Organic Transformations, a guide to functional group preparations," VCH Publishers, Inc. New York (1989).
Leamon CP et al, "Cytotoxicity of folate-Pseudomonas exotoxin conjugates toward tumor cells. Contribution of translocation domain," *J. Biol. Chem.* 268(33): 24847-24854 (1993).
Leamon CP et al., "Comparative Preclinical Activity of the Folate-targeted Vinca Alkaloid Conjugates EC140 and EC145," *Int J Cancer*, 2007; 121(7):1585-92.
Leamon CP et al., "Cytotoxicity of momordin-folate conjugates in cultured human cells," *J. Biol. Chem.*, 1992; 267(35): 24966-24971.
Leamon CP et al., "Delivery of macromolecules into living cells: a method that exploits folate receptor endocytosis," *Proc. Natl. Acad. Sci. USA* 88(13): 5572-5573 (1991).
Leamon CP et al., "Folate-mediated targeting: from diagnostics to drug and gene delivery," *Drug Discovery Today* 6: 36-43 (2001).
Leamon CP et al., "Folate-targeted chemotherapy," *Adv Drug Deliv Rev*, 2004;56(8): 1127-41.
Leamon CP et al., "Membrane folate-binding proteins are responsible for folate-protein conjugate endocytosis into cultured cells," *Biochem. J.* 291: 855-860 (1993).

Leamon CP et al., "Selective targeting of malignant cells with cytotoxin-folate conjugates," *J. Drug Target.* 2(2): 101-112 (1994).
Leamon CP et al., "Synthesis and biological evaluation of EC140: A novel folate-targeted vinca alkaloid conjugate," *Bioconjug Chem*, 2006;17(5):1226-32.
Leamon CP et al., "Synthesis and Biological Evaluation of EC20: A New Folate-Derived, (99m)TC-Based Radiopharmaceutical," *Bioconjug. Chem.* 13(6): 1200-1210 (2002).
Leamon CP et al., "Synthesis and biological evaluation of EC72: a new folate-targeted chemotherapeutic," *Bioconjug Chem.*, 2005;16(4):803-11.
Leamon et al., "Folate-mediated drug delivery: effect of alternative conjugation chemistry," *J. Drug Target* 7(3): 157-169 (1999).
Lee et al, "Measurement of Endosome pH Following Folate Receptor-Mediated Endocytosis," *Biochim. Biophys. Acta* 1312(3): 237-242 (1996).
Lee W.W. et al., "Folic acid antagonists. Methotrexate analogs containing spurious amino acids. Dichlorohomofolic acid," *Journal of Medical Chemistry*, 17: 326-330 (1974).
Lee et al., "Synthesis and evaluation of taxol-folic acid conjugates as targeted antineoplastics," *Bioorg Med Chem*. 10(7): 2397-2414, (2002).
Lee, R. J. and Huang, L., "Folate-Targeted, Anionic Liposome-Entrapped Polylysine-Condensed DNA for Tumor Cell-Specific Gene Transfer," *J. Biol. Chem.* 271(14): 8481-8487 (1996).
Lee, R. J. and Low, P. S, "Delivery of liposomes into cultured KB cells via folate receptor-mediated endocytosis," *J. Biol. Chem.* 269(5): 3198-3204 (1994).
Lee, R. J. and Low, P. S., "Folate-mediated tumor cell targeting of liposome-entrapped doxorubicin in vitro," *Biochim. Biophys. Acta* 1233: 134-144 (1995).
Lemon, Julia, et al., "Conversion of Pterolyglutamic Acid to Pteroic Acid by Bacterial Degradation," *Archives of Biochemistry*, 1948; vol. 19, pp. 311-316.
Levy, Carl C., et al. "The Enzymatic Hydrolysis of Methotrexate and Folic Acid", 1967, *The Journal of Biological Chemistry*, vol. 242, No. 12, pp. 2933-2938.
Lewis et al., "Receptor-mediated folate uptake is positively regulated by disruption of actin cytoskeleton," *Cancer Res.* 58(14): 2952-2956 (1998).
Li et al, "Targeted delivery of antisense oligodeoxynucleotides by LPDII," *J. Liposome Res.* 7(1): 63 (1997).
Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).
Lonsdale D, "A Review of the Biochemistry, Metabolism and Clinical Benefits of Thiamin(e) and its Derivatives," publication, Advance Access Publication, vol. 3, Feb. 2006, pp. 49-59.
Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).
Low P.S. et al., "Folate Receptor-Targeted Drugs for Cancer and Inflammatory Diseases," *Adv Drug Deliv Rev*, 2004;56(8):1055-238.
Lu et al., "Folate-targeted enzyme prodrug cancer therapy utilizing penicillin-V amidase and a doxorubicin prodrug," *J. Drug Target*, 7(1): 43-53 (1999).
Lu, J. Y. and Low, P. S., "Folate targeting of haptens to cancer cell surfaces mediates immunotherapy of syngeneic murine tumors," *Cancer Immunol Immunother*, 51: 153-162 (2002).
Lu, J. Y. and Low, P. S., "Folate-mediated delivery of macromolecular anticancer therapeutic agents," *Adv. Drug Del Rev*, 2002; 54(5): 675-693.
Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).
Mack D.O. et al., "The Carboxylation Activity of Vitamin K Analogs with Substitutions at Position 2, 3, or 5," *Journal of Biological Chemistry*, 1979; vol. 254, pp. 2656-2664.
Mancuso A.J. et al., "Activated Dimethyl Sulfoxide: Useful Reagents for Synthesis," *Synthesis*, 1981, pp. 165-184.

(56) References Cited

OTHER PUBLICATIONS

March, Advanced Organic Chemistry, 1992, John Wiley & Sons, 4th Ed., pp. 362-363, 816, 885, 896.
Mathais et al., "Receptor-mediated targeting of 67Ga-deferoxamine-folate to folate-receptor-positive human KB tumor xenografts," *Nucl Med Biol*, 26(1): 23-25 (1999).
Mathais et al., "Synthesis of [(99m)Tc]DTPA-folate and its evaluation as a folate-receptor-targeted radiopharmaceutical," *Bioconjug Chem*, 11(2): 253-257 (2000).
Mathias et al., "Indium-111-DTPA-Folate as a potential folate-receptor-targeted radiopharmaceutical," *J. Nucl. Med.*, 39(9): 1579-1585 (1998).
Mathias et al., "Tumor-Selective Radiopharmaceutical Targeting via Receptor-Mediated Endocytosis of Gallium-67-Deferoxamine-Folate," *J. Nucl. Med*, 37(6): 1003-1008 (1996).
Mathias, C. J., "A kit formulation for preparation of [(111)In]In-DTPA-folate, a folate-receptor-targeted radiopharmaceutical," *Nucl. Med. Biol.*, 25(6): 585-587 (1998).
Matsui et al., "Studies on mitomycins. III. The synthesis and properties of mitomycin derivatives," *J Antibiot*, 21: 189-198 (1968).
Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.
McAlinden TP et al., "Synthesis and Biological Evaluation of a Fluorescent Analogue of Folic Acid," *Biochemistry*, 1991; 30: 5674-81.
McHugh M et al., "Demonstration of a High Affinity Folate Binder in Human Cell Membranes and its Characterization in Cultured Human KB Cells," *J Biol Chem*, 1979; 254(22):11312-8.
Melani et al., "Targeting of interleukin 2 to human ovarian carcinoma by fusion with a single-chain Fv of antifolate receptor antibody," *Cancer Res.* 58(18): 4146-4154 (1998).
Mislick et al., "Transfection of folate-polylysine DNA complexes: evidence for lysosomal delivery," *Bioconjug. Chem.*, 6(5): 512-515 (1995).
Mock D.M. et al., "Urinary Biotin Analogs Increase in Humans Dining Chronic Supplementation: the Analogs are Biotin Metabolites," *Am J Physiol Endocrinol Metab*, 1997; 272: E83-E85.
Morshed et al., "Folate transport proteins mediate the bidirectional transport of 5-methyltetrahydrofolate in cultured human proximal tubule cells," *J. Nutr.*, 127(6): 1137-1147 (1997).
Nair et al., "Folate analogs altered in the C9-N10 bridge region. 14. 11-Oxahomofolic acid, a potential antitumor agent", *Journal of Medical Chemistry*, 23: 59-65 (1980).
Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).
Nair et al., "Palate analogs altered in the C9-N10 bridge region: N10-tosylisohomofolic acid and N10-tosylisohomoaminopterin," *Journal of Medical Chemistry*, 21: 673-677 (1978).
Nair et al., "Folate analogs altered in the C9-N10 bridge region: 11-thiohomofolic acid," *Journal of Medical Chemistry*, 22: 850-855 (1979).
Nair et al., "Palate analogs. 20. Synthesis and antifolate activity of 1',2',3',4',5',6'-hexahydrohomofolic acid," *Journal of Medical Chemistry*, 26: 135-140 (1983).
Nair et al., "Palate analogs. 21. Synthesis and antifolate and antitumor activities of N10-(cyanomethyl)-5,8-dideazafolic acid," *Journal of Medical Chemistry*, 26: 605-607 (1983).
Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).
Nair et al., "Folate analogues altered in the C9-N10 bridge region. 10-Oxafolic acid and 10-oxaaminopterin," *Journal of Medical Chemistry*, 19: 825-829 (1976).

Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," *Tetrahedron Letters*, No. 7, pp. 783-787 (1968).
Neuzil J. et al., "Vitamin E Analogs: A New Class of Multiple Action Agents with Anti-Neoplastic and Anti-Atherogenic Activity," *Apoptosis*, 2002; vol. 7, pp. 179-187.
Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.
Nimmo-Smirth R.H. et al., "Some Effects of 2-deaminopteroylglutamic Acid upon Bacterial Growth," *J. Gen. Microbial.*, 1953; 9: 536-544.
Nishikawa, Yuji et al., "Growth Inhibition of Hepatoma Cells Induced by Vitamin K and its Analogs," *Journal of Biological Chemistry*, 1995; vol. 270, No. 47, pp. 28304-28310.
Nomura, Makoto et al., "Development of an Efficient Intermediate a[2-(Trimethylsilyl)ethoxy]-2-N-[2-(trimethylsilyl)ethoxycarbonyl]folic Acid, for the Synthesis of Folate (γ)-Conjugates, and its Application to the Synthesis of Folate-Nucleoside Conguates," *Journal of Organic Chemistry*, 2000, vol. 65, pp. 5016-5021.
Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.
Oatis et al., "Synthesis of quinazoline analogues of folic acid modified at position 10," *Journal of Medical Chemistry*, 20: 1393-1396 (1977).
Patrick et al., "Folate Receptors As Potential Therapeutic Targets in Choroid Plexus Tumors of Sv40 Transgenic Mice," *J. Neurooncol,.* 32(2): 111-123 (1997).
Patrick et al., "Intracerebral bispecific ligand-antibody conjugate increases survival of animals bearing endogenously arising brain tumors," *Int. J. Cancer*, 78(4): 470-79 (1998).
Pizzorno G., et al., "Intracellular metabolism of 5,10-dideazatetrahydrofolic acid in human leukemia cell lines," *Molecular Pharmacology*, 1991, 39 (1), pp. 85-89.
Plante et al., "Polyglutamyl and polylysyl derivatives of the lysine analogues of folic acid and homofolic acid," *Journal of Medical Chemistry*, 19: 1295-1299 (1976).
Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.
Prabhu V. et al., "*Arabidopsis* dihydropteroate synthase: general properties and inhibition by reaction product and sulfonamides," *Phytochem.*, 1997; 45(1): 23-27.
Prasad et al., "Functional coupling between a bafilomycin A1—sensitive proton pump and a probenecid—sensitive folate transporter in human placental choriocarcinoma cells," *Biochim. Biophys. Acta*, 1994; 1222(2): 309.
Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.
Punj, V. et al., "Effect of Vitamin D Analog (1α Hydroxy D5) Immunoconjugated to Her-2 Antibody on Breast Cancer," *Int. J. Cancer*, 2004; 108: 922-929.
Ranasinghe, M. G. et al.; "A Facile Synthesis of Unsymmetrical Thiolsulfonates via Sulfonylation of Mercaptans," *Synthetic Communications*, 1988; 18(3), pp. 227-232.
Reddy et al., "Optimization of folate-conjugated liposomal vectors for folate receptor-mediated gene therapy," *J. Pharm. Sci*, 88(11): 1112-1118 (1999).
Reddy et al., "Preclinical evaluation of EC145, a folate-vinca alkaloid conjugate," *Cancer Res*., 2007; 67:4434-42.
Reddy et al., "Retargeting of viral vectors to the folate receptor endocytic pathway," *J Control Release*, 74(1-3): 77-82 (2001).
Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.
Remington: The Science & Practice of Pharmacy, 21th Edition (Lippincott Williams & Wilkins, 2005).

(56) References Cited

OTHER PUBLICATIONS

Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.
Rijnboutt et al., "Endocytosis of GPI-linked membrane folate receptor-alpha," *J. Cell Biol.*, 132(1-2): 35-47 (1996).
Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).
Roberts et al., "Folic acid analogs. Modifications in the benzene-ring region. 2. Thiazole analogs," *Journal of Medical Chemistry*, 15: 1310-1312 (1972).
Roberts et al., "Folic acid analogs. Modifications in the benzene-ring region. 1. 2'- and 3'-Azafolic acids," *Journal of Medical Chemistry*, 14: 125-130 (1971).
Roberts et al., "Folic acid analogs. Modifications in the benzene-ring region. 4. 3'-Ethyl- and 3'-isopropylfolic acids," *Journal of Medical Chemistry*, 17: 219-222 (1974).
Ross et al., "Differential regulation of folate receptor isoforms in normal and malignant tissues in vivo and in established cell lines. Physiologic and clinical implications," *Cancer*, 73(9): 2432-2443, (1994).
Rothberg et al, "Cholesterol controls the clustering of the glycophospholipid-anchored membrane receptor for 5-methyltetrahydrofolate," *J. Cell Biol.*, 111(6): 2931-2938 (1990).
Rothberg et al., "The glycophospholipid-linked folate receptor internalizes folate without entering the clathrin-coated pit endocytic pathway," *J. Cell Biol.*, 110(3): 637-649 (1990).
Roy et al., "Targeting T cells against brain tumors with a bispecific ligand-antibody conjugate," *Int. J. Cancer* 76(5): 761-66 (1998).
Sadasivan et al., "The complete amino acid sequence of a human folate binding protein from KB cells determined from the cDNA," *J. Biol. Chem.*, 1989; 264: 5806-5811.
Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14, 2007, 1 page.
Semb J. et al., "Pteroic Acid Derivatives. V. Pteroyl-α-glutamyl-α-glutamylglutamic Acid, Pteroyl-γ-glutamyl-αglutamylglutamic Acid, Pteroyl-α-glutamyl-γ-glutamylglutamic Acid," *JACS*, 1949; 71 (7): 2310-2315.
Senter et al., "Development of a Drug-Release Strategy Based on the Reductive Fragmentation of Benzyl Carbamate Disulfides," *J. Org. Chem.*, 55: 2975-2978 (1990).
Shimizu M. et al., "Synthesis and biological activities of new 1alpha, 25-dihydroxy-19-norvitamin D3 analogs with modifications in both A-ring and the side chain," *Bioorganic & Medicinal Chemistry*, 2006; 14(12): 4277-4294.
Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.
Shoup T.M. et al., "Synthesis of Fluorine-18-Labeled Biotin Derivatives: Biodistribution and Infection Localization," *J. Nucl. Med.*, 1994; 35: 1685-1690.
Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.
Smart et al., "Clustered folate receptors deliver 5-methyltetrahydrofolate to cytoplasm of MA104 cells," *J. Cell Biol.*, 134(5): 1169-1177 (1996).
Smart et al., "Protein kinase C activators inhibit receptor-mediated potocytosis by preventing internalization of caveolae," *J. Cell Biol.*, 124(3): 307-313 (1994).

Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6-(trifluorornethyl)benzotriazolyl] Carbonate (BTBC) and Their Reactions," *Sythesis*, 1987; 6: 557-560.
Temple et al., "Synthesis of pseudo cofactor analogs as potential inhibitors of the folate enzymes," *Journal of Medical Chemistry*, 25: 161-166 (1982).
Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.
Toffoli et al., "Overexpression of folate binding protein in ovarian cancers," *Int. J. Cancer* 74(2): 193-198 (1997).
Toraya T. et al., "Immobilized Derivatives of Vitamin B12 Coenzyme and its Analogs," *Methods in Enzymology*, vol. 67, pp. 57-66.
Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
Trachewsky D., "Antihypertensive Effect of Riboflavin Analogs in Rats with Mineralocorticoid-Induced Hypertension," *Hypertension*, 1981; vol. 3, No. 1, pp. 75-80.
Truneh A. et al., "Temperature-sensitive differential affinity of TRAIL for its receptors. DR5 is the highest affinity receptor," *J Biol Chem*, 2000; 275(30):23319-25.
Turek et al., "Endocytosis of folate-protein conjugates: ultrastructural localization in KB cells," *J. Cell Sci.* 106: 423-430 (1993).
Turk et al., "Characterization of a novel pH-sensitive peptide that enhances drug release from folate-targeted liposomes at endosomal pHs," *Biochim Biophys Acta*, 1559(1): 56-68 (2002).
Ueda M. et al., "Effect of Vitamin B12 Derivatives on Urinary Excretion of Methylmalonic Acid in Liver Diseases," *Acta Med. Okayama*, 1970; vol. 24, pp. 365-372.
Varma, R. et al., "GPI-anchored proteins are organized in submicron domains at the surface," *Nature*, 394(6695): 798-801 (1998).
Verwey, J., "Mitomycin C-Induced Renal Toxicity, a Dose-Dependent Side Effect?," *Eur J Cancer Clin Onco*, 1987; vol. 23, No. 2, pp. 195-199.
Vesely D.L. et al., "Biotin Analogs Activate Guanylate Cyclase," *Molecular and Cellular Biochemistry*, 1984; vol. 60, pp. 109-114.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 1986; 31:4307-4309.
Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA*, 92(8): 3318-3322 (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine—folate, a potential radiopharmaceutical for tumor imaging," *Bioconj. Chem.*, 1996; 7(1): 56-62.

(56) References Cited

OTHER PUBLICATIONS

Wang S. et al., "Folate-mediated targeting of antineoplastic drugs, imaging agents, and nucleic acids to cancer cells," *J. Control Rel*, 1998; 53(1-3): 39-48.

Wang, Xiu-Fang et al., "Vitamin E Analogs Trigger Apoptosis in HER2/erbB2—Overexpressing Breast Cancer Cells by Signaling via the Mitochondrial Pathway," *Biochemical and Biophysical Research Communication*, 2005; vol. 326, pp. 282-289.

Weinstock et al., "Folic acid analogs. II. p-{[(2,6-Diamino-8-purinyl)methyl]amino}-benzoyl-L-glutamic acid and related compounds," *Journal of Medical Chemistry*, 13: 995-997 (1970).

Weitman et al., "Cellular localization of the folate receptor: potential role in drug toxicity and folate homeostasis," *Cancer Res.*, 1992; 52(23): 6708-6711.

Weitman et al., "Distribution of the folate receptor GP38 in normal and malignant cell lines and tissues," *Cancer Res.*, 1992; 52(12): 3396-3401.

Westerhof GR et al., "A photoaffinity analogue of folic acid as a probe for the identification and function of a membrane folate binding protein (mFBP) in human CCRF-CEM leukemia cells," *Proceedings of the American Association for Cancer Research*, 1991; 32:328.

Wiener et al., "Targeting dendrimer-chelates to tumors and tumor cells expressing the high-affinity folate receptor," *Invest. Radiol.* 32(12): 748-54 (1997).

Wu M. et al., "Clustering of GPI-anchored folate receptor independent of both cross-linking and association with caveolin," *J. Membr. Biol.* 159(2): 137-147 (1997).

Zimmer H. et al., "Potential anticancer agents V., Synthesis of folic acid and pteroic acid analogs derived of caffeine and theophylline,"*Arzneimittelforschung*, 1966, 16(4), pp. 541-545.

Zimmerman, J., "Folic acid transport in organ-cultured mucosa of human intestine. Evidence for distinct carriers," *Gastroenterol.* 99(4): 964-972 (1990).

Angier, R. B., et al., "Pteroic Acid Analogs Containing Arsenic," J. American Chem. Soc., vol. 76, 1954, pp. 902-904.

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.

Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189 (abstract only).

Wikipedia, Derivative (Chemistry), http://en.wikipedia.org/wild/Derivative_(chemistry), downloaded Dec. 16, 2009.

Wikipedia, Analog (Chemistry), http://en.wikipedia.org/wiki/Analog_(chemistry), downloaded Dec. 16, 2009.

Wikipedia, Solution, http://en.wikipedia.org/wiki/Solution, downloaded Dec. 17, 2009.

Wikipedia, List of Purification Methods in Chemistry, http://en.wikipedia.org/wiki/List_of_purification_methods_in_chemistry, downloaded Dec. 16, 2009.

Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.

Wikipedia, Conjugate, http://en.wikipedia.org/wiki/Conjugate, downloaded Dec. 17, 2009.

Wikipedia, Complex (Chemistry), http://en.wikipedia.org/wiki/Complex_(chemistry), downloaded Dec. 23, 2009.

Leamon Christopher P., "Aspects of Folate-Mediated Drug Delivery . . . Beyond Purdue" PowerPoint Presentation presented at Purdue University on May 4, 1999, (22 pages).

Achilefu et al. "A New Method for the Synthesis of Tri-tert-butyl Diethylenetriaminepentaacetic Acid its Derivatives" *J. Org. Chem.* 2000;65:1562-1565.

Carl et al. "A novel connector linkage applicable in prodrug design" J. Med. Chem. 1981;24(5):479-480.

Coney et al. "Cloning of a tumor-associated antigent: MOv18 and MOv19 antibodies recognize a folate-binding protein" Cancer Res. 1991;51(22):6125-32.

Crapatureanu et al. "Molecular necklaces. Cross-linking hemoglobin with reagents containing covalently attached ligands" Bioconjugate Chemistry, 1999;10(6):1058-67.

Darnell, Ed. Molecular Cell Biology W. H. Freeman, San Francisco 1990;326-333.

DeNardo, Gerald. "When is Too Much Too Much and Yet Not Enough? Alas, a Plethora of Opportunities but Where's the Beef?" J. of Nuclear Medicine 2000; 41(3):470-3.

Dorwald, F. Z., "Side Reactions in Organic Synthesis: A Guide to Successful Synthesis Design," Wiley-VCH, Weinheim, 2005, p. ix of preface.

Forgac. "Structure and function of vacuolar class of ATP-driven pumps" Physiological Rev. 1989; 69(3): 765-795.

Garrett et al. "Synthesis and characterisation of polyamine-poly-(ethylene glycol) constructs for DNA binding and gene delivery" Bioorganic & Medicinal Chemistry, 2000; 8(7):1779-1797.

Henderson et al. "Mediated uptake of folate by a high-affinity binding protein in sublines of L1210 cells adapted to nanomolar concentrations of folate" J. Membrane Biol., 1988;101:247-258.

Huang et al. "Design, syntheses and sequence selective DNA cleavage of functional models of bleomycin-II. 1,2-trans-di substituted cyclopropane units as novel linkers" Bioorganic & Medicinal Chemistry, 1995;3(6):647-57.

Jansen et al., "Identification of a Membrane-Associated Folate-Binding Protein in Human Leukemic CCRF-CEM Cells with Transport-Related Methotrexate Resistance" in Cancer Res., 1989, 49, 2455-2459.

Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

Kamen et al., 1986, "Receptor-mediated folate accumulation is regulated by cellular folate content" Proc. Natl. Acad. Sci., U.S.A. 83, 5983-5987.

Ke et al. "Targeting the Tumor-Associated Folate Receptor with a I" IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.

Kemp et al. "New Protective Groups for Peptide Synthesis-I The Bic Group Base and Solvent Lability of the 5-B enzi soxazolymethyl eneoxycarbonyl amino function" Tet. Lett. 1975;52:4625-4628.

Kutsky RJ. Handbook of Vitamins, Minerals, and Hormones, 2'" Edition. New York: Van Nostrand Reinhold: 1981;263-277.

Lee et al. "Prolonged circulating lives of single-chain Fv proteins conjugated with polyethylene glycol: a comparison of conjugation chemistries and compounds" Bioconjugate Chemistry, 1999;10(6):973-81.

Li et al. "Local concentration of folate binding protein GP38 in sections of human ovarian carcinoma by concentration of in vitro quantitative autoradiography." J. Nucl. Med. 1996; 37:665-672.

Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.

Mehvar R "Dextrans for targeted and sustained delivery of therapeutic and imaging agents" [Review] Journal of Controlled Release. 2000:69(1):1-25.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miotti et al., "Characterization of Human Ovarian Carcinoma-Associated Antigens Defined by Novel Monoclonal Antibodies with Tumor—Restricted Specificity" Int. J. Cancer 1987:39:297-303.

Pastan et al, eds. "The Pathways of Endocytosis" Endocytosis, Plenum Press, New York 1985;1-40.

(56) References Cited

OTHER PUBLICATIONS

Peterson et al. "Enzymatic cleavage of peptide-linked radiolabels from immunoconjugates" Bioconiugate Chemistry 1999:10(4):553-7.
Pizzorno et al. "5,10-Dideazatetrahydrofolic acid (DDATHF) transport in CCRFCEM and MA104 cell lines." J. Biol, Chem., 1993; 268(2):247-258.
Rothenberg et al. "Further observations on the folate-binding factor in some leukemic cells" J. Clin. Invest. 1971: 50(3):719-726.
Selhub et al. "The folate binding protein of rat kidney. Purification, properties, and cellular distribution" J. Biol. Chem. 1984;259(10):6601-6606.
Selhub et al. "Renal folate adsorption and the kidney folate binding protein I. Urinary Clearance studies" Am. J. Physiol. 252:F750-F756.
Selhub et al. "Renal folate adsorption and the kidney folate binding protein II. Microinfusion studies" Am. J. Physiol. 252:F757-F760.
Sirotnak. "Obligate genetic expression in tumor cells of a fetal membrane property mediating "Folate" transport: biological significance and implications for improved therapy of human cancer" Cancer Res., 1985;45(9):3992-4000.
Stein et al. "Normal tissue reactivity of four ant tumor monoclonal antibodies of clinical interest" Int. J. Cancer 1991;47(2):163-169.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9.
Thaden et al. "Photoaffinity behavior of a conjugate of oligonucleoside methylphosphonate, rhodamine, and psoralen in the presence of complementary oligonucleotides"Bioconjugate Chemistry, 1993;4(5):386-94.
Toffoli et al. "Expression of folate binding protein as a prognostic factor for response to platinum-containing chemotherapy and survival in human ovarian cancer" Int. J. Cancer (Pred. Oncol) 1998; 79:121-126.
Weitman et al. "Distribution of the folate receptor GP38 in normal and malignant cell lines and tissues" Cancer Res. 1992;52(12):3396-3401.
Westerhof et al. "Membrane transport of natural folates and antifolate compounds in murine L1210 Leukemia cells: role of carrier-and receptor mediated transport systems" Cancer Res. 1991;51:5507-5513.
Williams et al. "Renal tubular transport of folic acid and methotrexate in the monkey" Am. J. Physiol 1982; 242(5):F484-490.
Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.
Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.
Bukanov Nikolay, O. et al., "Long-Lasting Arrest of Murine Polycystic Kidney Disease With CDK Inhibitor Roscovtiine", Dec. 14, 2006; *Nature*; vol. 444; pp. 949-952.
Hay, Nissim, et al., "Upstream and Downstream of mTOR", 2004, *Genes & Development*, vol. 18, No. 16, pp. 1926-1945.
Kennedy, Michael D., et al., "Evaluation of Folate Conjugate Uptake and Transport by the Choroid Plexus of Mice", (May 2003), vol. 20, No. 5, pp. 714-719.
Leamon, Christopher P., et al., "Folate-Liposome-Mediated Antisense Oligodeoxynucleotide Targeting to Cancer Cells: Evaluation in Vitro and in Vivo", 2003, *Bioconjugate Chemistry*, vol. 14, No. 4, pp. 738-747.
Nauta, Jeroen, et al., "Renal and Biliary Abnormalities in a New Murine Model of Autosomal Recessive Polycystic Kidney Disease", 1993, *Pediatr. Nephrol.* No. 7, pp. 163-172.
Piontek, Klaus B., et al. "A Functional Floxed Allele of *Pkd1* that Can Be Conditionally Inactivated In Vivo", *J. Am. Soc. Nephrol.* vol. 15, pp. 3035-3043.

Shillingford, Jonathan M., et al., "The mTOR Pathway is Regulated by Polycystin-1, and its Inhibition Reverses Renal Cystogenesis in Polycyclic Kidney Disease", Apr. 4, 2006, *PNAS*. vol. 103, No. 14, pp. 5466-5471.
Ke Cy et al., "Folate-Receptor-Targeting of In-111 Using Pteroic Acid Conjugates of Benzyl-DTPA and Benzyl-DOTA,"J. Nucl Med., 2004. 45(5):457P.
Regueiro-Ren et al., "Synthesis and Biological Activity of Novel Epothilone Aziridines," Organic Letters, 2001; vol. 3, No. 17: 2693-96.
Kamen et al., "A review of folate receptor alpha cycling and 5-methyltetrahydrofolate accumulation with an emphasis on cell models in vitro," Advanced Drug Delivery Reviews, 2004; vol. 56:1085-97.
Elnakat et al., "Distribution, functionality and gene regulation of folate receptor isoforms: implications in targeted therapy," Advanced Drug Delivery Reviews, 2004; vol. 56:1067-84.
Sabharanjak et al., "Folate receptor endocytosis and trafficking," Advanced Drug Delivery Reviews, 2004; vol. 56: 1099-1109.
Paulos et al., "Folate receptor-mediated targeting of therapeutic and imaging agents to activated macrophages in rheumatoid arthritis," Advanced Drug Delivery Reviews, 2004; vol. 56: 1205-17.
Antony, "Folate receptors: reflections on a personal odysssey and a perspective on unfolding truth," Advanced Drug Delivery Reviews, 2004; vol. 56: 1059-66.
Lu et al., "Folate receptor-targeted immunotherapy of cancer: mechanism and therapeutic potential," Advanced Drug Delivery Reviews, 2004; vol. 56: 1161-76.
Roy et al., "Palate-mediated targeting of T cells to tumors," Advanced Drug Delivery Reviews, 2004; vol. 56: 1219-31.
Ke et al., "Folate-receptor-targeted radionuclide imaging agents," Advanced Drug Delivery Reviews, 2004; vol. 56: 1143-60.
Gabizon et al., "Tumor cell targeting of liposome-entrapped drugs with phospholipid-anchored folic acid-PEG Conjugates," Advanced Drug Delivery Reviews, 2004; vol. 56: 1177-92.
Zhao et al., "Tumor-selective targeted delivery of genes and antisense oligodeoxyribonucleotides via the folate receptor," Advanced Drug Delivery Reviews, 2004; vol. 56: 1193-1204.
Paulos CM et al., "Ligand Binding and Kinetics of Folate Receptor Recycling in Vivo: Impact on Receptor-Mediated Drug Delivery " Molecular Pharmacology 2004: 66:1406-1414.
Griesser UJ, "The Importance of Solvents," in Polymorphism in the Pharmaceutical Industry, Hilfiker ed., 2006; p. 211-230.
Wikipedia, Structural analog, http://en.wikipedia.org/wiki/Structural_analog, downloaded Apr. 7, 2009.
Wikipedia, Folic acid, http://en.wikipedia.org/wiki/Folic_acid, downloaded Apr. 7, 2009.
Wikipedia, Functional analog, http://en.wikipedia.org/wiki/Functional_analog, downloaded Apr. 7, 2009.
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.
Matulic-Adamic J et al., "An efficient synthesis of the ribozyme-folate conjugate," Tetrahedron Letters, 2002; 43(25):4439-4441.
Harrison JG et al., A convenient synthetic route to oligonucleotide conjugates,: Bioorganic & Medicinal Chemistry Letters, 1997; 7(8): 1041-1046.
Dyson G., May P. "The Chemistry of Synthetic Pharmaceutical Substances", translation from English M.:-"The World", 1964, pp. 12-19.
Mashkovskiy M.D. Drugs, Moscow, New wave, 2001, vol. I, p. 11.
Robert Laplanche, et al.,"Physiologically Based Pharmacokinetic (PBPK) Modeling of Everolimus (RAD001) in Rats Involving Non-Linear Tissue Uptake,"Journal of Pharmacokinetics and Pharmacodynamics, 2007, vol. 34, No. 3, 373-400.
Pathalk et al., Enzymic protecting group techniques in organic synthesis, Stereosel. Biocatal. 775-797 (2000).

(56) References Cited

OTHER PUBLICATIONS

Dube D et al., "Preparation and Tumor Cell Uptake of Poly(*N*-isopropylacrylamide) Folate Conjugates"; *Bioconjugate Chem*, 2002; 13: 685-692.
Evans et al., "Synthessis of biotin conjugates of the antifungal compound cymoxanil," *Pest Manag Sci*, 2002; 58: 392-396.
Rao et al., Journal of Medicinal Chemistry, 1985, 28:1079-1088.
Conrad et al, Journal of Medicinal Chemistry, 1979, 22(4): 391-400.
Wang et al., "Structure-activity and high-content imaging analyses for novel tubulysins," Chemical Biology & Drug Design, 2007; 70(2): 75-86.
Patterson et al., "Design, synthesis, and biological properties of highly potent tubulysin D analogues," Chemistry—A European Journal, 2007; 13(34): 9534-9541.
Golub, T.R., et al., "Molecular Classification of Cancer: Class Discovery and Class Prediction by Gene Expression Monitoring," Science, 1999, vol. 286, 531-537 (Oct. 15, 1999).
Speckamp, et al.; "New Developments in the Chemistry of N-Acyliminium Ions and Related Intermediates" Tetrahedron 2000 vol. 56(24) 3817-3856.
Angier et al., Science, 1946, 103: 667-669.
Wolf et al., Journal of the American Chemical Society, 1947, 69: 2753-2759.
Parker et al., "Folate receptor expression in carcinomas and normal tissues determined by a quantitative radioligand binding assay," Analytical Biochemistry, 2005; 335:284-293.
Remy et al., Proceedings of the National Academy of Sciences of the United States of America, 1999, vol. 96, No. 10, pp. 5394-5399.
Na, Wang, and Kohn, "7-N-(Mercaptoalkylmitomycins: Implications of Cyclization for Drug Function," J Am Chem Soc 124:4666-77 (2002 ).
Putnam et al., "Polymer conjugates with anticancer activity", Advances in Polymer Science 1995, 122, 55-123.
Umemoto et al., "Molecular design of methotrexate-antibody conjugates for targeted cancer treatment", Journal of Bioactive and Compatible Polymers, 1992, 7(2), 191-219.
Sanderson et al., "In vivo drug-linker stability of an anti-CD30 dipeptide-linked auristatin immunoconjugate," *Clinical Cancer Research*, 2005; 11:843-852.
Wu et al., "Enhancing the enantioselectivity of candida lipase catalyzed ester hydrolysis via noncovalent enzyme modification," *Journal of American Chemical Society*, 1990; 112:1990-1995.
Patterson et al., "Expedient synthesis of N-Methyl tubulysin analogues with high cytotoxicity," *Journal of Organic Chemistry*, 2008; 73:4365-4369.
Gabizon et al., Clin Cancer Res 9:6551-59 (2003).
Pouvreau, Isabelle et al.: "Effect of macrophage depletion by liposomes containing dichloromethylene-diphosphonate on endotoxin induce uveitis." J. Neuroimmun. (1998)86 p. 171-181.
U.S. Appl. No. 60/808,367, filed May 25, 2006, Vite et al.
Lindstedt, E.W. et al.; "Anti-tnf-alpha therapy for sight threatening uveitis." Br. J. Opthalmol. (2005) 89 p. 533-536.
Mangel, Andreas: GMP news, 2002, www.gmp-compliance.ord/eca_news_159.html, downloaded Mar. 19, 2014.
Kaneko, Takushi, "New Hydrazone Derivatives of Adiramycin and their Immunoconjugates—A Correlation between Acid Stability and Cytotoxicity", *Bioconj. Chem.*, vol. 2, No. 3, pp. 131-141 (May 1, 1991).
PCT International Search Report/Written Opinion for PCT/US2009/061049, completed Mar. 15, 2010.

Polyak et al., "Introduction of spacer peptides N-terminal to a cleavage recognition motif in recombinant fusion proteins can improve site-specific cleavage," Protein Eng., 1997; 10(6):615-9.
Univesity of Maryland Medical Center (UMMC), Vitamin B9 (folic acid), 2014, http://umm.edu/health/medical/altmed/supplement/vitamin-b9-folic-acid, pp. 1-8.
Cerner Multum, Inc., Drugs.com, Folic Acid, http://www.drugs.com/folic_acid.html?printable=1, 1996-2014, Version:5.01, Revision Date 10/15/2009, pp. 104.
PCT International Search Report and Written Opinion for PCT/US2008/056824, completed Jul. 24, 2009.
PCT International Search Report/Written Opinion prepared for PCT/US2010/061897, mailed Mar. 11, 2011.
European Search Report prepared for corresponding European Application Serial No. 08841521.1, mailed Jul. 18, 2011.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
International Search Report and Written Opinion for PCT/US2008/056824 completed Jul. 24, 2009.
Vlahov I. et al., "An assembly concept for the consecutive introduction of unsymmetrical disulfide bonds: synthesis of a releasable multidrug conjugate of folic acid," 2007, J. Org Chem, 72, 5968-5972.
Wang, L. et al., "Synthesis, biological, and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase," 2011, J. Med. Chem., 54, 7150-7164.
Vlahov I. et al., "Design and regioselective synthesis of a new generation of targeted therapeutics. Part 3: Folate conjugates of aminopterin hydrazide for the treatment of inflammation," 2011, Bioorg. Med. Chem. Lett., 21, 1202-1205.
Vlahov, I. et al., "Design and regioselective synthesis of a new generation of targeted chemotherapeutics. Part II: Folic acid conjugates of tubulysins and their hydrazides," Bioorg. Med. Chem. Lett., 2008, 18(16), 4558-4561.
Endocyte: Endocyte Enrolls First Patient in Phase 1 Study for the Small Molecule Drug Conjugate EC1456, a Folate-Targeted Tubulysin Conjugate in Advanced Solid Tumors. Dec. 2013. [Retrieved on May 6, 2015].
Leamon, et al., "Patient selection and targeted treatment in the management of platinum-resistant ovarian cancer," Pharmacogenomics and Personalized Medicine, 6:113-125 (2013).
Zaragoza, D., Side Reactions in Organic Synthesis, 2005, Wiley-VCH Verlag GmbH & Co. KGaA, Weinheim, Preface, p. 9.
Attur, M. et al., "Differential anti-inflammatory effects of immunosuppressive drugs: Cyclosporin, rapamycin and FK-506 on inducible nitric oxide synthase, nitric oxide, cyclooxygenase-2 and $PGE_2$ production," Inflamm. res. 2000, 49, 020-026.
Lorusso, P. M. et al., "Phase I Study of Folate Conjugate EC145 (Vintafolide) in Patients with Refractory Solid Tumors," J. Clinical Oncology, 2012, 30, No. 32, 4011-4016.

\* cited by examiner

BINDING LIGAND LINKED DRUG DELIVERY CONJUGATES OF TUBULYSINS

CROSS REFERENCE TO RELATED APPLICATIONS

This application claims the benefit of priority under 35 U.S.C. §119(e) of U.S. provisional patent application Ser. No. 60/911,551 filed Apr. 13, 2007, and U.S. provisional patent application Ser. No. 60/894,901 filed 14 Mar. 2007, the disclosures of which are incorporated herein by reference in their entirety.

TECHNICAL FIELD

This application is a U.S. national application under 37 C.F.R. §371(b) of International Application Serial No. PCT/US2008/056824 filed Mar. 13, 2008, which claims the benefit of priority under 35 U.S.C. §119(e) of U.S. provisional patent application Ser. No. 60/911,551 filed Apr. 13, 2007, and U.S. provisional patent application Ser. No. 60/894,901 filed 14 Mar. 2007, the disclosures of which are incorporated herein by reference in their entirety.

BACKGROUND

The mammalian immune system provides a means for the recognition and elimination of tumor cells, other pathogenic cells, and invading foreign pathogens. While the immune system normally provides a strong line of defense, there are many instances where cancer cells, other pathogenic cells, or infectious agents evade a host immune response and proliferate or persist with concomitant host pathogenicity. Chemotherapeutic agents and radiation therapies have been developed to eliminate, for example, replicating neoplasms. However, many of the currently available chemotherapeutic agents and radiation therapy regimens have adverse side effects because they work not only to destroy pathogenic cells, but they also affect normal host cells, such as cells of the hematopoietic system. The adverse side effects of these anticancer drugs highlight the need for the development of new therapies selective for pathogenic cell populations and with reduced host toxicity.

Researchers have developed therapeutic protocols for destroying pathogenic cells by targeting cytotoxic compounds to such cells. Many of these protocols utilize toxins conjugated to antibodies that bind to antigens unique to or overexpressed by the pathogenic cells in an attempt to minimize delivery of the toxin to normal cells. Using this approach, certain immunotoxins have been developed consisting of antibodies directed to specific antigens on pathogenic cells, the antibodies being linked to toxins such as ricin, Pseudomonas exotoxin, Diptheria toxin, and tumor necrosis factor. These immunotoxins target pathogenic cells, such as tumor cells, bearing the specific antigens recognized by the antibody (Olsnes, S., Immunol. Today, 10, pp. 291-295, 1989; Melby, E. L., Cancer Res., 53(8), pp. 1755-1760, 1993; Better, M. D., PCT Publication Number WO 91/07418, published May 30, 1991).

Another approach for targeting populations of pathogenic cells, such as cancer cells or foreign pathogens, in a host is to enhance the host immune response against the pathogenic cells to avoid the need for administration of compounds that may also exhibit independent host toxicity. One reported strategy for immunotherapy is to bind antibodies, for example, genetically engineered multimeric antibodies, to the surface of tumor cells to display the constant region of the antibodies on the cell surface and thereby induce tumor cell killing by various immune-system mediated processes (De Vita, V. T., Biologic Therapy of Cancer, 2d ed. Philadelphia, Lippincott, 1995; Soulillou, J. P., U.S. Pat. No. 5,672,486). However, these approaches have been complicated by the difficulties in defining tumor-specific antigens.

Tubulysins are a group of potent inhibitors of tubulin polymerization. Tubulysins are useful in treating diseases and disease states that include pathogenic cell populations, such as cancer. Two particular species of mycobacteria synthesize tubulysins in high titer during fermentation. One species, *Archangium gephyra*, produces as the main component factors tubulysins A, B, C, G, and I, each of which is characterized by a including the tubutyrosine (Tut, an analog of tyrosine) residue. In contrast, another species, *Angiococcus disciformis*, produces as the main component factors tubulysins D, E, F, and H, each of which is characterized by a including the tubuphenylalanine (Tup, an analog of phenylalanine) residue. Such bacterial fermentations are convenient sources of tubulysins.

SUMMARY OF THE INVENTION

In one illustrative embodiment of the invention, conjugates of tubulysins having the formula

B-L-D are described where B is a binding or targeting ligand, L is a relesable linker, and D is a tubulysin, or an analog or derivative thereof. It is to be understood that as used herein, the term tubulysin refers both individually and/or collectively to naturally occurring tubulysins, synthetically prepared tubulysins, and analogs and derivatives of such compounds.

In another embodiment, conjugates of tubulysin comprising a binding or targeting ligand B, a polyvalent releasable linker L, and one or more drugs D are described, where at least one drug D is a first tubulysin, and where B and D are each covalently bonded to L.

In another embodiment, conjugates of tubulysins of the formula

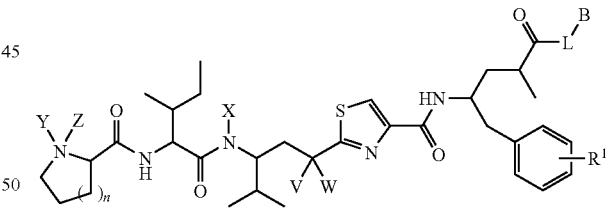

and pharmaceutical salts thereof are described herein, where B is a binding or targeting ligand, L is a relesable linker, n is 1-3;

V is H, $OR^2$, or halo, and W is H, $OR^2$, or alkyl, where $R^2$ is independently selected in each instance from H, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl, each of which is optionally substituted;

Z is alkyl and Y is O; or Z is alkyl or C(O)R$^4$, and Y is absent, where R$^4$ is alkyl, CF$_3$, or aryl;

R$^1$ is H, or R$^1$ represents 1 to 3 substituents selected from halo, nitro, carboxylate or a derivative thereof, cyano, hydroxyl, alkyl, haloalkyl, alkoxy, haloalkoxy, phenol protecting groups, prodrug moieties, and OR$^6$, where R$^6$ is optionally substituted aryl, C(O)R$^7$, P(O)(OR$^8$)$_2$, or SO$_3$R$^8$, where R$^7$ and R$^8$ are independently selected in each instance from H, alkyl, alkenyl, cycloalkyl, heterocyclyl, aryl, and arylalkyl, each of which is optionally substituted, or R$^8$ is a metal cation; and R is OH or a leaving group, or R forms a carboxylic acid derivative.

In another embodiment, conjugates of naturally occurring tubulysins are described herein, where the tubulysins are conjugated to a binding or targeting ligand via an optional releasable linker L.

In another embodiment, the conjugates described herein are included in pharmaceutical compositions in amounts effective to treat diseases and disease states associated with pathogenic populations of cells.

In another embodiment, the conjugates described herein, and pharmaceutical compositions containing them are used in methods for treating diseases and disease states associated with pathogenic populations of cells.

DETAILED DESCRIPTION

Figure 1:
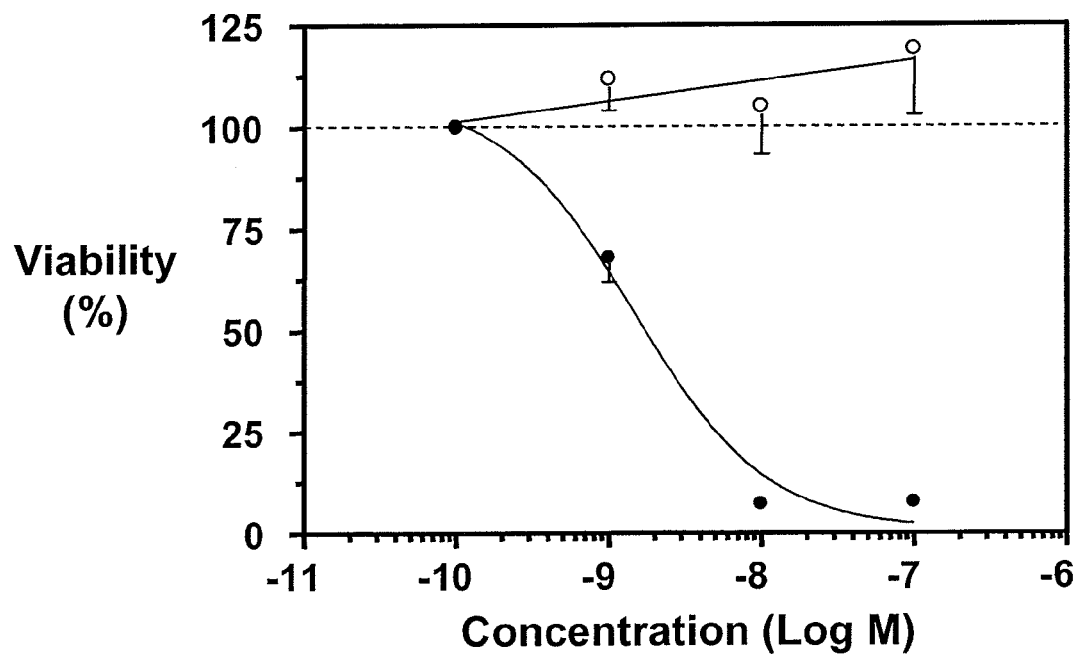
FIG. 1 shows that EC0305 exhibited dose-responsive behavior and specificity for the folate receptor after a 2 hour pulse and a 72 hour chase against KB cells: (●) EC0305 (IC$_{50}$~1.5 nM); (○) EC0305+excess folic acid.

Drug delivery conjugates are described herein consisting of a binding ligand (B), a bivalent linker (L), and a tubulysin (D), including analogs and derivatives thereof. The binding ligand (B) is covalently attached to the bivalent linker (L), and the tubulysin, or analog or derivative thereof, is also covalently attached to the bivalent linker (L). The bivalent linker (L) comprises one or more spacer linkers and/or releasable linkers, and combinations thereof, in any order. In one variation, releasable linkers, and optional spacer linkers are covalently bonded to each other to form the linker. In another variation, a releasable linker is directly attached to the tubulysin, or analog or derivative thereof. In another variation, a releasable linker is directly attached to the binding ligand. In another variation, either or both the binding ligand and the tubulysin, or analog or derivative thereof, is attached to a releasable linker through one or more spacer linkers. In another variation, each of the binding ligand and the tubulysin, or analog or derivative thereof, is attached to a releasable linker, each of which may be directly attached to each other, or covalently attached through one or more spacer linkers. From the foregoing, it should be appreciated that the arrangement of the binding ligand, and the tubulysin, or analog or derivative thereof, and the various releasable and optional spacer linkers may be varied widely. In one aspect, the binding ligand, and the tubulysin, or analog or derivative thereof, and the various releasable and optional spacer linkers are attached to each other through heteroatoms, such as nitrogen, oxygen, sulfur, phosphorus, silicon, and the like. In variations, the heteroatoms, excluding oxygen, may be in various states of oxidation, such as N(OH), S(O), S(O)₂, P(O), P(O)₂, P(O)₃, and the like. In other variation, the heteroatoms may be grouped to form divalent radicals, such as for example hydroxylamines, hydrazines, hydrazones, sulfonates, phosphinates, phosphonates, and the like.

In one aspect, the receptor binding ligand (B) is a vitamin, or analog or derivative thereof, or another vitamin receptor binding compound.

As used herein, tubulysins refer generally to tetrapeptide compounds of the formula

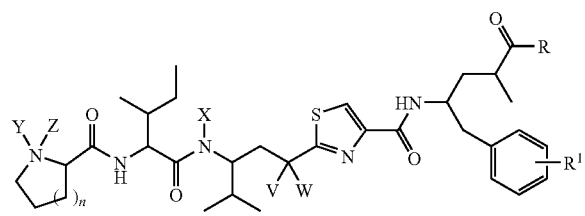

and pharmaceutical salts thereof, where n is 1-3;

V is H, OR², or halo, and W is H, OR², or alkyl, where R² is independently selected in each instance from H, alkyl, and C(O)R³, where R³ is alkyl, cycloalkyl, alkenyl, aryl, or arylalkyl, each of which is optionally substituted; providing that R² is not H when both V and W are OR²; or V and W are taken together with the attached carbon to form a carbonyl;

X=H, $C_{1-4}$ alkyl, alkenyl, each of which is optionally substituted, or CH₂QR⁹; where Q is —N—, —O—, or —S—; R⁹=H, $C_{1-4}$ alkyl, alkenyl, aryl, or C(O)R¹⁰; and R¹⁰=$C_{1-6}$ alkyl, alkenyl, aryl, or heteroaryl, each of which is optionally substituted;

Z is alkyl and Y is O; or Z is alkyl or C(O)R⁴, and Y is absent, where R⁴ is alkyl, CF₃, or aryl;

R¹ is H, or R¹ represents 1 to 3 substituents selected from halo, nitro, carboxylate or a derivative thereof, cyano, hydroxyl, alkyl, haloalkyl, alkoxy, haloalkoxy, phenol protecting groups, prodrug moieties, and OR⁶, where R⁶ is optionally substituted aryl, C(O)R⁷, P(O)(OR⁸)₂, or SO₃R⁸, where R⁷ and R⁸ are independently selected in each instance from H, alkyl, alkenyl, cycloalkyl, heterocyclyl, aryl, and arylalkyl, each of which is optionally substituted, or R⁸ is a metal cation; and R is OH or a leaving group, or R forms a carboxylic acid derivative.

Conjugates of each of the foregoing tubulysins are described herein. In one variation, Z is methyl. In another variation, R¹ is H. In another variation, R¹ is OR⁶ at C(4), where R⁶ is H, alkyl, or COR⁷. In another variation, V is H, and W is OC(O)R³.

In another embodiment, conjugates of tubulysins of the following general formula are described

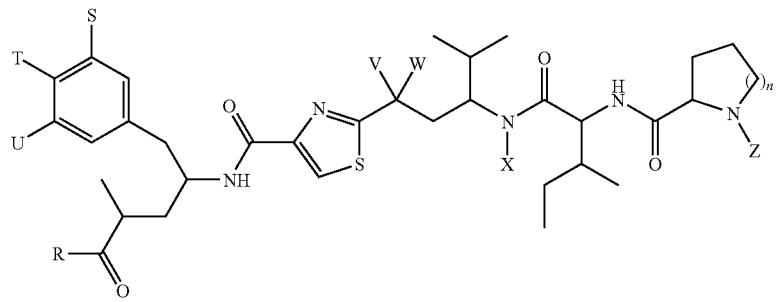

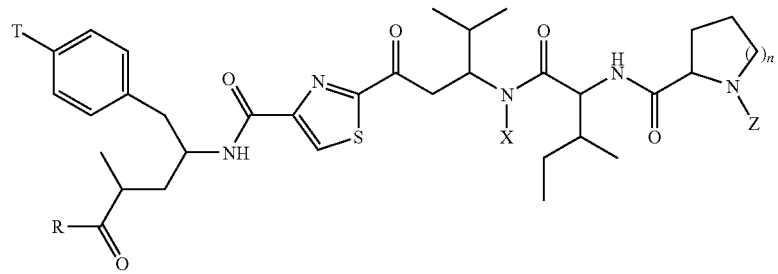

and pharmaceutical salts thereof, where n is 1-3;

V is H, OR², or halo, and W is H, OR², or alkyl, where R² is independently selected in each instance from H, alkyl, or C(O)R³, where R³ is alkyl, alkenyl or aryl, providing that R² is not H when both V and W are OR²; or V and W are taken together with the attached carbon to form a carbonyl;

X=H, C$_{1-4}$ alkyl, alkenyl, each of which is optionally substituted, or CH$_2$QR$^9$; where Q is —N—, —O—, or —S—; R$^9$=H, C$_{1-4}$ alkyl, alkenyl, aryl, or C(O)R$^{10}$; and R$^{10}$=C$_{1-6}$ alkyl, alkenyl, aryl, or heteroaryl, each of which is optionally substituted;

Z is alkyl or C(O)R$^4$, where R$^4$ is alkyl, CF$_3$, or aryl;

T is H or OR$^6$, where R$^6$ is H, alkyl, aryl, COR$^7$, P(O)(OR$^8$)$_2$, or SO$_3$R$^8$, where R$^7$ and R$^8$ are independently selected in each instance from H, alkyl, alkenyl, cycloalkyl, heterocyclyl, aryl, and arylalkyl, each of which is optionally substituted, or R$^8$ is a metal cation, or R$^6$ is a phenol protecting group, or a prodrug moiety;

S and U are each independently selected from the group consisting of H, halo, nitro, cyano, alkyl, haloalkyl, alkoxy, and haloalkoxy; and R is OH or a leaving group, or R forms a carboxylic acid derivative.

In one variation, Z is methyl or C(O)R$^4$.

Natural tubulysins are generally linear tetrapeptides consisting of N-methyl pipecolic acid (Mep), isoleucine (Ile), an unnatural aminoacid called tubuvalin (Tuv), and either an unnatural aminoacid called tubutyrosine (Tut, an analog of tyrosine) or an unnatural aminoacid called tubuphenylalanine (Tup, an analog of phenylalanine). In another embodiment, naturally occurring tubulysins, and analogs and derivatives thereof, of the following general formula are described

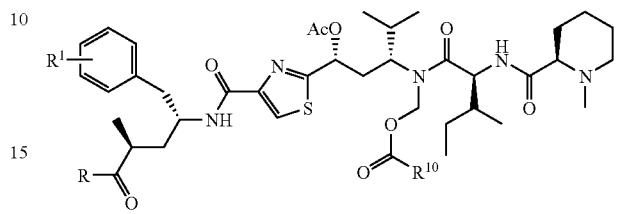

and pharmaceutical salts thereof, where R, R$^1$, and R$^{10}$ are as described in the various embodiments herein. Conjugates of each of the foregoing tubulysins are described herein.

In another embodiment, conjugates of naturally occurring tubulysins of the following general formula are described

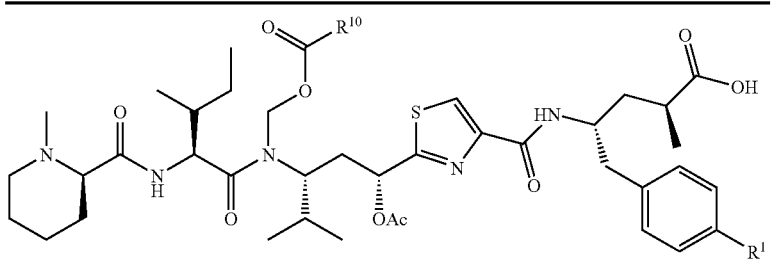

| Factor | R$^{10}$ | R$^1$ |
|---|---|---|
| A | (CH$_3$)$_2$CHCH$_2$ | OH |
| B | CH$_3$(CH$_2$)$_2$ | OH |
| C | CH$_3$CH$_2$ | OH |
| D | (CH$_3$)$_2$CHCH$_2$ | H |
| E | CH$_3$(CH$_2$)$_2$ | H |
| F | CH$_2$CH$_3$ | H |
| G | (CH$_3$)$_2$C=CH | OH |
| H | CH$_3$ | H |
| I | CH$_3$ | OH | and pharmaceutical salts thereof.

In another embodiment, conjugates of tubulysins of the following formula are described:

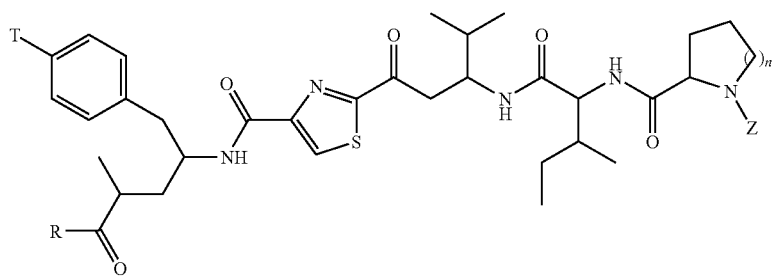

and pharmaceutical salts thereof, where n is 1-3; T is H or OR$^6$, where R$^6$ is H, alkyl, aryl, COR$^7$, P(O)(OR$^8$)$_2$, or SO$_3$R$^8$, where R$^7$ and R$^8$ are independently selected in each instance from H, alkyl, alkenyl, cycloalkyl, heterocyclyl, aryl, and arylalkyl, each of which is optionally substituted, or R$^8$ is a metal cation, or R$^6$ is a phenol protecting group, or a prodrug moiety; Z is alkyl or C(O)R⁴, where R⁴ is alkyl, CF₃, or aryl; and R is OH or a leaving group, or R forms a carboxylic acid derivative. Illustrative examples of such compounds, and their preparation are described in J. Med. Chem. 10.1021/jm701321p (2008), the disclosure of which is incorporated herein by reference.

In another embodiment, conjugates of tubulysins of the following formula are described:

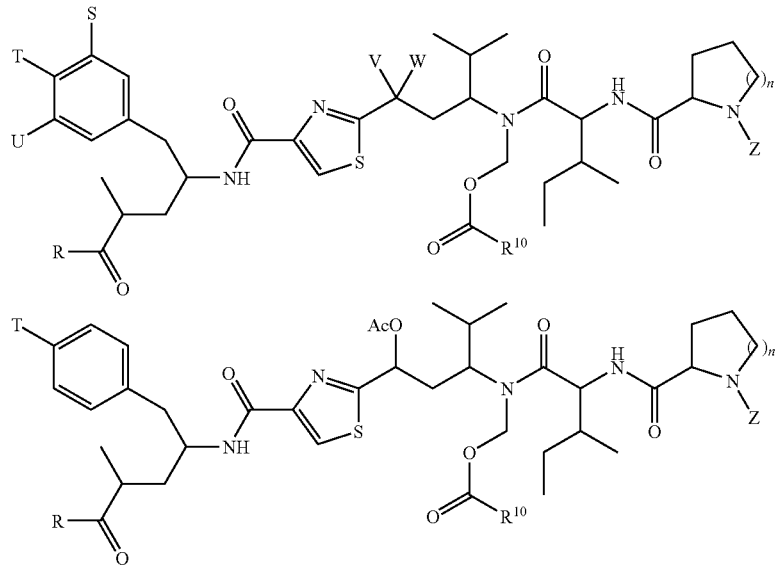

and pharmaceutical salts thereof, where n, S, T, U, V, W, Z, R, and $R^{10}$ are as described in the various embodiments herein.

In another embodiment, conjugates of tubulysins of the following formula are described:

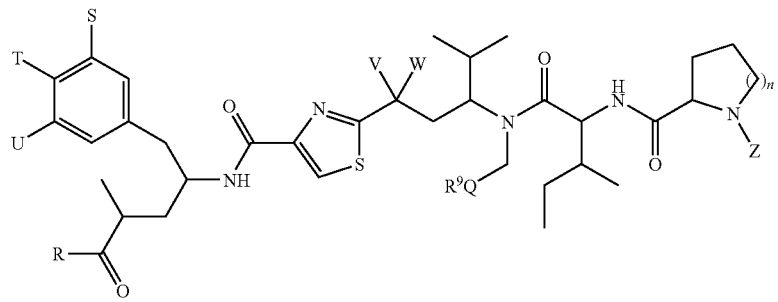

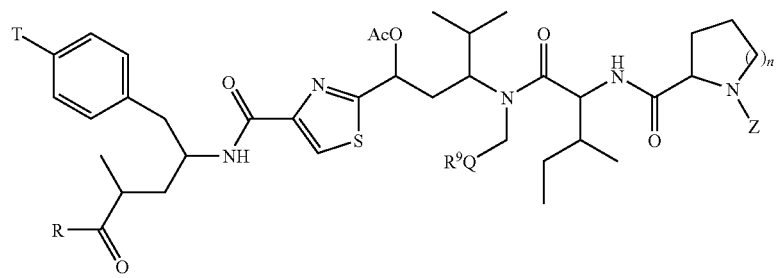

and pharmaceutical salts thereof, where n, S, T, U, V, W, Z, $QR^9$, and R are as described in the various embodiments herein. In one variation, Q is —N—, —O—, or —S—; and $R^9$ is H, alkyl, alkenyl, cycloalkyl, aryl, or arylalkyl, each of which is optionally substituted. In another variation, $QR^9$ are taken together to form $C(O)R^{10}$, $S(O)_2R^{10}$, $P(O)(OR^{10a})_2$, where $R^{10}$ and $OR^{10a}$ are independently selected in each instance from the group consisting of H, alkyl, alkenyl, cycloalkyl, aryl, and arylalkyl, each of which is optionally substituted, or $R^{10a}$ is a metal cation.

In another embodiment, conjugates of tubulysins of the following formula are described:

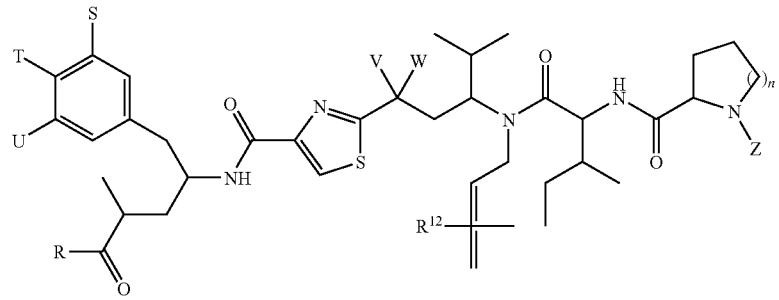

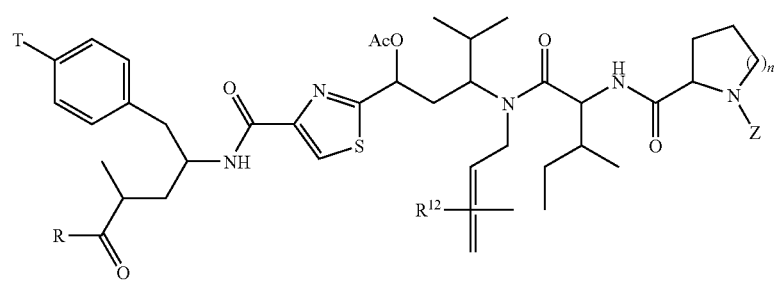

and pharmaceutical salts thereof, where $R^{12}$ represents 1 or more substituents selected from alkyl, alkenyl, cycloalkyl, aryl, and arylalkyl, each of which is optionally substituted; and where n, S, T, U, V, W, Z, and R are as described in the various embodiments herein. It is to be understood that other olefins may form by isomerization, depending on the conditions of the reaction and the identity of $R^1$. For example, when $R^1$ is alkyl, it is appreciated that under the reaction conditions, the double bond can migrate to other carbon atoms along the alkenyl chain, including to form the terminal or ω-olefin.

In another embodiment, conjugates of tubulysins of the following formula are described:

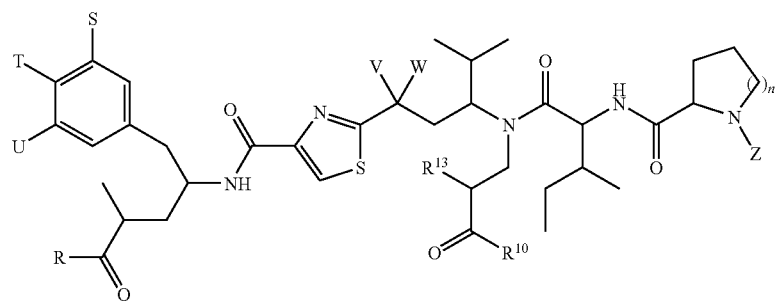

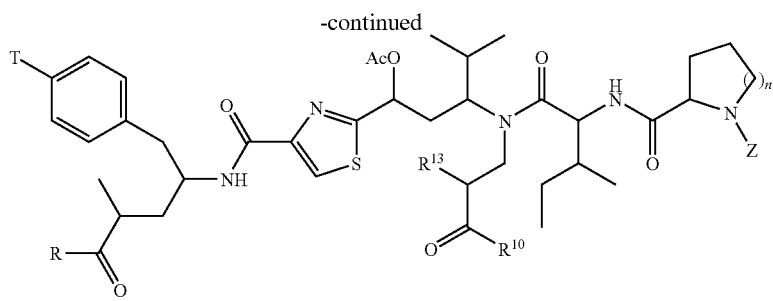

and pharmaceutical salts thereof, where $R^{13}$ is $C(O)R^{10}$, $C(O)OR^{10}$ or CN; and where n, S, T, U, V, W, Z, R, and $R^{10}$ are as described in the various embodiments herein, where $R^{10}$ is independently selected in each instance.

In another embodiment, conjugates of tubulysins of the following formula are described:

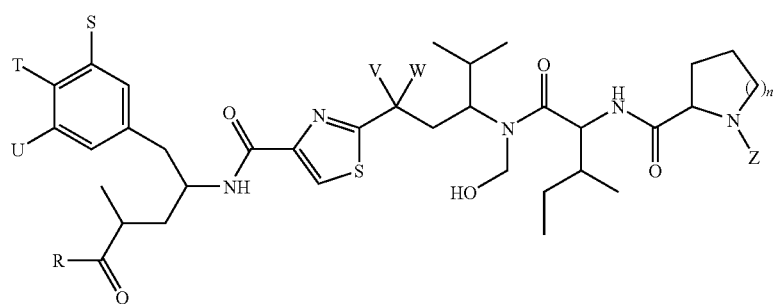

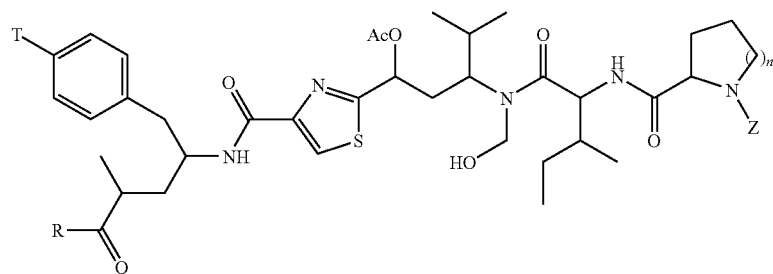

and pharmaceutical salts thereof, where n, S, T, U, V, W, Z, and R are as described in the various embodiments herein.

In another embodiment, conjugates of tubulysins of the following formula are described:

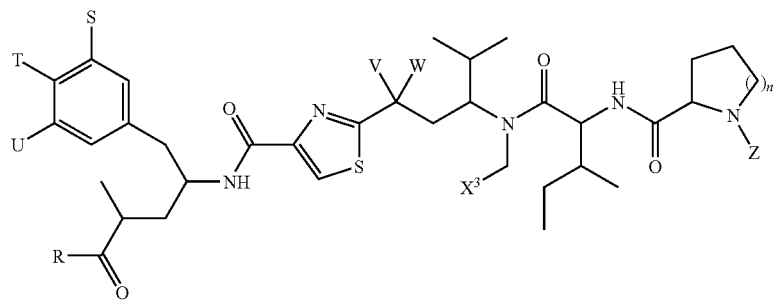

-continued

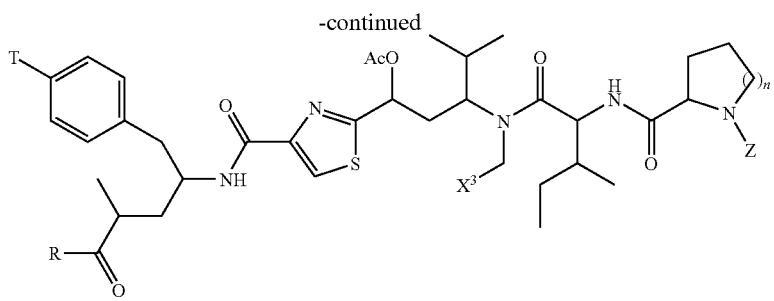

and pharmaceutical salts thereof, where $X^3$ is halogen, $OS(O)_2R^{10}$, $OP(O)(OR^{10a})R^{10}$, or $OP(O)(OR^{10a})_2$; where $R^{10}$ and $R^{10a}$ are independently selected in each instance from the group consisting of H, alkyl, alkenyl, cycloalkyl, aryl, and arylalkyl, each of which is optionally substituted, or $R^{10a}$ is a metal cation; and where n, S, T, U, V, W, Z, and R are as described in the various embodiments herein.

Additional tubulysins useful in preparing the conjugates described herein are described in US patent application publication Nos. 2006/0128754 and 2005/0239713, the disclosures of which are incorporated herein by reference. Additional tubulysins useful in preparing the conjugates described herein are described in co-pending U.S. provisional application Ser. Nos. 60/982,595 and 61/036,176, the disclosures of which are incorporated herein by reference. Tubulysins may also be prepared are described in Peltier et al., "The Total Synthesis of Tubulysin D," J. Am. Chem. Soc. 128:16018-19 (2006), the disclosure of which is incorporated herein by reference.

In each of the foregoing embodiments, it is understood that in one variation, the compounds of the various formulae have the following absolute configuration:

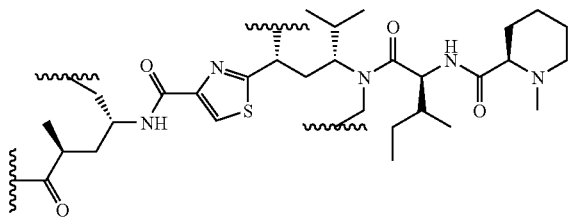 [SMILES: *C[C@@H](C[C@H](C)C(*)=O)NC(=O)c1csc([C@H](*)C[C@H](C(C)C)N(C*)C(=O)[C@@H](NC(=O)[C@H]2CCCCN2C)C(C)CC)n1]

at the indicated asymmetric backbone carbon atoms.

It is to be understood that the conjugate of the tubulysin or analog or derivative thereof may be formed at any position. Illustratively, conjugates of tubulysins are described where the bivalent linker (L) is attached to any of the following positions:

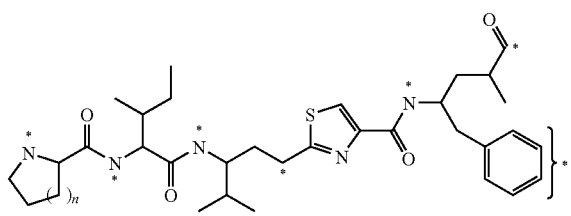

where the (*) symbol indicates optional attachment locations.

In another embodiment, the conjugates are formed from carboxylic acid derivatives of the tubulysin, or analog or derivative thereof. Illustrative carboxylic acid conjugate derivatives of the tubulysin are represented by the following general formula

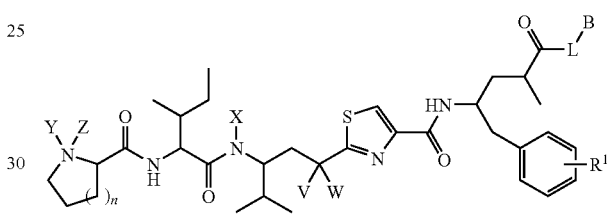

and pharmaceutical salts thereof, where

B is a binding ligand;

L is a linker; where L includes a heteroatom linker covalently attached to the tubulysin, such as an oxygen, nitrogen, or sulfur heteroatom;

n is 1-3;

V is H, $OR^2$, or halo, and W is H, $OR^2$, or alkyl, where $R^2$ is independently selected in each instance from H, alkyl, or $C(O)R^3$, where $R^3$ is alkyl, alkenyl or aryl, providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl, each of which is optionally substituted;

Z is alkyl and Y is O; or Z is alkyl or $C(O)R^4$, and Y is absent, where $R^4$ is alkyl, $CF_3$, or aryl;

$R^1$ is H, or $R^1$ represents 1 to 3 substituents selected from halo, nitro, carboxylate or a derivative thereof, cyano, hydroxyl, alkyl, haloalkyl, alkoxy, haloalkoxy, phenol protecting groups, prodrug moieties, and $OR^6$, where $R^6$ is optionally substituted aryl, $C(O)R^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and R is OH or a leaving group, or R forms a carboxylic acid derivative.

In another embodiment, illustrative carboxylic acid conjugate derivatives of tubulysin of the following general formula are described

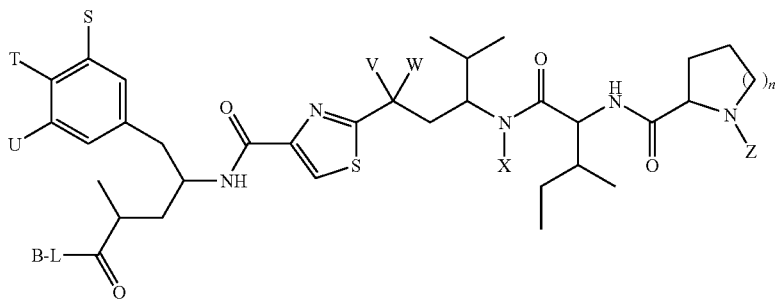

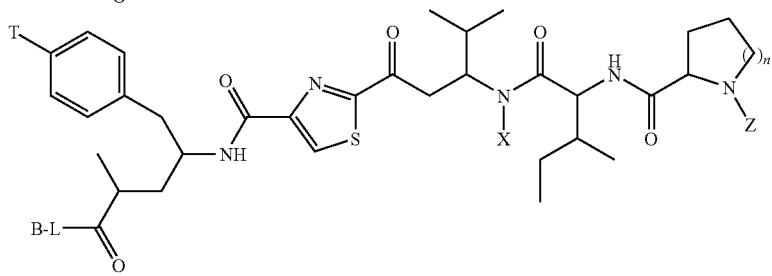

and pharmaceutical salts thereof, where

B is a binding ligand;

L is a linker; where L includes a heteroatom linker covalently attached to the tubulysin, such as an oxygen, nitrogen, or sulfur heteroatom;

n is 1-3;

V is H, $OR^2$, or halo, and W is H, $OR^2$, or alkyl, where $R^2$ is independently selected in each instance from H, alkyl, or $C(O)R^3$, where $R^3$ is alkyl, alkenyl or aryl, providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —N—, —O—, or —S—; $R^9$=H, $C_{1-4}$ alkyl, alkenyl, aryl, or $C(O)R^{10}$; and $R^{10}$=$C_{1-6}$ alkyl, alkenyl, aryl, or heteroaryl, each of which is optionally substituted;

Z is alkyl or $C(O)R^4$, where $R^4$ is alkyl, $CF_3$, or aryl;

T is H or $OR^6$, where $R^6$ is H, alkyl, aryl, $COR^7$, $P(O)(OR^8)_2$, or $SO_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation, or $R^6$ is a phenol protecting group, or a prodrug moiety;

S and U are each independently selected from the group consisting of H, halo, nitro, cyano, alkyl, haloalkyl, alkoxy, and haloalkoxy; and R is OH or a leaving group, or R forms a carboxylic acid derivative.

In another embodiment, illustrative carboxylic acid conjugate derivatives of the following general formulae are described

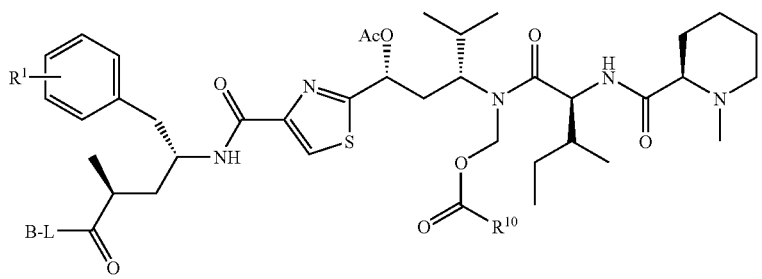

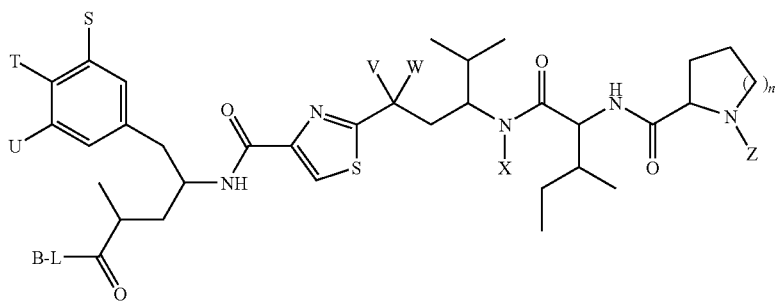

-continued
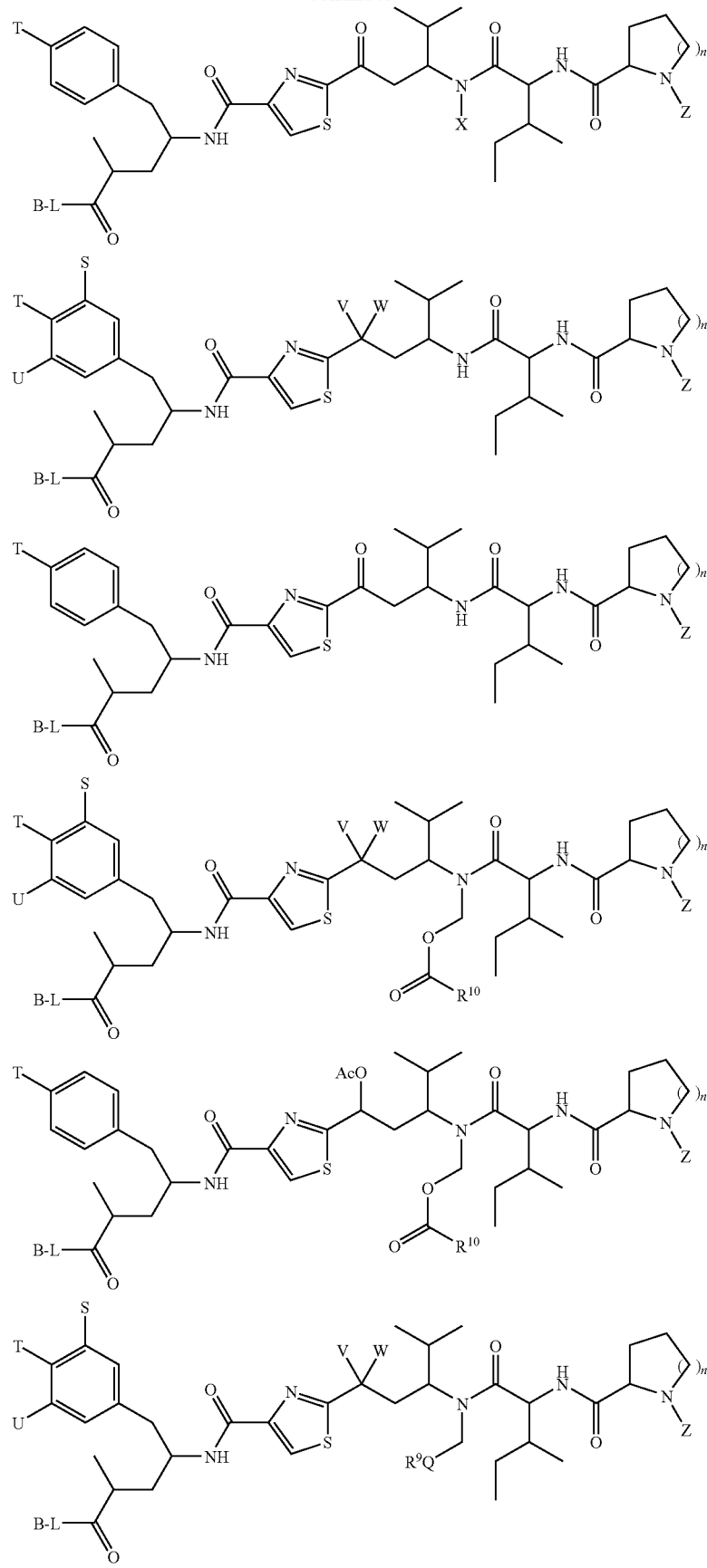

-continued
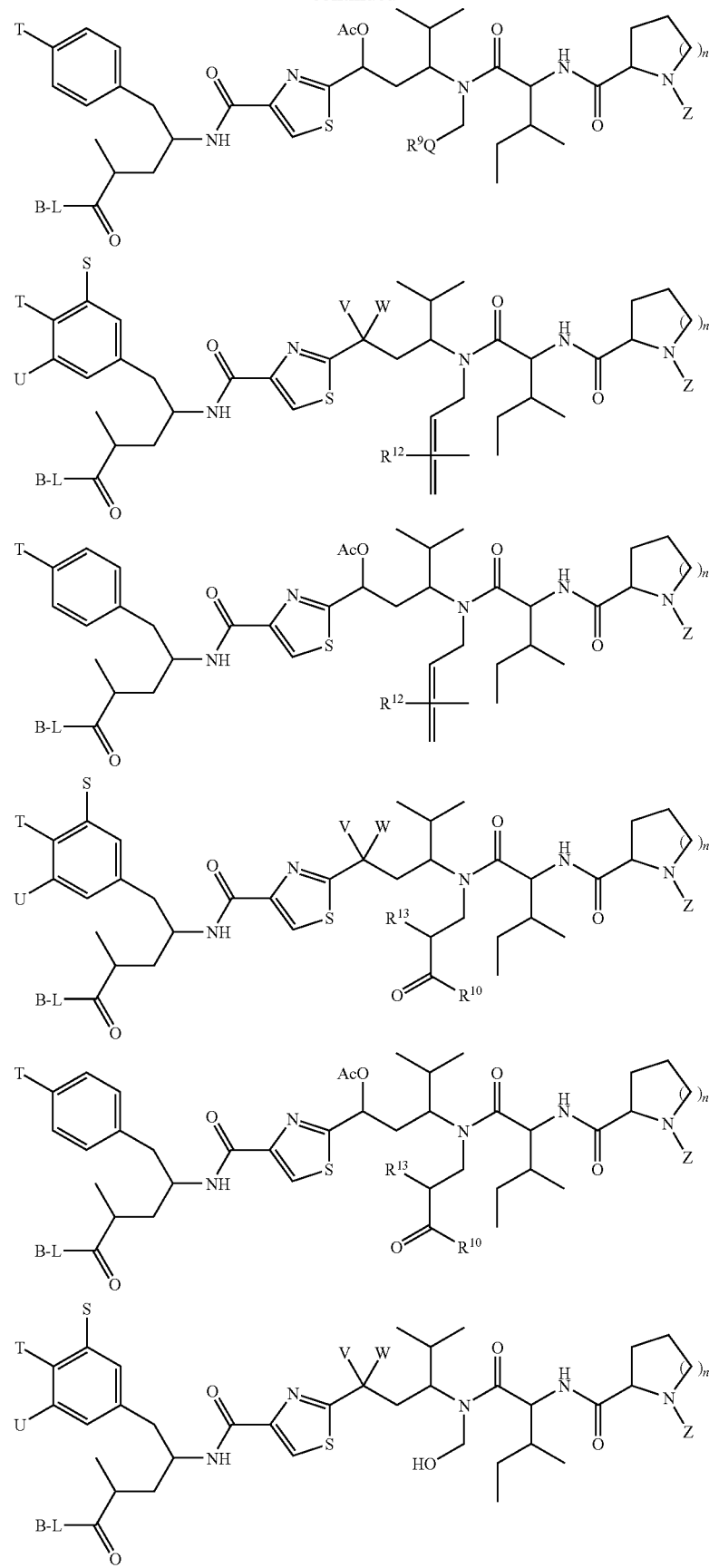

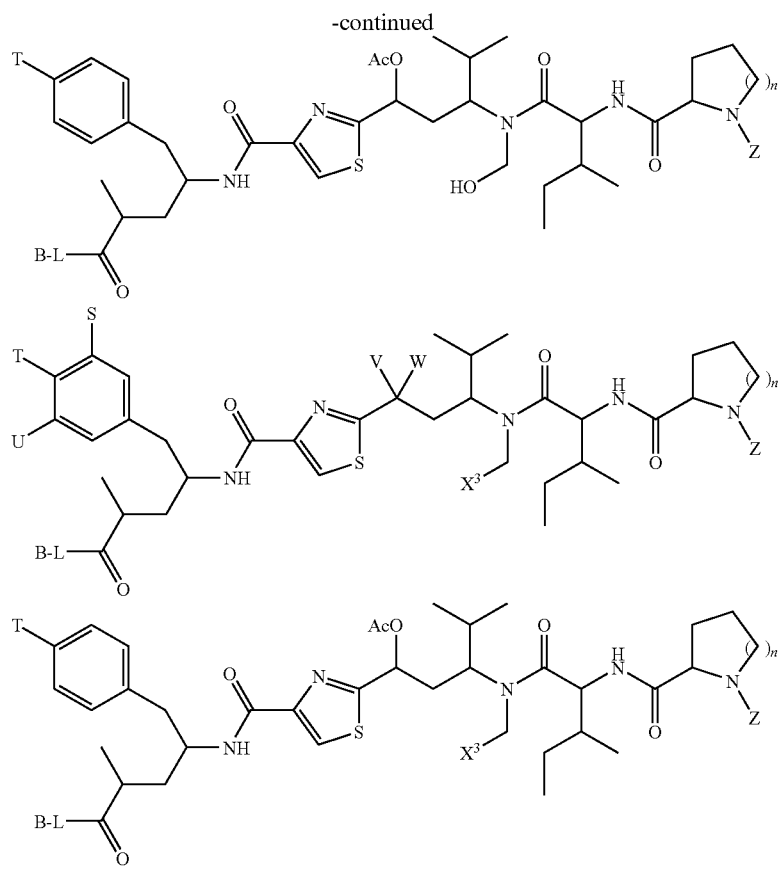

and pharmaceutical salts thereof, where B, L, n, S, T, U, V, W, X, Z, Q, $R^1$, $R^9$, $R^{10}$, $R^{12}$, $R^{13}$, and $X^3$ are as described herein in the various embodiments and aspects.

In another embodiment, illustrative carboxylic acid conjugate derivatives of naturally occurring tubulysins such as tubulysin A, tubulysin B, and tubulysin I, are described, and pharmaceutical salts thereof.

In another embodiment, illustrative carboxylic acid conjugate derivatives of the following tubulysin analogs and derivative are described Additional tubulysins that are useable in the conjugates described herein include the following, including the IC50 for inhibition of 3H thymidine update in 72 hour continuous assay of KB cells:

| Conjugate | $X^3$ |
|---|---|
| B-L-EC0313 | —O—$CH_3$ |
| B-L-EC0346 | —O—$(CH_2)_2$—OH |
| B-L-EC0356 | —O—$(CH_2)_2CH(CH_3)_2$ |
| B-L-EC0374 | —S—$(CH_2)_2$—SH |
| B-L-EC0386 | —OH |
| B-L-EC0550 | —$(CH_2)_2$—CH=$CH_2$ |
| B-L-EC0560 | —S—$(CH_2)_2$—OH |
| B-L-EC0575 | —O—C(O)—(CH=CH)—$CH_2$—Cl |
| B-L-EC0585 | —NH—C(O)—$CH_2CH(CH_3)_2$ |
| B-L-EC0611 | —O—$(CH_2)_2CH_3$ |
| B-L-EC0623 | —S—$(CH_2)_2CH_3$ | and pharmaceutical salts thereof.

As described herein, the tubulysin compounds may be inhibitors of tubulin polymerization, and also may be DNA-alkylators. Accordingly, methods for treating diseases and disease states including pathogenic cell populations, such as cancer, are contemplated herein.

In another embodiment, the bivalent linker (L) is a chain of atoms selected from C, N, O, S, Si, and P that covalently connects the binding ligand (B) to the tubulysin (D). The linker may have a wide variety of lengths, such as in the range from about 2 to about 100 atoms. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, such that for example, alkanes, alkenes, alkynes, imines, and the like may be radicals that are included in the linker. In addition, it is to be understood that the atoms forming the linker may also be cyclized upon each other to form divalent cyclic structures that form the linker, including cyclo alkanes, cyclic ethers, cyclic amines, arylenes, heteroarylenes, and the like in the linker.

In another embodiment, the linker includes radicals that form at least one releasable linker, and optionally one or more spacer linkers. As used herein, the term releasable linker refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH.

It is understood that a cleavable bond can connect two adjacent atoms within the releasable linker and/or connect other linkers or V and/or D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, a spacer linker, another releasable linker, the tubulysin, or analog or derivative thereof, or the binding ligand, following breakage of the bond, the releasable linker is separated from the other moiety. Accordingly, it is also understood that each of the spacer and releasable linkers are polyvalent, such as bivalent.

Illustrative releasable linkers include methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the releasable linker may include oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the releasable linker may include oxygen, and the releasable linker can be methylene, wherein the methylene is substituted with an optionally-substituted aryl, and the releasable linker is bonded to the oxygen to form an acetal or ketal. Further, the releasable linker may include oxygen, and the releasable linker can be sulfonylalkyl, and the releasable linker is bonded to the oxygen to form an alkylsulfonate.

In another embodiment of the above releasable linker embodiment, the releasable linker may include nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the releasable linker may include oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol. In another variation, the drug can include an oxygen atom, and the releasable linker can be haloalkylenecarbonyl, optionally substituted with a substituent $X^2$, and the releasable linker is bonded to the drug oxygen to form an ester.

In the above releasable linker embodiment, the drug can include a nitrogen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the drug nitrogen to form an amide. In one variation, the drug can include a nitrogen atom, and the releasable linker can be haloalkylenecarbonyl, optionally substituted with a substituent $X^2$, and the releasable linker is bonded to the drug nitrogen to form an amide. In another variation, the drug can include a double-bonded nitrogen atom, and in this embodiment, the releasable linkers can be alkylenecarbonylamino and 1-(alkylenecarbonylamino)succinimid-3-yl, and the releasable linker can be bonded to the drug nitrogen to form an hydrazone.

In another variation, the drug can include a sulfur atom, and in this embodiment, the releasable linkers can be alkylenethio and carbonylalkylthio, and the releasable linker can be bonded to the drug sulfur to form a disulfide. Alternatively, the drug can include an oxygen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the releasable linker can include nitrogen, and the substituent $X^2$ and the releasable linker can form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

In another embodiment, the bivalent linker (L) includes a disulfide releasable linker. In another embodiment, the bivalent linker (L) includes at least one releasable linker that is not a disulfide releasable linker.

In one aspect, the releasable and spacer linkers may be arranged in such a way that subsequent to the cleavage of a bond in the bivalent linker, released functional groups chemically assist the breakage or cleavage of additional bonds, also termed anchimeric assisted cleavage or breakage. An illustrative embodiment of such a bivalent linker or portion thereof includes compounds having the formulae:

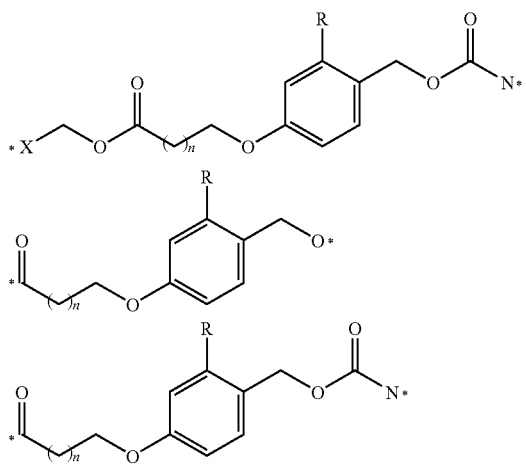

where X is an heteroatom, such as nitrogen, oxygen, or sulfur, or a carbonyl group; n is an integer selected from 0 to 4; illustratively 2; R is hydrogen, or a substituent, including a substituent capable of stabilizing a positive charge inductively or by resonance on the aryl ring, such as alkoxy and the like, including methoxy; and the symbol (*) indicates points of attachment for additional spacer, heteroatom, or releasable linkers forming the bivalent linker, or alternatively for attachment of the drug, or analog or derivative thereof, or the vitamin, or analog or derivative thereof. In one embodiment, n is 2 and R is methoxy. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

Illustrative examples of intermediates useful in forming such linkers include:

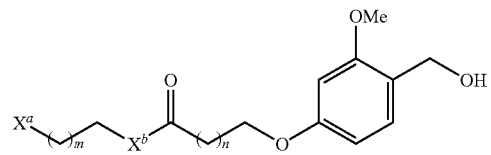

where $X^a$ is an electrophilic group such as maleimide, vinyl sulfone, activated carboxylic acid derivatives, and the like, $X^b$ is NH, O, or S; and m and n are each independently selected integers from 0-4. In one variation, m and n are each independently selected integers from 0-2. Such intermediates may be coupled to drugs, binding ligands, or other linkers vai nucleophilic attack onto electrophilic group $X^a$, and/or by forming ethers or carboxylic acid derivatives of the. In one embodiment, the benzylic hydroxyl group is converted into the corresponding activated benzyloxycarbonyl compound with phosgene or a phosgene equivalent. This embodiment may be coupled to drugs, binding ligands, or other linkers vai nucleophilic attack onto the activated carbonyl group.

The releasable linker includes at least one bond that can be broken or cleaved under physiological conditions (e.g., a pH-labile, acid-labile, oxidatively-labile, or enzyme-labile bond). The cleavable bond or bonds may be present in the interior of a cleavable linker and/or at one or both ends of a cleavable linker. It is appreciated that the lability of the cleavable bond may be adjusted by including functional groups or fragments within the bivalent linker L that are able to assist or facilitate such bond breakage, also termed anchimeric assistance. In addition, it is appreciated that additional functional groups or fragments may be included within the bivalent linker L that are able to assist or facilitate additional fragmentation of the vitamin receptor binding drug conjugates after bond breaking of the releasable linker.

The lability of the cleavable bond can be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like.

Illustrative mechanisms for cleavage of the bivalant linkers described herein include the following 1,4 and 1,6 fragmentation mechanisms

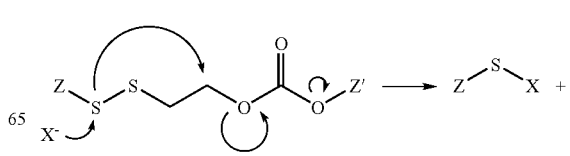

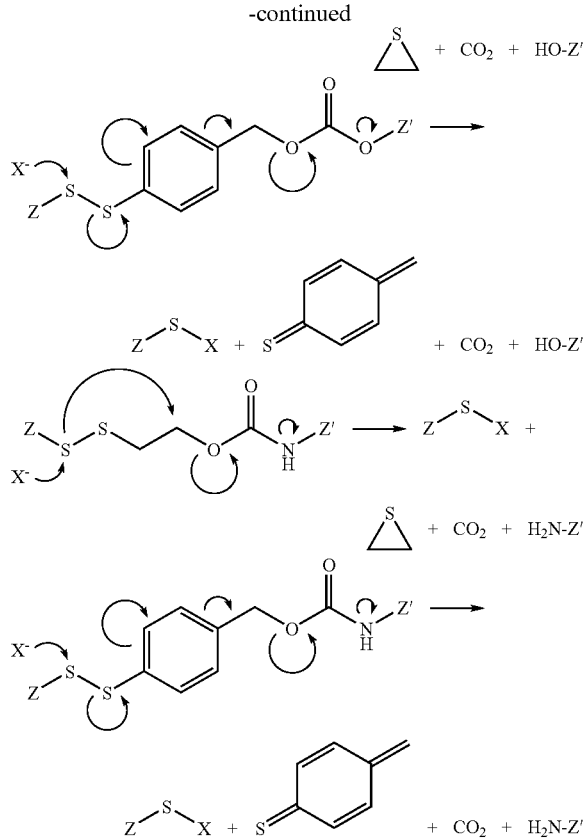

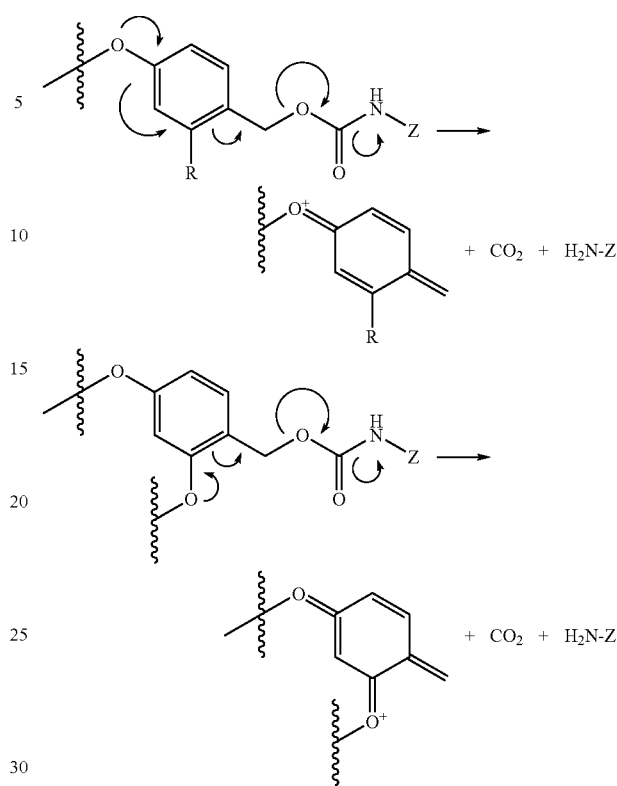

where X is an exogenous or endogenous nucleophile, glutathione, or bioreducing agent, and the like, and either of Z or Z' is the vitamin, or analog or derivative thereof, or the drug, or analog or derivative thereof, or a vitamin or drug moiety in conjunction with other portions of the polyvalent linker. It is to be understood that although the above fragmentation mechanisms are depicted as concerted mechanisms, any number of discrete steps may take place to effect the ultimate fragmentation of the polyvalent linker to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing polyvalent linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative polyvalent linkers described herein may be realized by whatever mechanism may be relevant to the chemical, metabolic, physiological, or biological conditions present.

Other illustrative mechanisms for bond cleavage of the releasable linker include oxonium-assisted cleavage as follows:

where Z is the vitamin, or analog or derivative thereof, or the drug, or analog or derivative thereof, or each is a vitamin or drug moiety in conjunction with other portions of the polyvalent linker, such as a drug or vitamin moiety including one or more spacer linkers and/or other releasable linkers. Without being bound by theory, in this embodiment, acid catalysis, such as in an endosome, may initiate the cleavage via protonation of the urethane group. In addition, acid-catalyzed elimination of the carbamate leads to the release of $CO_2$ and the nitrogen-containing moiety attached to Z, and the formation of a benzyl cation, which may be trapped by water, or any other Lewis base.

Other illustrative linkers include compounds of the formulae:

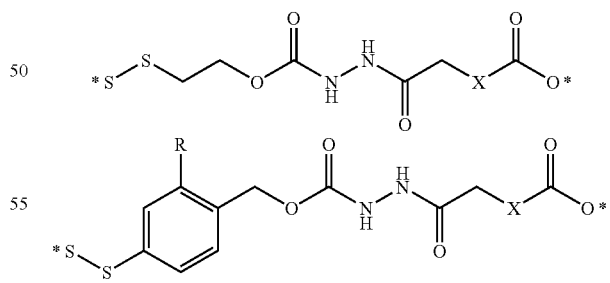

where X is NH, $CH_2$, or O; R is hydrogen, or a substituent, including a substituent capable of stabilizing a positive charge inductively or by resonance on the aryl ring, such as alkoxy and the like, including methoxy; and the symbol (*) indicates points of attachment for additional spacer, heteroatom, or releasable linkers forming the bivalent linker, or alternatively for attachment of the drug, or analog or derivative thereof, or the vitamin, or analog or derivative thereof.

Illustrative mechanisms for cleavage of such bivalent linkers described herein include the following 1,4 and 1,6 fragmentation mechanisms followed by anchimerically assisted cleavage of the acylated Z' via cyclization by the hydrazide group:

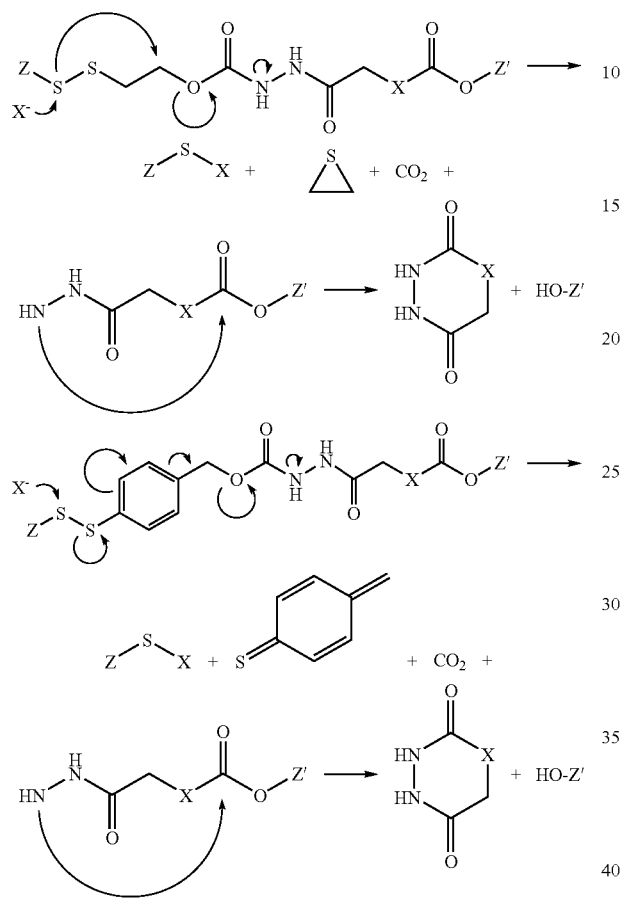

where X is an exogenous or endogenous nucleophile, glutathione, or bioreducing agent, and the like, and either of Z or Z' is the vitamin, or analog or derivative thereof, or the drug, or analog or derivative thereof, or a vitamin or drug moiety in conjunction with other portions of the polyvalent linker. It is to be understood that although the above fragmentation mechanisms are depicted as concerted mechanisms, any number of discrete steps may take place to effect the ultimate fragmentation of the polyvalent linker to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing polyvalent linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative polyvalent linkers described herein may be realized by whatever mechanism may be relevant to the chemical, metabolic, physiological, or biological conditions present. Without being bound by theory, in this embodiment, acid catalysis, such as in an endosome, may also initiate the cleavage via protonation of the urethane group. In addition, acid-catalyzed elimination of the carbamate leads to the release of $CO_2$ and the nitrogen-containing moiety attached to Z, and the formation of a benzyl cation, which may be trapped by water, or any other Lewis base, as is similarly described herein.

In one embodiment, the polyvalent linkers described herein are compounds of the following formulae

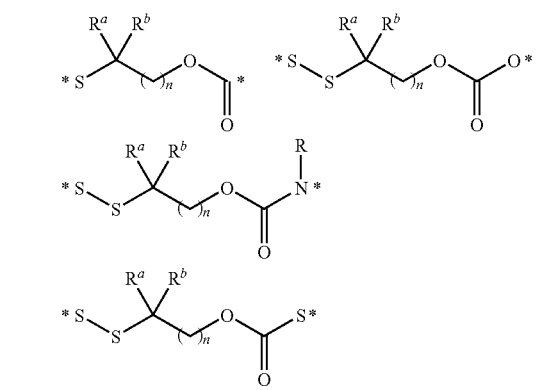

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein include compounds of the following formulae

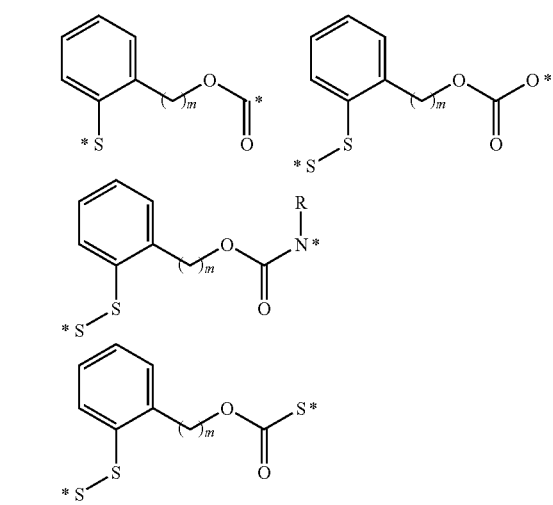

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein include compounds of the following formulae

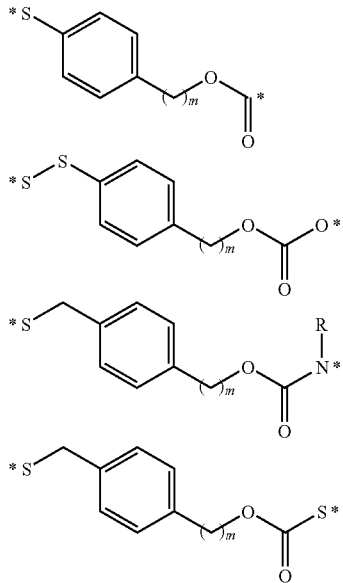

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

Another illustrative mechanism involves an arrangement of the releasable and spacer linkers in such a way that subsequent to the cleavage of a bond in the bivalent linker, released functional groups chemically assist the breakage or cleavage of additional bonds, also termed anchimeric assisted cleavage or breakage. An illustrative embodiment of such a bivalent linker or portion thereof includes compounds having the formula:

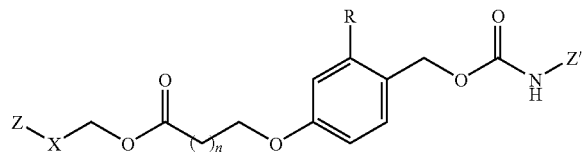

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and either of Z or Z' is the vitamin, or analog or derivative thereof, or the drug, or analog or derivative thereof, or a vitamin or drug moiety in conjunction with other portions of the bivalent linker. It is appreciated that other substituents may be present on the aryl ring, the benzyl carbon, the carbamate nittrogen, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragementation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative bivalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

In another embodiment, the releasable and spacer linkers may be arranged in such a way that subsequent to the cleavage of a bond in the polyvalent linker, released functional groups chemically assist the breakage or cleavage of additional bonds, also termed anchimeric assisted cleavage or breakage. An illustrative embodiment of such a polyvalent linker or portion thereof includes compounds having the formula:

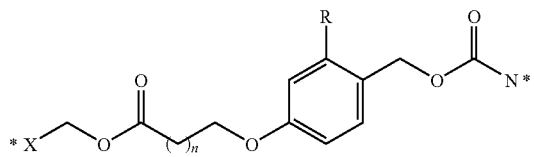

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer, heteroatom, or releasable linkers forming the polyvalent linker, or alternatively for attachment of the drug, or analog or derivative thereof, or the vitamin, or analog or derivative thereof. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

Another illustrative embodiment of the linkers described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

In another illustrative embodiment, the linker includes one or more amino acids. In one variation, the linker includes a single amino acid. In another variation, the linker includes a peptide having from 2 to about 50, 2 to about 30, or 2 to about 20 amino acids. In another variation, the linker includes a peptide having from about 4 to about 8 amino acids. Such amino acids are illustratively selected from the naturally occurring amino acids, or stereoisomers thereof. The amino acid may also be any other amino acid, such as any amino acid having the general formula:

—N(R)—(CR'R")$_q$—C(O)— where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like. In one variation, the releasable linker includes at least 2 amino acids selected from asparagine, aspartic acid, cysteine, glutamic acid, lysine, glutamine, arginine, serine, ornitine, and threonine. In another variation, the releasable linker includes between 2 and about 5 amino acids selected from asparagine, aspartic acid, cysteine, glutamic acid, lysine, glutamine, arginine, serine, ornitine, and threonine. In another variation, the releasable linker includes a tripeptide, tetrapeptide, pentapeptide, or hexapeptide consisting of amino acids selected from aspartic acid, cysteine, glutamic acid, lysine, arginine, and ornitine, and combinations thereof.

In another illustrative aspect of the vitamin receptor binding drug delivery conjugate intermediate described herein, the drug, or an analog or a derivative thereof, includes an alkylthiol nucleophile.

In another embodiment, the spacer linker can be 1-alkylenesuccinimid-3-yl, optionally substituted with a substituent $X^1$, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent $X^2$, as defined below, and wherein the spacer linker and the releasable linker are each bonded to the spacer linker to form a succinimid-1-ylalkyl acetal or ketal.

The spacer linkers can be carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the spacer linkers is optionally substituted with a substituent $X^1$, as defined below. In this embodiment, the spacer linker may include an additional nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and the spacer linker is bonded to the nitrogen to form an amide. Alternatively, the spacer linker may include an additional sulfur, and the spacer linkers can be alkylene and cycloalkylene, wherein each of the spacer linkers is optionally substituted with carboxy, and the spacer linker is bonded to the sulfur to form a thiol. In another embodiment, the spacer linker can include sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the spacer linker can include nitrogen, and the releasable linker can be a divalent radical comprising alkyleneaziridin-1-yl, carbonylalkylaziridin-1-yl, sulfoxylalkylaziridin-1-yl, or sulfonylalkylaziridin-1-yl, wherein each of the releasable linkers is optionally substituted with a substituent $X^2$, as defined below. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and wherein the spacer linker is bonded to the releasable linker to form an aziridine amide.

The substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the spacer linker can include nitrogen, and the substituent $X^1$ and the spacer linker to which they are bound to form an heterocycle.

In one aspect of the various vitamin receptor binding drug delivery conjugates described herein, the bivalent linker comprises an a spacer linker and a releasable linker taken together to form 3-thiosuccinimid-1-ylalkyloxymethyloxy, where the methyl is optionally substituted with alkyl or substituted aryl.

In another aspect, the bivalent linker comprises a spacer linker and a releasable linker taken together to form 3-thiosuccinimid-1-ylalkylcarbonyl, where the carbonyl forms an acylaziridine with the drug, or analog or derivative thereof.

In another aspect, the bivalent linker comprises an a spacer linker and a releasable linker taken together to form 1-alkoxycycloalkylenoxy.

In another aspect, the bivalent linker comprises a spacer linker and a releasable linker taken together to form alkyleneaminocarbonyl(dicarboxylarylene)carboxylate.

In another aspect, the bivalent linker comprises a releasable linker, a spacer linker, and a releasable linker taken together to form 2- or 3-dithioalkylcarbonylhydrazide, where the hydrazide forms an hydrazone with the drug, or analog or derivative thereof.

In another aspect, the bivalent linker comprises a spacer linker and a releasable linker taken together to form 3-thiosuccinimid-1-ylalkylcarbonylhydrazide, where the hydrazide forms an hydrazone with the drug, or analog or derivative thereof.

In another aspect, the bivalent linker comprises a spacer linker and a releasable linker taken together to form 2- or 3-thioalkylsulfonylalkyl(disubstituted silyl)oxy, where the disubstituted silyl is substituted with alkyl or optionally substituted aryl.

In another aspect, the bivalent linker comprises a plurality of spacer linkers selected from the group consisting of the naturally occurring amino acids and stereoisomers thereof.

In another aspect, the bivalent linker comprises a releasable linker, a spacer linker, and a releasable linker taken together to form 3-dithioalkyloxycarbonyl, where the carbonyl forms a carbonate with the drug, or analog or derivative thereof.

In another aspect, the bivalent linker comprises a releasable linker, a spacer linker, and a releasable linker taken together to form 3-dithioarylalkyloxycarbonyl, where the carbonyl forms a carbonate with the drug, or analog or derivative thereof, and the aryl is optionally substituted.

In another aspect, the bivalent linker comprises a spacer linker and a releasable linker taken together to form 3-thiosuccinimid-1-ylalkyloxyalkyloxyalkylidene, where the alkylidene forms an hydrazone with the drug, or analog or derivative thereof, each alkyl is independently selected, and the oxyalkyloxy is optionally substituted with alkyl or optionally substituted aryl.

In another aspect, the bivalent linker comprises a releasable linker, a spacer linker, and a releasable linker taken together to form 2- or 3-dithioalkyloxycarbonylhydrazide.

In another aspect, the bivalent linker comprises a releasable linker, a spacer linker, and a releasable linker taken together to form 2- or 3-dithioalkylamino, where the amino forms a vinylogous amide with the drug, or analog or derivative thereof.

In another aspect, the bivalent linker comprises a releasable linker, a spacer linker, and a releasable linker taken together to form 2- or 3-dithioalkylamino, where the amino forms a vinylogous amide with the drug, or analog or derivative thereof, and the alkyl is ethyl.

In another aspect, the bivalent linker comprises a releasable linker, a spacer linker, and a releasable linker taken together to form 2- or 3-dithioalkylaminocarbonyl, where the carbonyl forms a carbamate with the drug, or analog or derivative thereof.

In another aspect, the bivalent linker comprises a releasable linker, a spacer linker, and a releasable linker taken together to form 2- or 3-dithioalkylaminocarbonyl, where the carbonyl forms a carbamate with the drug, or analog or derivative thereof, and the alkyl is ethyl.

In another aspect, the bivalent linker comprises a releasable linker, a spacer linker, and a releasable linker taken together to form 2- or 3-dithioarylalkyloxycarbonyl, where the carbonyl forms a carbamate or a carbamoylaziridine with the drug, or analog or derivative thereof.

In another embodiment, the polyvalent linker includes spacer linkers and releasable linkers connected to form a polyvalent 3-thiosuccinimid-1-ylalkyloxymethyloxy group, illustrated by the following formula

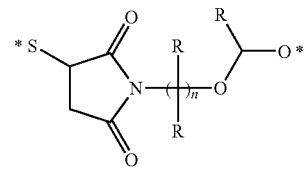

where n is an integer from 1 to 6, the alkyl group is optionally substituted, and the methyl is optionally substituted with an additional alkyl or optionally substituted aryl group, each of which is represented by an independently selected group R. The (*) symbols indicate points of attachment of the polyvalent linker fragment to other parts of the conjugates described herein.

In another embodiment, the polyvalent linker includes spacer linkers and releasable linkers connected to form a polyvalent 3-thiosuccinimid-1-ylalkylcarbonyl group, illustrated by the following formula

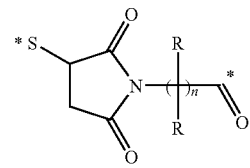

where n is an integer from 1 to 6, and the alkyl group is optionally substituted. The (*) symbols indicate points of attachment of the polyvalent linker fragment to other parts of the conjugates described herein. In another embodiment, the polyvalent linker includes spacer linkers and releasable linkers connected to form a polyvalent 3-thioalkylsulfonylalkyl(disubstituted silyl)oxy group, where the disubstituted silyl is substituted with alkyl and/or optionally substituted aryl groups.

In another embodiment, the polyvalent linker includes spacer linkers and releasable linkers connected to form a polyvalent dithioalkylcarbonylhydrazide group, or a polyvalent 3-thiosuccinimid-1-ylalkylcarbonylhydrazide, illustrated by the following formulae

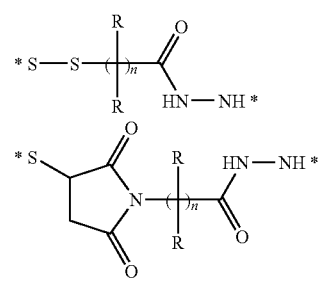

where n is an integer from 1 to 6, the alkyl group is optionally substituted, and the hydrazide forms an hydrazone with (B), (D), or another part of the polyvalent linker (L). The (*) symbols indicate points of attachment of the polyvalent linker fragment to other parts of the conjugates described herein.

In another embodiment, the polyvalent linker includes spacer linkers and releasable linkers connected to form a polyvalent 3-thiosuccinimid-1-ylalkyloxyalkyloxyalkylidene group, illustrated by the following formula

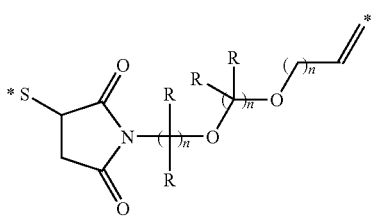

where each n is an independently selected integer from 1 to 6, each alkyl group independently selected and is optionally substituted, such as with alkyl or optionally substituted aryl, and where the alkylidene forms an hydrazone with (B), (D), or another part of the polyvalent linker (L). The (*) symbols indicate points of attachment of the polyvalent linker fragment to other parts of the conjugates described herein.

Additional illustrative spacer linkers include alkylene-amino-alkylenecarbonyl, alkylene-thio-carbonylalkylsuccinimid-3-yl, and the like, as further illustrated by the following formulae:

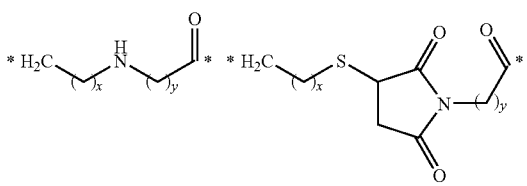

where the integers x and y are 1, 2, 3, 4, or 5:

The term cycloalkylene as used herein refers to a bivalent chain of carbon atoms, a portion of which forms a ring, such as cycloprop-1,1-diyl, cycloprop-1,2-diyl, cyclohex-1,4-diyl, 3-ethylcyclopent-1,2-diyl, 1-methylenecyclohex-4-yl, and the like.

The term heterocycle as used herein refers to a monovalent chain of carbon and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like.

The term aryl as used herein refers to an aromatic mono or polycyclic ring of carbon atoms, such as phenyl, naphthyl, and the like. In addition, aryl may also include heteroaryl.

The term heteroaryl as used herein refers to an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term optionally substituted as used herein refers to the replacement of one or more hydrogen atoms, generally on carbon, with a corresponding number of substituents, such as halo, hydroxy, amino, alkyl or dialkylamino, alkoxy, alkylsulfonyl, cyano, nitro, and the like. In addition, two hydrogens on the same carbon, on adjacent carbons, or nearby carbons may be replaced with a bivalent substituent to form the corresponding cyclic structure.

The term iminoalkylidenyl as used herein refers to a divalent radical containing alkylene as defined herein and a nitrogen atom, where the terminal carbon of the alkylene is double-bonded to the nitrogen atom, such as the formulae —(CH)=N—, —(CH$_2$)$_2$(CH)=N—, —CH$_2$C(Me)=N—, and the like.

The term amino acid as used herein refers generally to aminoalkylcarboxylate, where the alkyl radical is optionally substituted, such as with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like. It is to be understood that such amino acids may be of a single stereochemistry or a particular mixture of stereochemisties, including racemic mixtures. In addition, amino acid refers to beta, gamma, and longer amino acids, such as amino acids of the formula:

—N(R)—(CR'R")$_q$—C(O)— where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like. In another illustrative aspect of the vitamin receptor binding drug delivery conjugate intermediate described herein, the drug, or an analog or a derivative thereof, includes an alkylthiol nucleophile.

It is to be understood that the above-described terms can be combined to generate chemically-relevant groups, such as alkoxyalkyl referring to methyloxymethyl, ethyloxyethyl, and the like, haloalkoxyalkyl referring to trifluoromethyloxyethyl, 1,2-difluoro-2-chloroeth-1-yloxypropyl, and the like, arylalkyl referring to benzyl, phenethyl, α-methylbenzyl, and the like, and others.

The term amino acid derivative as used herein refers generally to an optionally substituted aminoalkylcarboxylate, where the amino group and/or the carboxylate group are each optionally substituted, such as with alkyl, carboxylalkyl, alkylamino, and the like, or optionally protected. In addition, the optionally substituted intervening divalent alkyl fragment may include additional groups, such as protecting groups, and the like.

The term peptide as used herein refers generally to a series of amino acids and/or amino acid analogs and derivatives covalently linked one to the other by amide bonds.

Additional linkers are described in U.S. patent application publication 2005/0002942, the disclosure of which is incorporated herein by reference, and in Tables 1 and 2 below, where the (*) atom is the point of attachment of additional spacer or releaseable linkers, the drug, and/or the binding ligand.

TABLE 1

Illustrative spacer linkers.

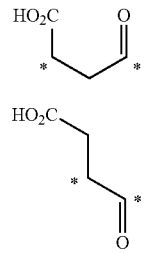

TABLE 1-continued
Illustrative spacer linkers.
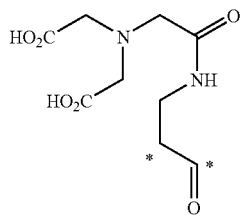 [SMILES: O=CCCNC(=O)CN(CC(=O)O)CC(=O)O]
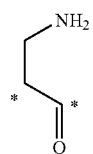
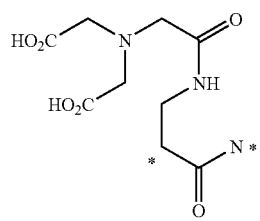 [SMILES: NC(=O)CCNC(=O)CN(CC(=O)O)CC(=O)O]
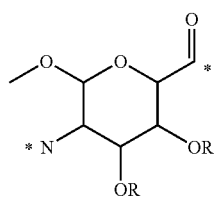
R = H, alkyl, acyl
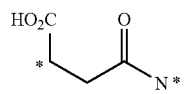
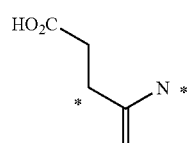
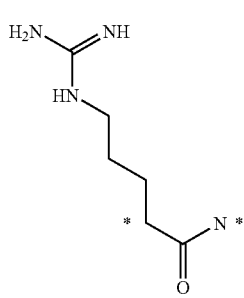
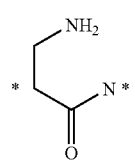
TABLE 1-continued
Illustrative spacer linkers.
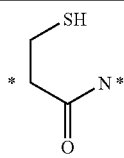
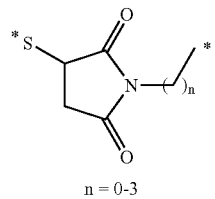
n = 0-3
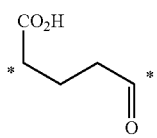
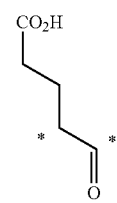
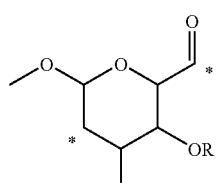
R = H, alkyl, acyl
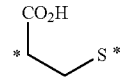
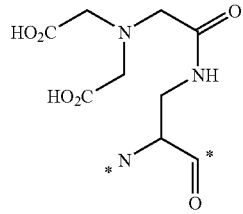 [SMILES: NC(C=O)CNC(=O)CN(CC(=O)O)CC(=O)O]
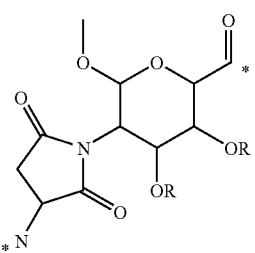
R = H, alkyl, acyl TABLE 1-continued
Illustrative spacer linkers.
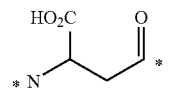
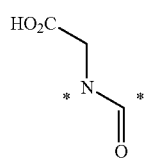
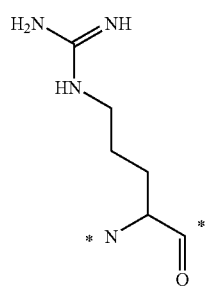 [SMILES: N=C(N)NCCCC(N)C=O]
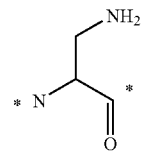
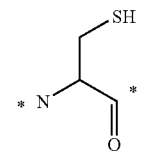
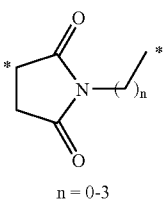
n = 0-3
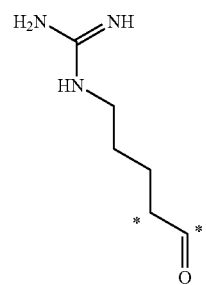
TABLE 1-continued
Illustrative spacer linkers.
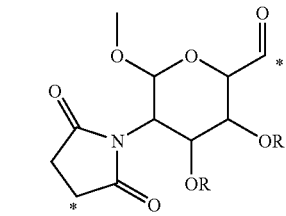
R = H, alkyl, acyl
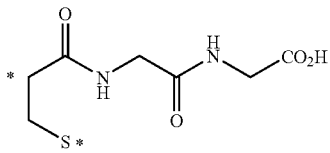 [SMILES: O=C(O)CNC(=O)CNC(=O)CCS]
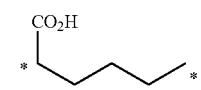
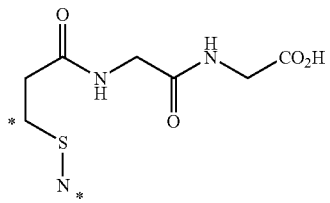 [SMILES: NSCCC(=O)NCC(=O)NCC(=O)O]
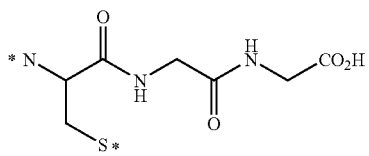 [SMILES: NC(CS)C(=O)NCC(=O)NCC(=O)O]
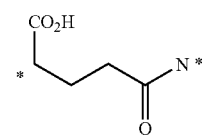
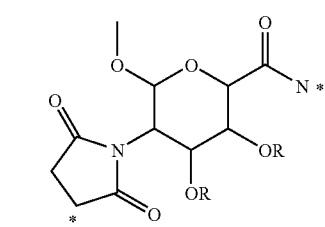
R = H, alkyl, acyl
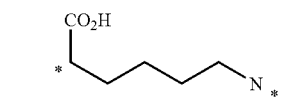
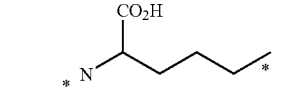

TABLE 1-continued
Illustrative spacer linkers.
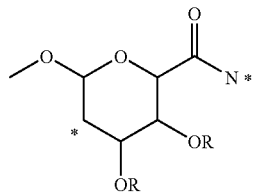
R = H, alkyl, acyl
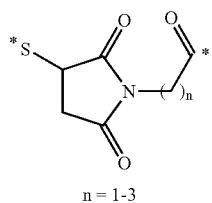
n = 1-3
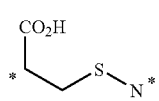
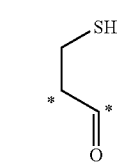
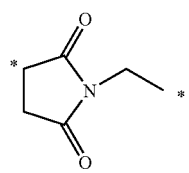
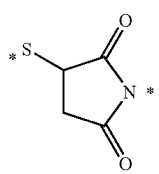
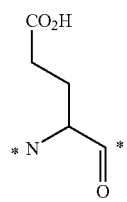
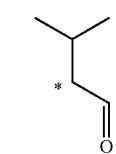
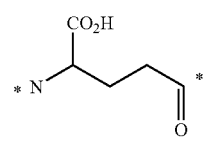
TABLE 1-continued
Illustrative spacer linkers.
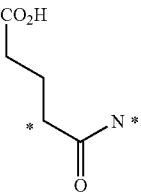
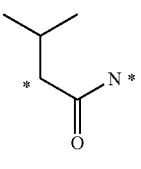
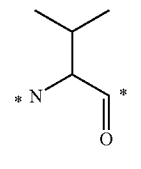
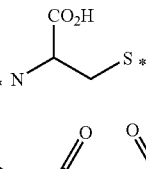
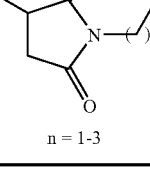
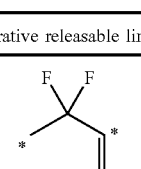
n = 1-3
TABLE 2
Illustrative releasable linkers.
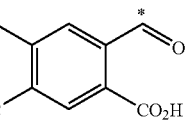
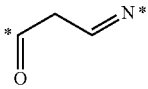
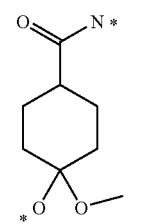

TABLE 2-continued
Illustrative releasable linkers.
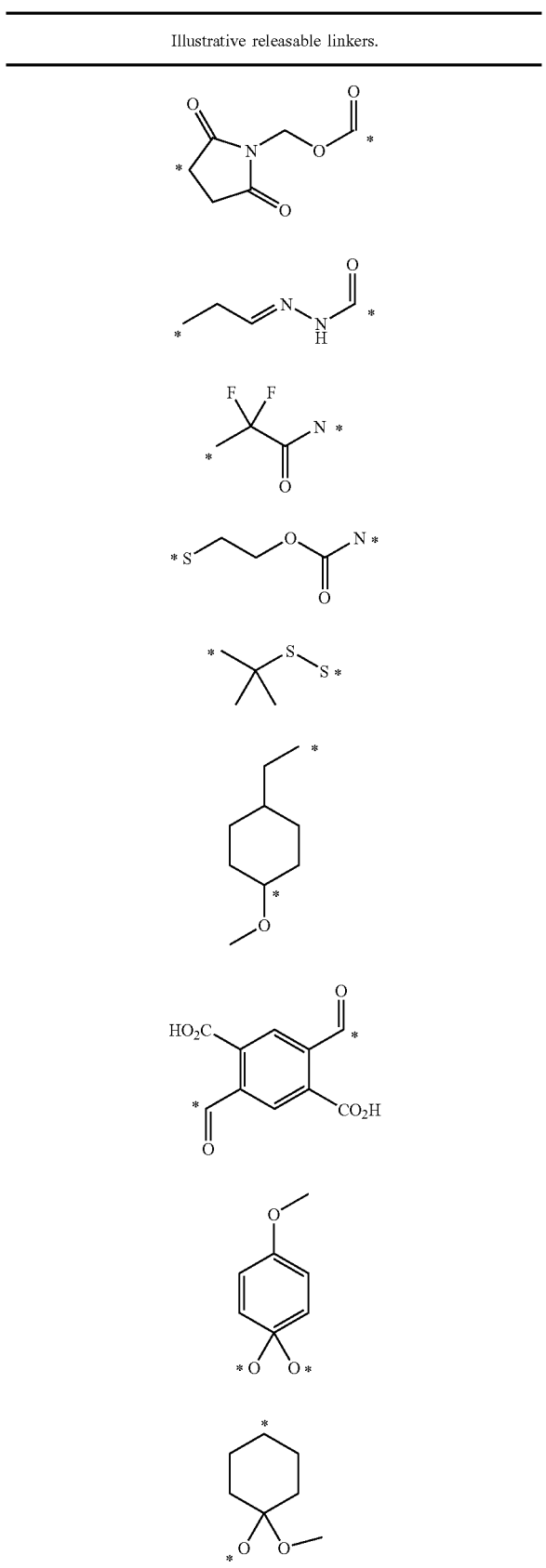
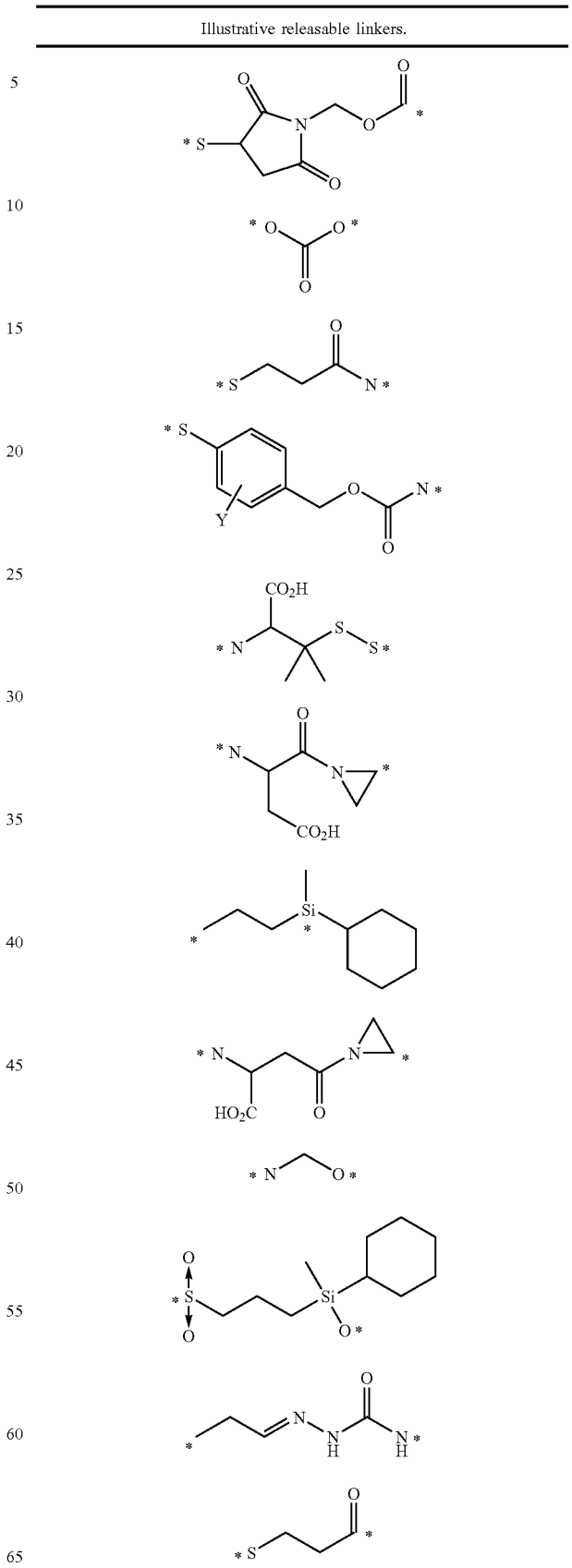

TABLE 2-continued

Illustrative releasable linkers.

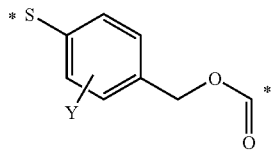

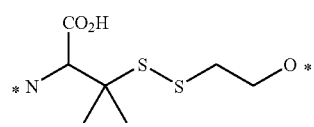

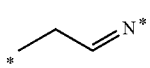

TABLE 2-continued

Illustrative releasable linkers.

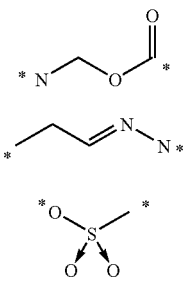

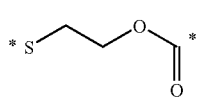

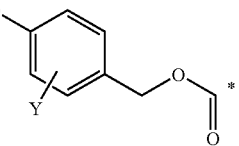

In another illustrative embodiment, bivalent linkers (L) that include spacer linkers that substantially increase the water solubility, biological transport, preferential renal clearance, uptake, absorption, biodistribution, and/or bioavailability of the conjugate are described herein. Illustrative spacer linkers that include hydrophilic groups are described, such as compounds of the formula

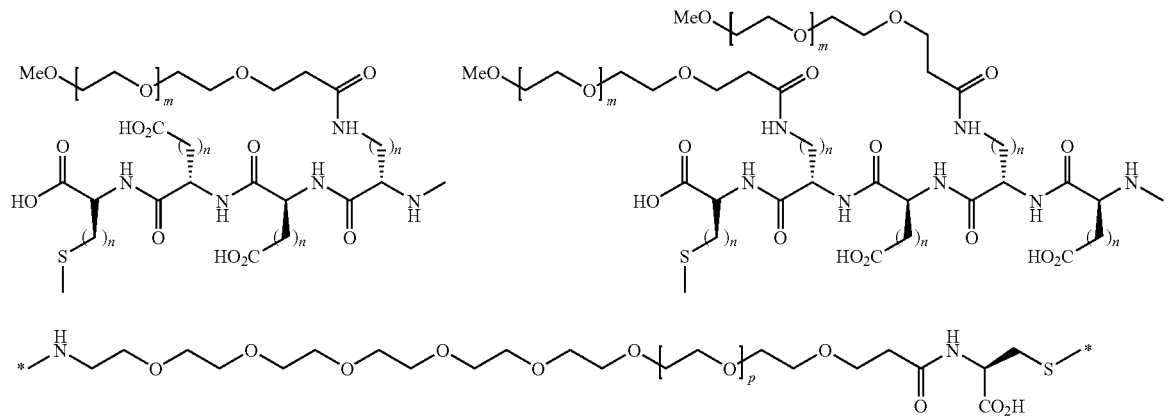

where m is an integer independently selected in each instance from 1 to about 8; p is an integer selected 1 to about 10; and n is an integer independently selected in each instance from 1 to about 3. In one aspect, m is independently in each instance 1 to about 3. In another aspect, n is 1 in each instance. In another aspect, p is independently in each instance about 4 to about 6. Illustratively, the corresponding polypropylene polyethers corresponding to the foregoing are contemplated herein and may be included in the conjugates as hydrophilic spacer linkers. In addition, it is appreciated that mixed polyethylene and polypropylene polyethers may be included in the conjugates as hydrophilic spacer linkers. Further, cyclic variations of the foregoing polyether com- TABLE 2-continued Illustrative releasable linkers.

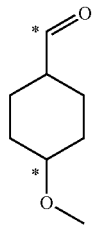

pounds, such as those that include tetrahydrofuranyl, 1,3-dioxanes, 1,4-dioxanes, and the like are contemplated herein.

In another illustrative embodiment, the hydrophilic spacer linkers described herein include a plurality of hydroxyl functional groups, such as linkers that incorporate monosaccharides, oligosaccharides, polysaccharides, and the like. It is to be understood that the polyhydroxyl containing spacer linkers comprises a plurality of —(CROH)— groups, where R is hydrogen or alkyl.

In another embodiment, the spacer linkers include one or more of the following fragments:

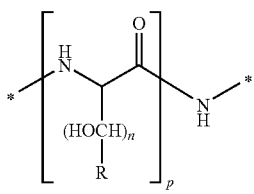

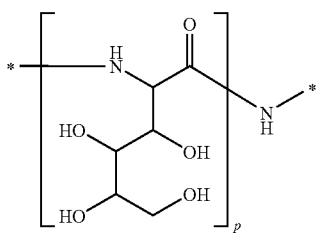

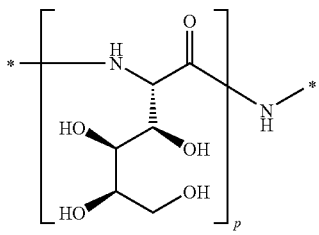

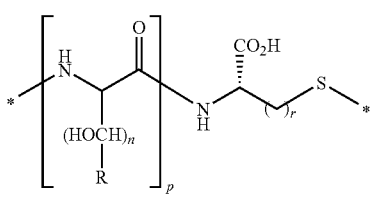

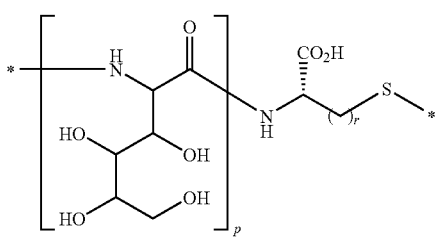

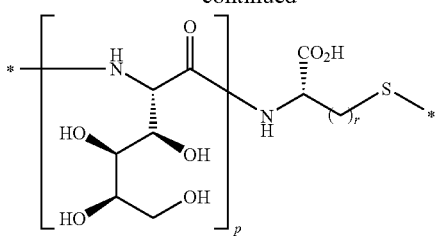

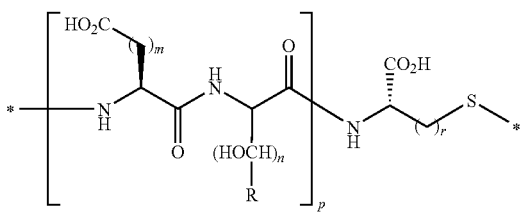

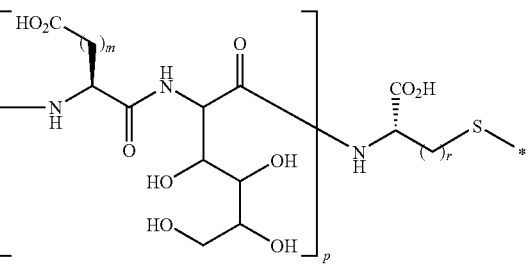

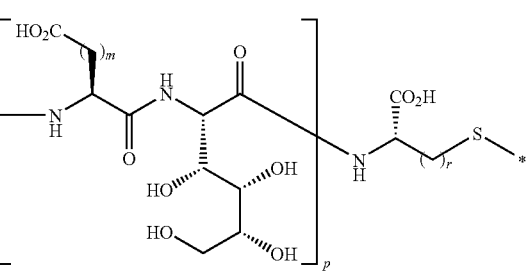

wherein R is H, alkyl, cycloalkyl, or arylalkyl; m is an integer from 1 to about 3; n is an integer from 1 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the spacer linkers include one or more of the following fragments:

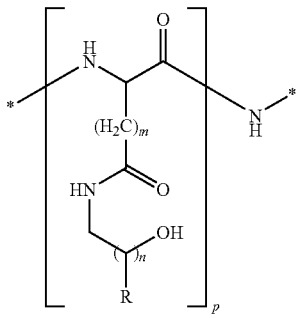

53
-continued
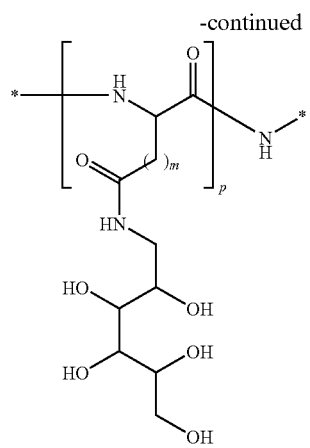
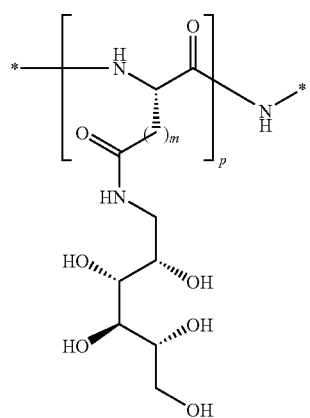
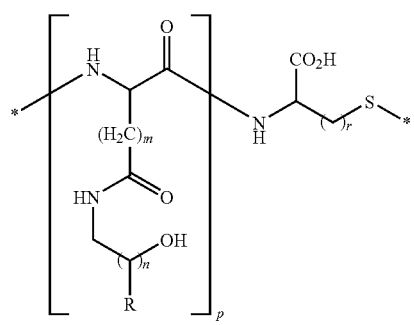
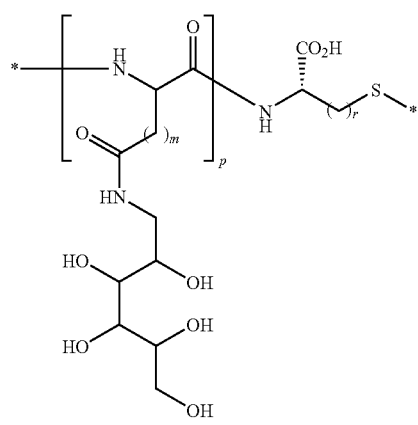
54
-continued
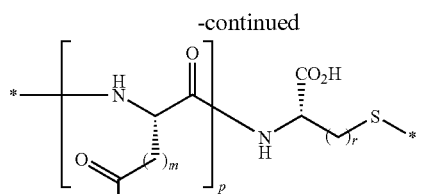
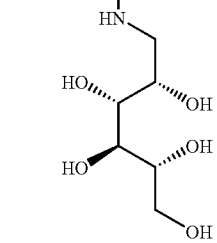
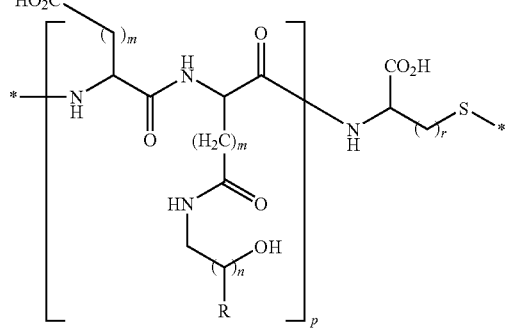
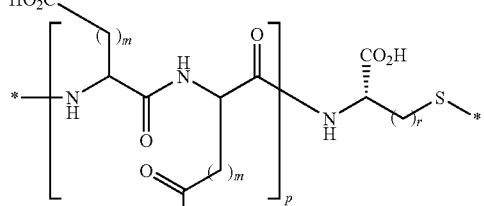
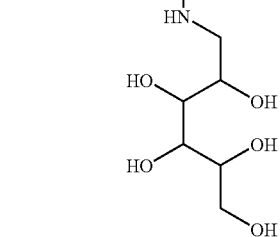
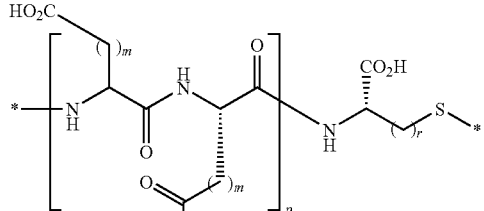
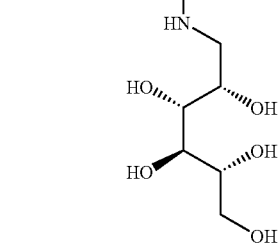

wherein R is H, alkyl, cycloalkyl, or arylalkyl; m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the spacer linker includes one or more of the following cyclic polyhydroxyl groups:

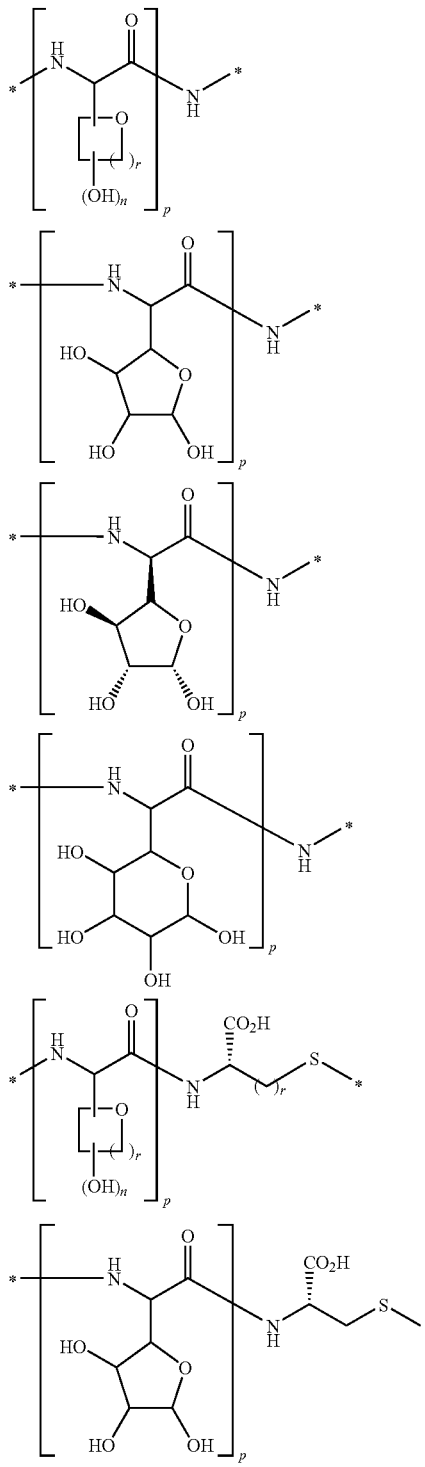
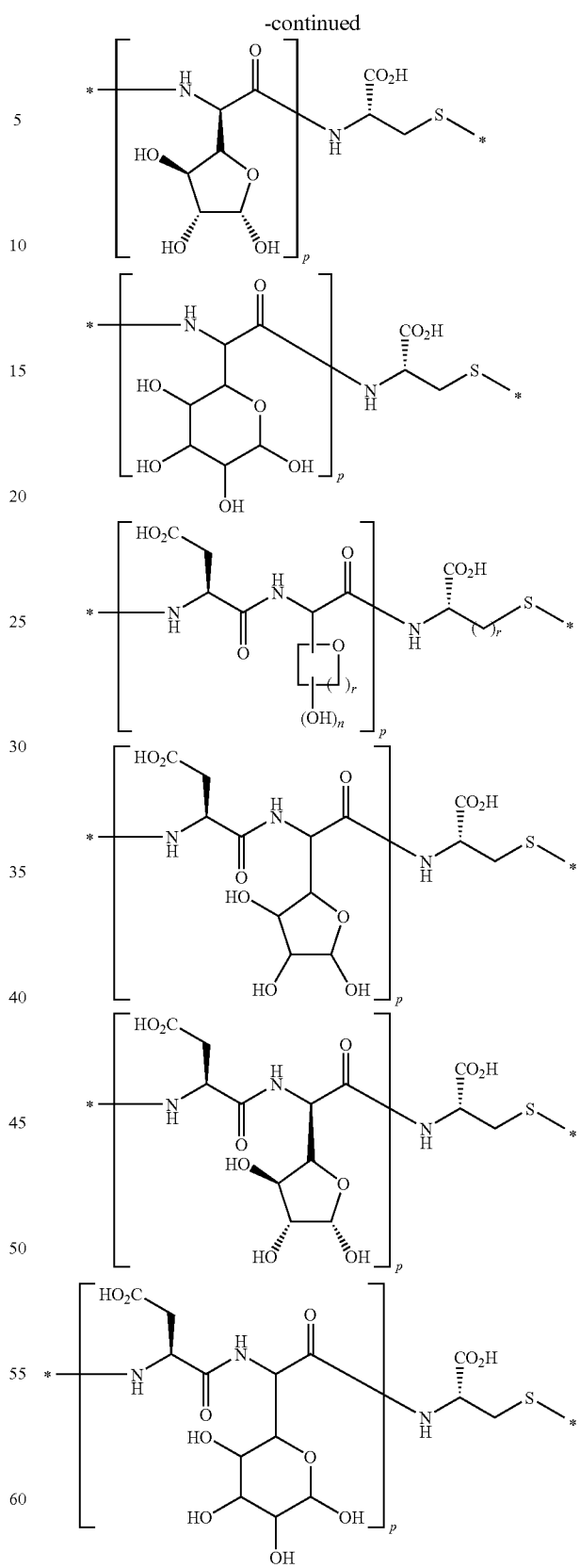

wherein n is an integer from 2 to about 5, p is an integer from 1 to about 5, and r is an integer from 1 to about 4. In one aspect, the integer n is 3 or 4. In another aspect, the integer p is 3 or 4. In another aspect, the integer r is 2 or 3. It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also contemplated. Illustratively, compounds of the following formulae are contemplated:

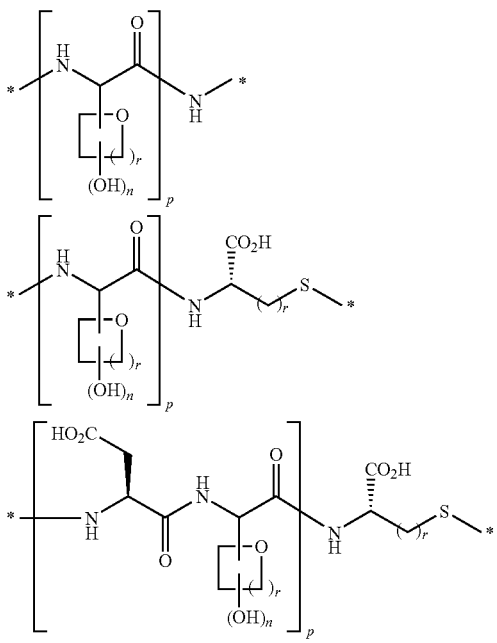

wherein n is equal to or less than r, such as when r is 2 or 3, n is 1 or 2, or 1, 2, or 3, respectively.

In another embodiment, the spacer linker includes a polyhydroxyl compound of the following formula:

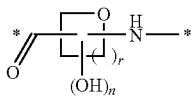

wherein n and r are each an integer selected from 1 to about 3. In one aspect, the spacer linker includes one or more polyhydroxyl compounds of the following formulae:

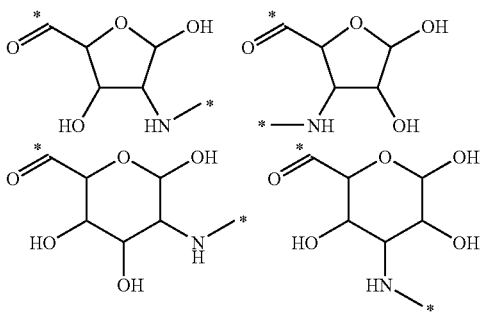

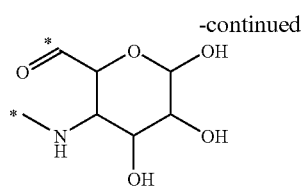

It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules.

In another configuration, the hydrophilic linkers L described herein include polyhydroxyl groups that are spaced away from the backbone of the linker. Illustratively, such linkers include fragments of the following formulae:

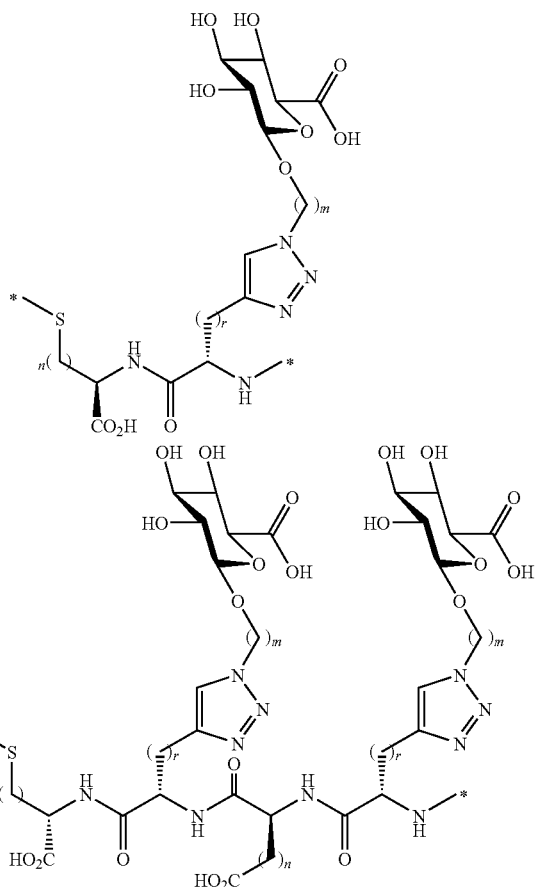

wherein n, m, and r are integers and are each independently selected in each instance from 1 to about 5. In one illustrative aspect, m is independently 2 or 3 in each instance. In another aspect, r is 1 in each instance. In another aspect, n is 1 in each instance. In one variation, the group connecting the polyhydroxyl group to the backbone of the linker is a different heteroaryl group, including but not limited to, pyrrole, pyrazole, 1,2,4-triazole, furan, oxazole, isoxazole, thienyl, thiazole, isothiazole, oxadiazole, and the like. Similarly, divalent 6-membered ring heteroaryl groups are contemplated. Other variations of the foregoing illustrative hydrophilic spacer linkers include oxyalkylene groups, such as the following formulae:

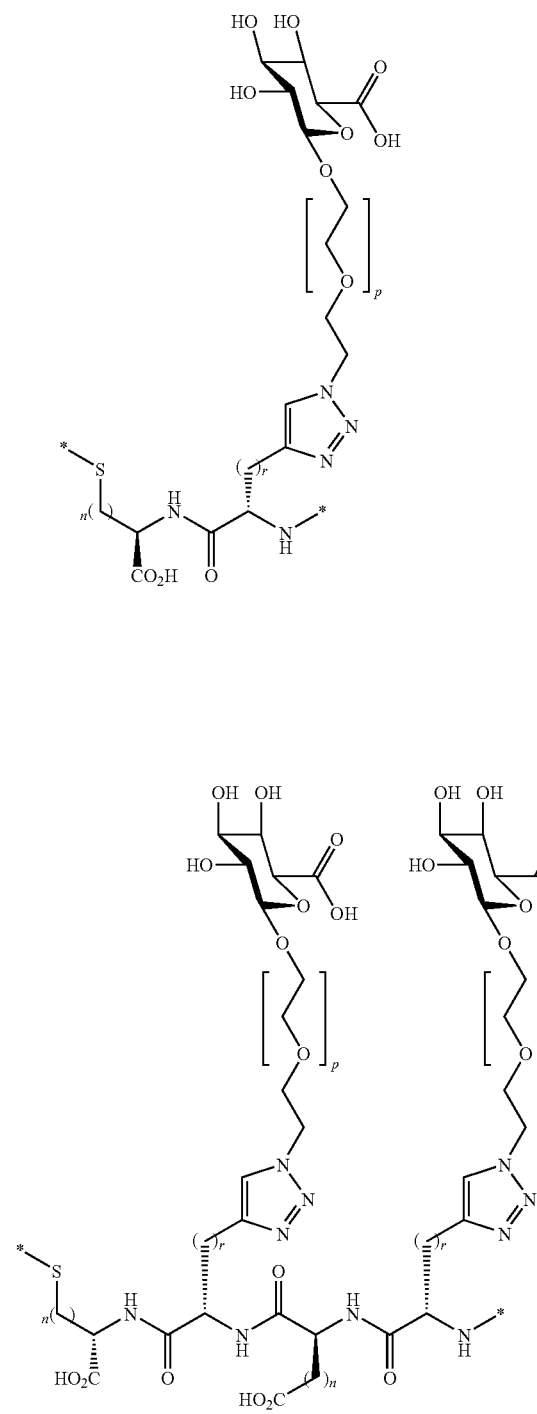

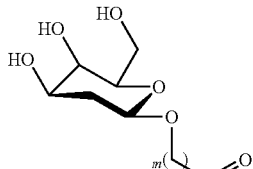

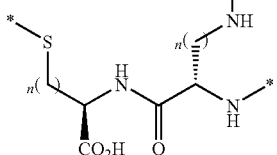

wherein n and r are integers and are each independently selected in each instance from 1 to about 5; and p is an integer selected from 1 to about 4.

In another embodiment, the hydrophilic linkers L described herein include polyhydroxyl groups that are spaced away from the backbone of the linker. Illustratively, such linkers include fragments of the following formulae:

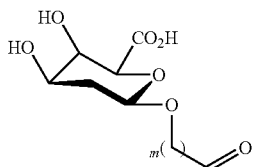

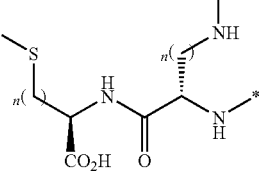

wherein n is an integer selected from 1 to about 3, and m is an integer selected from 1 to about 22. In one illustrative aspect, n is 1 or 2. In another illustrative aspect, m is selected from about 6 to about 10, illustratively 8. In one variation, the group connecting the polyhydroxyl group to the backbone of the linker is a different functional group, including but not limited to, esters, ureas, carbamates, acylhydrazones, and the like. Similarly, cyclic variations are contemplated. Other variations of the foregoing illustrative hydrophilic spacer linkers include oxyalkylene groups, such as the following formulae:

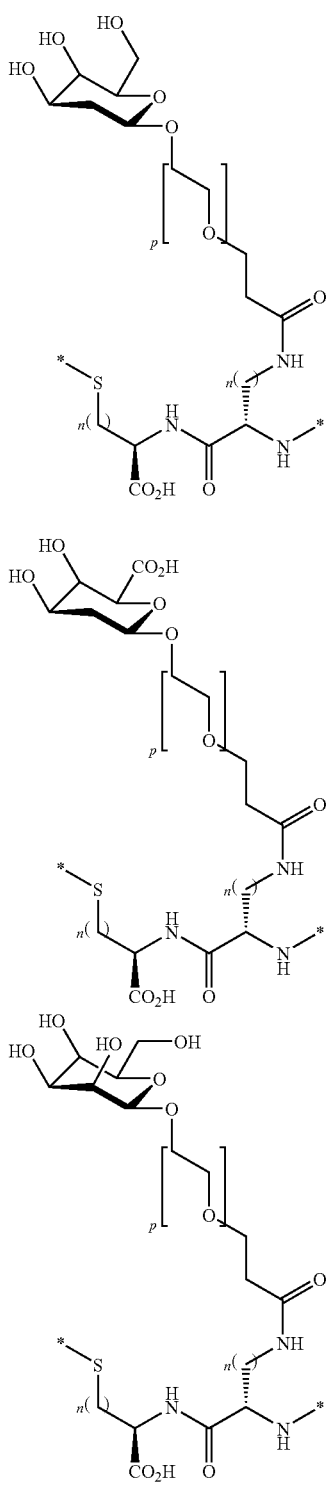

wherein n and r are integers and are each independently selected in each instance from 1 to about 5; and p is an integer selected from 1 to about 4.

In another embodiment, the hydrophilic spacer linker is a combination of backbone and branching side motifs such as is illustrated by the following formulae

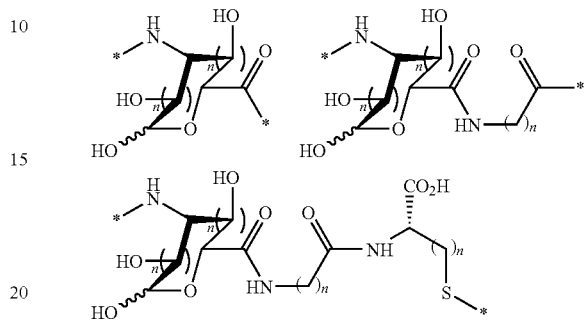

wherein n is an integer independently selected in each instance from 0 to about 3. The above formula are intended to represent 4, 5, 6, and even larger membered cyclic sugars. In addition, it is to be understood that the above formula may be modified to represent deoxy sugars, where one or more of the hydroxy groups present on the formulae are replaced by hydrogen, alkyl, or amino. In addition, it is to be understood that the corresponding carbonyl compounds are contemplated by the above formulae, where one or more of the hydroxyl groups is oxidized to the corresponding carbonyl. In addition, in this illustrative embodiment, the pyranose includes both carboxyl and amino functional groups and (a) can be inserted into the backbone and (b) can provide synthetic handles for branching side chains in variations of this embodiment. Any of the pendant hydroxyl groups may be used to attach other chemical fragments, including additional sugars to prepare the corresponding oligosaccharides. Other variations of this embodiment are also contemplated, including inserting the pyranose or other sugar into the backbone at a single carbon, i.e. a spiro arrangement, at a geminal pair of carbons, and like arrangements. For example, one or two ends of the linker, or the agent A, or the binding ligand B may be connected to the sugar to be inserted into the backbone in a 1,1; 1,2; 1,3; 1,4; 2,3, or other arrangement.

In another embodiment, the hydrophilic spacer linkers described herein include are formed primarily from carbon, hydrogen, and nitrogen, and have a carbon/nitrogen ratio of about 3:1 or less, or of about 2:1 or less. In one aspect, the hydrophilic linkers described herein include a plurality of amino functional groups.

In another embodiment, the spacer linkers include one or more amino groups of the following formulae:

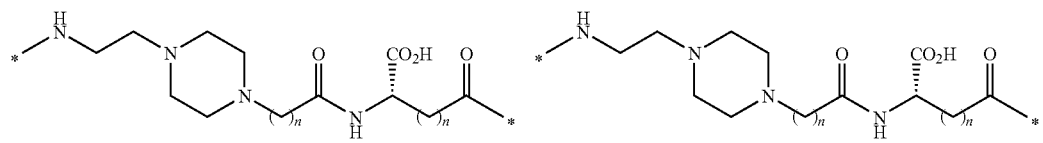

-continued
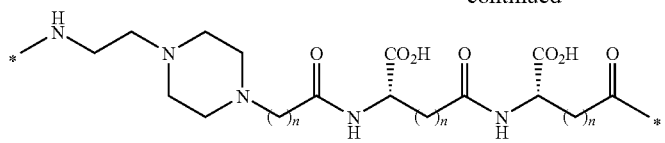
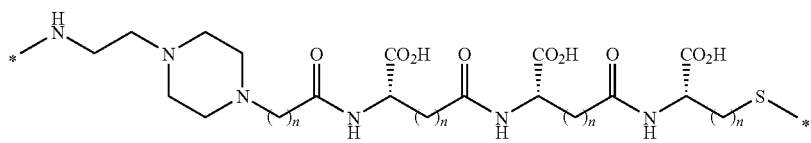
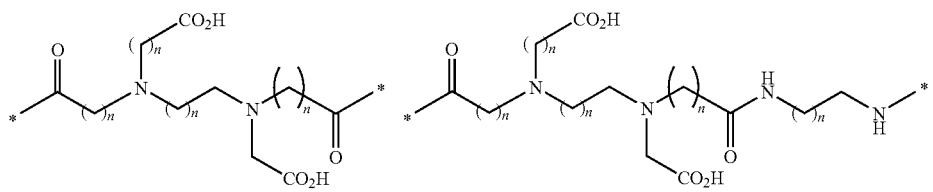
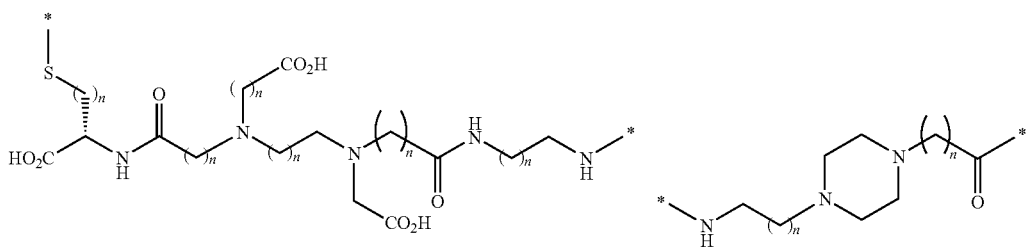
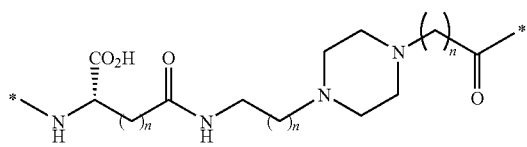
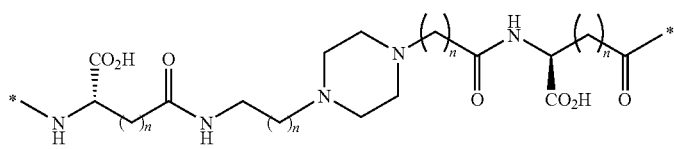
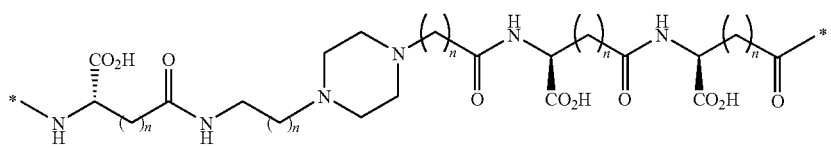
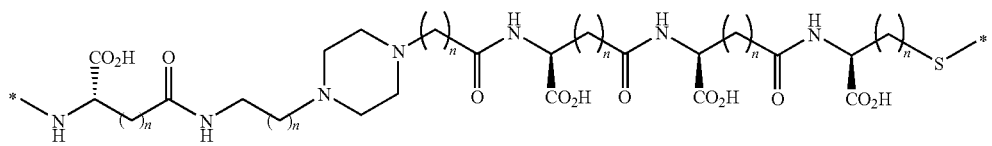

where n is an integer independently selected in each instance from 1 to about 3. In one aspect, the integer n is independently 1 or 2 in each instance. In another aspect, the integer n is 1 in each instance.

In another embodiment, the hydrophilic spacer linker is a sulfuric acid ester, such as an alkyl ester of sulfuric acid. Illustratively, the spacer linker is of the following formula:

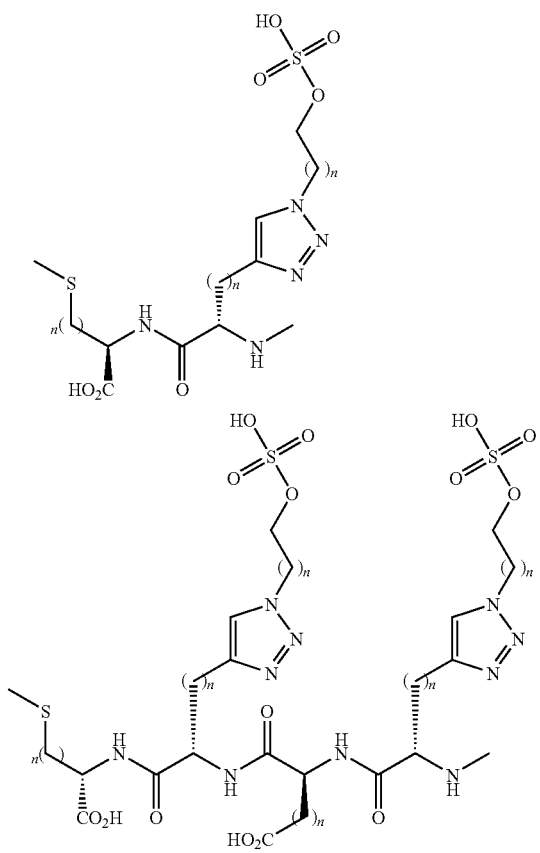

where n is an integer independently selected in each instance from 1 to about 3. Illustratively, n is independently 1 or 2 in each instance.

It is understood, that in such polyhydroxyl, polyamino, carboxylic acid, sulfuric acid, and like linkers that include free hydrogens bound to heteroatoms, one or more of those free hydrogen atoms may be protected with the appropriate hydroxyl, amino, or acid protecting group, respectively, or alternatively may be blocked as the corresponding pro-drugs, the latter of which are selected for the particular use, such as pro-drugs that release the parent drug under general or specific physiological conditions.

In each of the foregoing illustrative examples of linkers L, there are also included in some cases additional spacer linkers $L_S$, and/or additional releasable linkers $L_R$. Those spacer linker and releasable linkers also may include asymmetric carbon atoms. It is to be further understood that the stereochemical configurations shown herein are merely illustrative, and other stereochemical configurations are contemplated. For example in one variation, the corresponding unnatural amino acid configurations may be included in the conjugated described herein as follows:

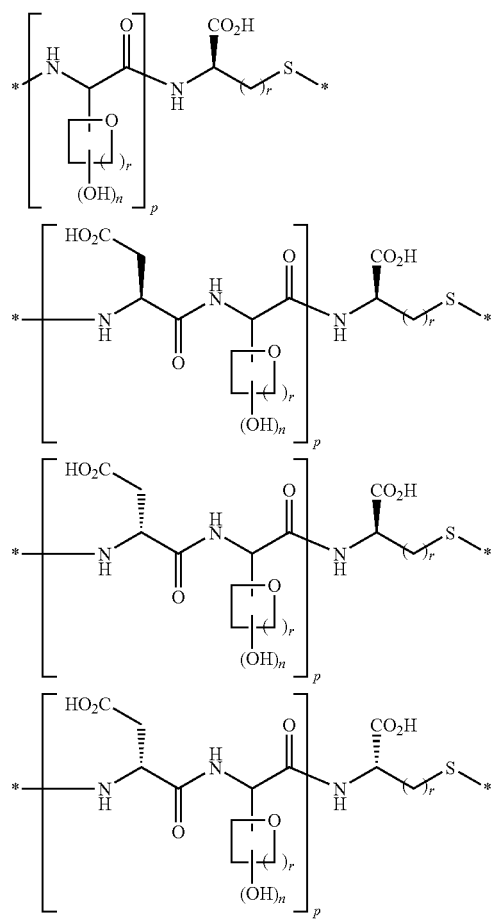

wherein n is an integer from 2 to about 5, p is an integer from 1 to about 5, and r is an integer from 1 to about 4, as described above.

Additional linkers that include hydrophilic groups useful in preparing the conjugates described herein are described in co-pending U.S. provisional application Ser. Nos. 60/946,092 and 61/036,186, the disclosures of which are incorporated herein by reference.

In another embodiment, multi-drug conjugates are described herein. Several illustrative configurations of such multi-drug conjugates are contemplated herein, and include the compounds and compositions described in PCT international publication No. WO 2007/022494, the disclosure of which is incorporated herein by reference. Illustratively, the polyvalent linkers may connect the receptor binding ligand B to the two or more agents A, providing that one agent is a tubulysin. Such polyvalent conjugates may be in a variety of structural configurations, including but not limited to the following illustrative general formulae:

$B-L^1-A^1-L^2-A^2$   $B-L^1-A^1-L^2-A^2-L^3-A^3$ $A^1-L^1-B-L^2-A^2$   $A^1-L^1-B-L^2-A^2-L^3-A^3$

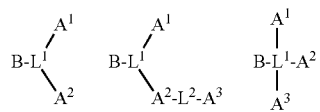

-continued

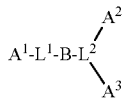

where B is the receptor binding ligand, each of ($L^1$), ($L^2$), and ($L^3$) is a polyvalent linker as described herein comprising a hydrophilic spacer linker, and optionally including one or more releasable linkers and/or additional spacer linkers, and each of ($A^1$), ($A^2$), and ($A^3$) is an agent A, or an analog or derivative thereof. Other variations, including additional agents A, or analogs or derivatives thereof, additional linkers, and additional configurations of the arrangement of each of (B), (L), and (A), are also contemplated herein.

In one variation, more than one receptor binding ligand B is included in the delivery conjugates described herein, including but not limited to the following illustrative general formulae:

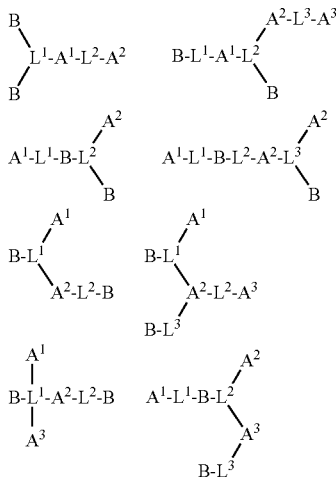

where each B is a receptor binding ligand, each of ($L^1$), ($L^2$), and ($L^3$) is a polyvalent linker as described herein comprising a hydrophilic spacer linker, and optionally including one or more releasable linkers and/or additional spacer linkers, and each of ($A^1$), ($A^2$), and ($A^3$) is an agent A, or an analog or derivative thereof. Other variations, including additional agents A, or analogs or derivatives thereof, additional linkers, and additional configurations of the arrangement of each of (B), (L), and (A), are also contemplated herein. In one variation, the receptor binding ligands B are ligands for the same receptor, and in another variation, the receptor binding ligands B are ligands for different receptors.

In another illustrative embodiment, the additional agents are selected based on activity against one or more populations of pathogenic cells with a particular mechanism of action. Illustrative mechanisms of action include alkylating agents, other microtubule inhibitors, including those that stabilize and/or destabilize microtubule formation, including beta-tubulin agents, cyclin dependent kinase (CDK) inhibitors, topoisomerase inhibitors, protein synthesis inhibitors, protein kinase inhibitors, including Ras, Raf, PKC, PI3K, and like inhibitors, transcription inhibitor, antifolates, heat shock protein blockers, and the like.

Illustrative alkylating agents include, but are not limited to, mitomycins CBI, and the like. Illustrative cyclin dependent kinase (CDK) inhibitors include, but are not limited to, CYC202, seliciclib, R-roscovitine, AGM-1470, and the like. Illustrative topoisomerase inhibitors include, but are not limited to, doxorubicin, other anthracyclines, and the like. Illustrative protein synthesis inhibitors include, but are not limited to, bruceantin, and the like. Illustrative protein kinase inhibitors, including Ras, Raf, PKC, PI3K, and like inhibitors, include but are not limited to L-779,450, R115777, and the like. Illustrative transcription inhibitors include, but are not limited to, α-amanatin, actinomycin, and the like. Illustrative antifolates include, but are not limited to, methotrexate, and the like. Illustrative heat shock protein blockers include, but are not limited to, geldanamycin, and the like.

Illustrative microtubule inhibitors, including those that stabilize and/or destabilize microtubule formation, including β-tubulin agents, microtubule poisons, and the like. Illustrative microtubule poisons that bind to selected receptors include, but are not limited to, inhibitors biding to the vinca binding site such as arenastatin, dolastatin, halichondrin B, maytansine, phomopsin A, rhizoxin, ustiloxin, vinblastine, vincristine, and the like, stabilizers binding to the taxol binding site such as discodermalide, epothilone, taxol, paclitaxol, and the like, inhibitors binding to the colchicine binding site such as, colchicine, combretastatin, curacin A, podophyllotoxin, steganacine, and the like, and others binding to undefined sites such as cryptophycin, tubulysins, and the like.

In one embodiment, one of the agents is a tubulysin, or an analog or derivative thereof, and at least one other of the agents is a DNA alkylation agent. In one variation, at least one other of the agents is an alkylating agent. In another variation, at least one other of the drugs is a P-glycoprotein (PGP) inhibitor. In another variation, at least one of the other agents is a vinca alkaloid, or an analog or derivative thereof. Vinca alklaloids described herein include all members of the vinca indole-dihydroindole family of alkaloids, such as but not limited to vindesine, vinblastine, vincristine, catharanthine, vindoline, leurosine, vinorelbine, imidocarb, sibutramine, toltrazuril, vinblastinoic acid, and the like, and analogs and derivatives thereof.

The binding site for the binding ligand (B), such as a vitamin, can include receptors for any binding ligand (B), or a derivative or analog thereof, capable of specifically binding to a receptor wherein the receptor or other protein is uniquely expressed, overexpressed, or preferentially expressed by a population of pathogenic cells. A surface-presented protein uniquely expressed, overexpressed, or preferentially expressed by the pathogenic cells is typically a receptor that is either not present or present at lower concentrations on non-pathogenic cells providing a means for selective elimination of the pathogenic cells. The binding ligand drug delivery conjugates may be capable of high affinity binding to receptors on cancer cells or other types of pathogenic cells. The high affinity binding can be inherent to the binding ligand or the binding affinity can be enhanced by the use of a chemically modified ligand (e.g., an analog or a derivative of a vitamin).

The binding ligand drug delivery conjugates described herein can be formed from, for example, a wide variety of vitamins or receptor-binding vitamin analogs/derivatives, linkers, and drugs. The binding ligand drug delivery conjugates described herein are capable of selectively targeting a population of pathogenic cells in the host animal due to preferential expression of a receptor for the binding ligand, such as a vitamin, accessible for ligand binding, on the pathogenic cells. Illustrative vitamin moieties that can be used as the binding ligand (B) include carnitine, inositol, lipoic acid, pyridoxal, ascorbic acid, niacin, pantothenic acid, folic acid, riboflavin, thiamine, biotin, vitamin $B_{12}$, and the lipid soluble vitamins A, D, E and K. These vitamins, and their receptor-binding analogs and derivatives, constitute an illustrative targeting entity that can be coupled with the drug by a bivalent linker (L) to form a binding ligand (B) drug delivery conjugate as described herein. The term vitamin is understood to include vitamin analogs and/or derivatives, unless otherwise indicated. Illustratively, pteroic acid which is a derivative of folate, biotin analogs such as biocytin, biotin sulfoxide, oxybiotin and other biotin receptor-binding compounds, and the like, are considered to be vitamins, vitamin analogs, and vitamin derivatives. It should be appreciated that vitamin analogs or derivatives as described herein refer to vitamins that incorporates an heteroatom through which the vitamin analog or derivative is covalently bound to the bivalent linker (L).

Illustrative vitamin moieties include folic acid, biotin, riboflavin, thiamine, vitamin $B_{12}$, and receptor-binding analogs and derivatives of these vitamin molecules, and other related vitamin receptor binding molecules.

In one embodiment, the targeting ligand B is a folate, an analog of folate, or a derivative of folate. It is to be understood as used herein, that the term folate is used both individually and collectively to refer to folic acid itself, and/or to such analogs and derivatives of folic acid that are capable of binding to folate receptors.

Illustrative embodiments of folate analogs and/or derivatives include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate. The dideaza analogs include, for example, 1,5-dideaza, 5,10-dideaza, 8,10-dideaza, and 5,8-dideaza analogs of folate. Other folates useful as complex forming ligands include the folate receptor-binding analogs aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing folic acid analogs and/or derivatives are conventionally termed folates, reflecting their ability to bind with folate-receptors, and such ligands when conjugated with exogenous molecules are effective to enhance transmembrane transport, such as via folate-mediated endocytosis as described herein. Other suitable binding ligands capable of binding to folate receptors to initiate receptor mediated endocytotic transport of the complex include antibodies to the folate receptor. An exogenous molecule in complex with an antibody to a folate receptor is used to trigger transmembrane transport of the complex.

Additional analogs of folic acid that bind to folic acid receptors are described in US Patent Application Publication Serial Nos. 2005/0227985 and 2004/0242582, the disclosures of which are incorporated herein by reference. Illustratively, such folate analogs have the general formula:

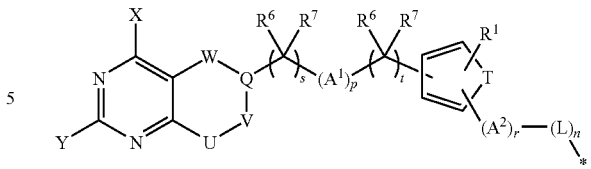

wherein X and Y are each-independently selected from the group consisting of halo, $R^2$, $OR^2$, $SR^3$, and $NR^4R^5$;

U, V, and W represent divalent moieties each independently selected from the group consisting of —($R^{6a}$)C═, —N═, —($R^{6a}$)C($R^{7a}$), and —N($R^{4a}$)—; Q is selected from the group consisting of C and CH; T is selected from the group consisting of S, O, N, and —C═C—;

$A^1$ and $A^2$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$), —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C═CH)—, —N(CH$_2$C═CH)—, $C_1$-$C_{12}$ alkylene, and $C_1$-$C_{12}$ alkyeneoxy, where Z is oxygen or sulfur;

$R^1$ is selected-from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

L is a divalent linker as described herein; and n, p, r, s and t are each independently either 0 or 1.

As used herein, it is to be understood that the term folate refers both individually to folic acid used in forming a conjugate, or alternatively to a folate analog or derivative thereof that is capable of binding to folate or folic acid receptors.

The vitamin can be folate which includes a nitrogen, and in this embodiment, the spacer linkers can be alkylenecarbonyl, cycloalkylenecarbonyl, carbonylalkylcarbonyl, 1-alkylenesuccinimid-3-yl, 1-(carbonylalkyl)succinimid-3-yl, wherein each of the spacer linkers is optionally substituted with a substituent $X^1$, and the spacer linker is bonded to the folate nitrogen to form an imide or an alkylamide. In this embodiment, the substituents $X^1$ can be alkyl, hydroxyalkyl, amino, aminoalkyl, alkylaminoalkyl, dialkylaminoalkyl, sulfhydrylalkyl, alkylthioalkyl, aryl, substituted aryl, arylalkyl, substituted arylalkyl, carboxy, carboxyalkyl, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

Illustrative embodiments of vitamin analogs and/or derivatives also include analogs and derivatives of biotin such as biocytin, biotin sulfoxide, oxybiotin and other biotin receptor-binding compounds, and the like. It is appreciated that analogs and derivatives of the other vitamins described herein are also contemplated herein. In one embodiment, vitamins that can be used as the binding ligand (B) in the drug delivery conjugates described herein include those that bind to vitamin receptors expressed specifically on activated macrophages, such as the folate receptor, which binds folate, or an analog or derivative thereof as described herein.

In addition to the vitamins described herein, it is appreciated that other binding ligands may be coupled with the drugs and linkers described and contemplated herein to form binding ligand-linker-drug conjugates capable of facilitating delivery of the drug to a desired target. These other binding ligands, in addition to the vitamins and their analogs and derivatives described, may be used to form drug delivery conjugates capable of binding to target cells. In general, any binding ligand (B) of a cell surface receptor may be advantageously used as a targeting ligand to which a linker-drug conjugate can be attached. Illustrative other ligands contemplated herein include peptide ligands identified from library screens, tumor cell-specific peptides, tumor cell-specific aptamers, tumor cell-specific carbohydrates, tumor cell-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor λ ligands, β-lactam antibiotics such as penicillin, small organic molecules including antimicrobial drugs, and other molecules that bind specifically to a receptor preferentially expressed on the surface of tumor cells or on an infectious organism, antimicrobial and other drugs designed to fit into the binding pocket of a particular receptor based on the crystal structure of the receptor or other cell surface protein, binding ligands of tumor antigens or other molecules preferentially expressed on the surface of tumor cells, or fragments of any of these molecules. An example of a tumor-specific antigen that could function as a binding site for a binding ligand-drug conjugate include extracellular epitopes of a member of the Ephrin family of proteins, such as EphA2. EphA2 expression is restricted to cell-cell junctions in normal cells, but EphA2 is distributed over the entire cell surface in metastatic tumor cells. Thus, EphA2 on metastatic cells would be accessible for binding to, for example, an Fab fragment of an antibody conjugated to a drug, whereas the protein would not be accessible for binding to the Fab fragment on normal cells, resulting in a binding ligand-drug conjugate specific for metastatic cancer cells.

In another embodiment, methods for treating diseases caused by or evidenced by pathogenic cell populations are described herein. The binding ligand (B) drug delivery conjugates can be used to treat disease states characterized by the presence of a pathogenic cell population in the host wherein the members of the pathogenic cell population have an accessible binding site for the binding ligand (B), or analog or derivative thereof, wherein the binding site is uniquely expressed, overexpressed, or preferentially expressed by the pathogenic cells. The selective elimination of the pathogenic cells is mediated by the binding of the ligand moiety of the binding ligand (B) drug delivery conjugate to a ligand receptor, transporter, or other surface-presented protein that specifically binds the binding ligand (B), or analog or derivative thereof, and which is uniquely expressed, overexpressed, or preferentially expressed by the pathogenic cells. A surface-presented protein uniquely expressed, overexpressed, or preferentially expressed by the pathogenic cells is a receptor not present or present at lower concentrations on non-pathogenic cells providing a means for selective elimination of the pathogenic cells.

For example, surface-expressed vitamin receptors, such as the high-affinity folate receptor, are overexpressed on cancer cells. Epithelial cancers of the ovary, mammary gland, colon, lung, nose, throat, and brain have all been reported to express elevated levels of the folate receptor. In fact, greater than 90% of all human ovarian tumors are known to express large amounts of this receptor. Accordingly, the binding ligand (B) drug delivery conjugates described herein can be used to treat a variety of tumor cell types, as well as other types of pathogenic cells, such as infectious agents, that preferentially express ligand receptors, such as vitamin receptors, and, thus, have surface accessible binding sites for ligands, such as vitamins, or vitamin analogs or derivatives. In one aspect, methods are described herein for targeting binding ligand-linker-drug conjugates to maximize targeting of the pathogenic cells for elimination.

The binding ligand (B) drug delivery conjugates described herein can be used for both human clinical medicine and veterinary applications. Thus, the host animal harboring the population of pathogenic cells and treated with the binding ligand (e.g., a vitamin) drug delivery conjugates can be human or, in the case of veterinary applications, can be a laboratory, agricultural, domestic, or wild animal. The methods described herein can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The methods are applicable to populations of pathogenic cells that cause a variety of pathologies in these host animals. The term pathogenic cells refers to for example cancer cells, infectious agents such as bacteria and viruses, bacteria- or virus-infected cells, activated macrophages capable of causing a disease state, and any other type of pathogenic cells that uniquely express, preferentially express, or overexpress binding ligand receptors, such as vitamin receptors or receptors that bind analogs or derivatives of vitamins. Pathogenic cells can also include any cells causing a disease state for which treatment with the binding ligand drug delivery conjugates described herein results in reduction of the symptoms of the disease. For example, the pathogenic cells can be host cells that are pathogenic under some circumstances such as cells of the immune system that are responsible for graft versus host disease, but not pathogenic under other circumstances.

Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The methods can be utilized to treat such cancers as carcinomas, sarcomas, lymphomas, Hodgkin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

In embodiments where the pathogenic cell population is a cancer cell population, the effect of conjugate administration is a therapeutic response measured by reduction or elimination of tumor mass or of inhibition of tumor cell proliferation. In the case of a tumor, the elimination can be an elimination of cells of the primary tumor or of cells that have metastasized or are in the process of dissociating from the primary tumor. A prophylactic treatment with the binding ligand (B) drug delivery conjugate (e.g., a vitamin used as the binding ligand) to prevent return of a tumor after its removal by any therapeutic approach including surgical removal of the tumor, radiation therapy, chemotherapy, or biological therapy is also described. The prophylactic treatment can be an initial treatment with the binding ligand (B) drug delivery conjugate, such as treatment in a multiple dose daily regimen, and/or can be an additional treatment or series of treatments after an interval of days or months following the initial treatment(s). Accordingly, elimination of any of the pathogenic cell populations treated using the described methods includes reduction in the number of pathogenic cells, inhibition of proliferation of pathogenic cells, a prophylactic treatment that prevents return of pathogenic cells, or a treatment of pathogenic cells that results in reduction of the symptoms of disease.

In cases where cancer cells are being eliminated, the methods can be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

The methods are also applicable to populations of pathogenic cells that cause a variety of infectious diseases. For example, the methods are applicable to such populations of pathogenic cells as bacteria, fungi, including yeasts, viruses, virus-infected cells, mycoplasma, and parasites. Infectious organisms that can be treated with the binding ligand (B) drug delivery conjugates described herein are any art-recognized infectious organisms that cause pathogenesis in an animal, including such organisms as bacteria that are gram-negative or gram-positive cocci or bacilli. For example, *Proteus* species, *Klebsiella* species, *Providencia* species, *Yersinia* species, *Erwinia* species, *Enterobacter* species, *Salmonella* species, *Serratia* species, *Aerobacter* species, *Escherichia* species, *Pseudomonas* species, *Shigella* species, *Vibrio* species, *Aeromonas* species, *Campylobacter* species, *Streptococcus* species, *Staphylococcus* species, *Lactobacillus* species, *Micrococcus* species, *Moraxella* species, *Bacillus* species, *Clostridium* species, *Corynebacterium* species, *Eberthella* species, *Micrococcus* species, *Mycobacterium* species, *Neisseria* species, *Haemophilus* species, *Bacteroides* species, *Listeria* species, *Erysipelothrix* species, *Acinetobacter* species, *Brucella* species, *Pasteurella* species, *Vibrio* species, *Flavobacterium* species, *Fusobacterium* species, *Streptobacillus* species, *Calymmatobacterium* species, *Legionella* species, *Treponema* species, *Borrelia* species, *Leptospira* species, *Actinomyces* species, *Nocardia* species, *Rickettsia* species, and any other bacterial species that causes disease in a host can be treated with the binding ligand drug delivery conjugates described herein.

Of particular interest are bacteria that are resistant to antibiotics such as antibiotic-resistant *Streptococcus* species and *Staphlococcus* species, or bacteria that are susceptible to antibiotics, but cause recurrent infections treated with antibiotics so that resistant organisms eventually develop. Bacteria that are susceptible to antibiotics, but cause recurrent infections treated with antibiotics so that resistant organisms eventually develop, can be treated with the binding ligand (B) drug delivery conjugates described herein in the absence of antibiotics, or in combination with lower doses of antibiotics than would normally be administered to a patient, to avoid the development of these antibiotic-resistant bacterial strains.

Viruses, such as DNA and RNA viruses, can also be treated with the described methods. Such viruses include, but are not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picornaviruses, paramyxoviruses, reoviruses, retroviruses, lentiviruses, and rhabdoviruses.

The methods are also applicable to any fungi, including yeasts, mycoplasma species, parasites, or other infectious organisms that cause disease in animals. Examples of fungi that can be treated with the methods and compositions include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidioidomycosis, mucormycosis, chromoblastomycosis, dermatophytosis, protothecosis, fusariosis, pityriasis, mycetoma, paracoccidioidomycosis, phaeohyphomycosis, pseudallescheriasis, sporotrichosis, trichosporosis, pneumocystis infection, and candidiasis.

The methods can also be utilized to treat parasitic infections including, but not limited to, infections caused by tapeworms, such as *Taenia*, *Hymenolepsis*, *Diphyllobothrium*, and *Echinococcus* species, flukes, such as *Fasciolopsis*, *Heterophyes*, *Metagonimus*, *Clonorchis*, *Fasciola*, *Paragonimus*, and *Schitosoma* species, roundworms, such as *Enterobius*, *Trichuris*, *Ascaris*, *Ancylostoma*, *Necator*, *Strongyloides*, *Trichinella*, *Wuchereria*, *Brugia*, *Loa Onchocerca*, and *Dracunculus* species, ameba, such as *Naegleria* and *Acanthamoeba* species, and protozoans, such as *Plasmodium*, *Trypanosoma*, *Leishmania*, *Toxoplasma*, *Entamoeba*, *Giardia*, *Isospora*, *Cryptosporidium*, and *Enterocytozoon* species.

The pathogenic cells to which the binding ligand drug delivery conjugates described herein are directed can also be cells harboring endogenous pathogens, such as virus-, mycoplasma-, parasite-, or bacteria-infected cells, if these cells preferentially express ligand receptors, such as vitamin receptors.

In one embodiment, the binding ligand drug delivery conjugates can be internalized into the targeted pathogenic cells upon binding of the binding ligand moiety to a receptor, transporter, or other surface-presented protein that specifically binds the ligand and which is preferentially expressed on the pathogenic cells. Such internalization can occur, for example, through receptor-mediated endocytosis. If the binding ligand (B) drug delivery conjugate contains a releasable linker, the binding ligand moiety and the drug can dissociate intracellularly and the drug can act on its intracellular target.

In an alternate embodiment, the binding ligand moiety of the drug delivery conjugate can bind to the pathogenic cell placing the drug in close association with the surface of the pathogenic cell. The drug can then be released by cleavage of the releasable linker. For example, the drug can be released by a protein disulfide isomerase if the releasable linker is a disulfide group. The drug can then be taken up by the pathogenic cell to which the binding ligand (B) drug delivery conjugate is bound, or the drug can be taken up by another pathogenic cell in close proximity thereto. Alternatively, the drug could be released by a protein disulfide isomerase inside the cell where the releasable linker is a disulfide group. The drug may also be released by a hydrolytic mechanism, such as acid-catalyzed hydrolysis, as described above for certain beta elimination mechanisms, or by an anchimerically assisted cleavage through an oxonium ion or lactonium ion producing mechanism. The selection of the releasable linker or linkers will dictate the mechanism by which the drug is released from the conjugate. It is appreciated that such a selection can be pre-defined by the conditions wherein the drug conjugate will be used. Alternatively, the drug delivery conjugates can be internalized into the targeted cells upon binding, and the binding ligand and the drug can remain associated intracellularly with the drug exhibiting its effects without dissociation from the vitamin moiety.

In still another embodiment where the binding ligand is a vitamin, the vitamin-drug delivery conjugate can act through a mechanism independent of cellular vitamin receptors. For example, the drug delivery conjugates can bind to soluble vitamin receptors present in the serum or to serum proteins, such as albumin, resulting in prolonged circulation of the conjugates relative to the unconjugated drug, and in increased activity of the conjugates towards the pathogenic cell population relative to the unconjugated drug.

In one embodiment, the drugs for use in the methods described herein remain stable in serum for at least 4 hours. In another embodiment the drugs have an $IC_{50}$ in the nanomolar range, and, in another embodiment, the drugs are water soluble. If the drug is not water soluble, the bivalent linker (L) can be derivatized to enhance water solubility. The term drug also means any of the drug analogs or derivatives described hereinabove. It should be appreciated that a drug analog or derivative can mean a drug that incorporates an heteroatom through which the drug analog or derivative is covalently bound to the bivalent linker (L).

The binding ligand drug delivery conjugates can comprise a binding ligand (B), a bivalent linker (L), a drug, and, optionally, heteroatom linkers to link the binding ligand (B) receptor binding moiety and the drug to the bivalent linker (L). In one illustrative embodiment, it should be appreciated that a vitamin analog or derivative can mean a vitamin that incorporates an heteroatom through which the vitamin analog or derivative is covalently bound to the bivalent linker (L). Thus, in this illustrative embodiment, the vitamin can be covalently bound to the bivalent linker (L) through an heteroatom linker, or a vitamin analog or derivative (i.e., incorporating an heteroatom) can be directly bound to the bivalent linker (L). In similar illustrative embodiments, a drug analog or derivative is a drug, and a drug analog or derivative can mean a drug that incorporates an heteroatom through which the drug analog or derivative is covalently bound to the bivalent linker (L). Thus, in these illustrative aspects, the drug can be covalently bound to the bivalent linker (L) through an heteroatom linker, or a drug analog or derivative (i.e., incorporating an heteroatom) can be directly bound to the bivalent linker (L). The bivalent linker (L) can comprise a spacer linker, a releasable (i.e., cleavable) linker, and an heteroatom linker to link the spacer linker to the releasable linker in conjugates containing both of these types of linkers.

Generally, any manner of forming a conjugate between the bivalent linker (L) and the binding ligand (B), or analog or derivative thereof, between the bivalent linker (L) and the drug, or analog or derivative thereof, including any intervening heteroatom linkers, can be utilized. Also, any art-recognized method of forming a conjugate between the spacer linker, the releasable linker, and the heteroatom linker to form the bivalent linker (L) can be used. The conjugate can be formed by direct conjugation of any of these molecules, for example, through complexation, or through hydrogen, ionic, or covalent bonds. Covalent bonding can occur, for example, through the formation of amide, ester, disulfide, or imino bonds between acid, aldehyde, hydroxy, amino, sulfhydryl, or hydrazo groups.

In another embodiment, pharmaceutical compositions comprising an amount of a binding ligand (B) drug delivery conjugate effective to eliminate a population of pathogenic cells in a host animal when administered in one or more doses are described. The binding ligand drug delivery conjugate is preferably administered to the host animal parenterally, e.g., intradermally, subcutaneously, intramuscularly, intraperitoneally, intravenously, or intrathecally. Alternatively, the binding ligand drug delivery conjugate can be administered to the host animal by other medically useful processes, such as orally, and any effective dose and suitable therapeutic dosage form, including prolonged release dosage forms, can be used.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

In one illustrative aspect, at least one additional composition comprising a therapeutic factor can be administered to the host in combination or as an adjuvant to the above-detailed methodology, to enhance the binding ligand drug delivery conjugate-mediated elimination of the population of pathogenic cells, or more than one additional therapeutic factor can be administered. The therapeutic factor can be selected from a chemotherapeutic agent, or another therapeutic factor capable of complementing the efficacy of the administered binding ligand drug delivery conjugate.

In one illustrative aspect, therapeutically effective combinations of these factors can be used. In one embodiment, for example, therapeutically effective amounts of the therapeutic factor, for example, in amounts ranging from about 0.1 $MIU/m^2$/dose/day to about 15 $MIU/m^2$/dose/day in a multiple dose daily regimen, or for example, in amounts ranging from about 0.1 $MIU/m^2$/dose/day to about 7.5 $MIU/m^2$/dose/day in a multiple dose daily regimen, can be used along with the binding ligand drug delivery conjugates to eliminate, reduce, or neutralize pathogenic cells in a host animal harboring the pathogenic cells (MIU=million international units; $m^2$=approximate body surface area of an average human).

In another embodiment, chemotherapeutic agents, which are, for example, cytotoxic themselves or can work to enhance tumor permeability, are also suitable for use in the described methods in combination with the binding ligand drug delivery conjugates. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, maytansines and analogs and derivatives thereof, gemcitabine, and any other art-recognized antimicrobial compound.

The therapeutic factor can be administered to the host animal prior to, after, or at the same time as the binding ligand drug delivery conjugates and the therapeutic factor can be administered as part of the same composition containing the binding ligand drug delivery conjugate or as part of a different composition than the binding ligand drug delivery conjugate. Any such therapeutic composition containing the therapeutic factor at a therapeutically effective dose can be used.

Additionally, more than one type of binding ligand drug delivery conjugate can be used. Illustratively, for example, the host animal can be treated with conjugates with different vitamins, but the same drug in a co-dosing protocol. In other embodiments, the host animal can be treated with conjugates comprising the same binding ligand linked to different drugs, or various binding ligands linked to various drugs. In another illustrative embodiment, binding ligand drug delivery conjugates with the same or different vitamins, and the same or different drugs comprising multiple vitamins and multiple drugs as part of the same drug delivery conjugate could be used.

The unitary daily dosage of the binding ligand drug delivery conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. In illustrative embodiments, effective doses can range, for example, from about 1 ng/kg to about 1 mg/kg, from about 1 µg/kg to about 500 µg/kg, and from about 1 µg/kg to about 100 µg/kg.

In another illustrative aspect, any effective regimen for administering the binding ligand drug delivery conjugates can be used. For example, the binding ligand drug delivery conjugates can be administered as single doses, or can be divided and administered as a multiple-dose daily regimen. In other embodiments, a staggered regimen, for example, one to three days per week can be used as an alternative to daily treatment, and such intermittent or staggered daily regimen is considered to be equivalent to every day treatment and within the scope of the methods described herein. In one embodiment, the host is treated with multiple injections of the binding ligand drug delivery conjugate to eliminate the population of pathogenic cells. In another embodiment, the host is injected multiple times (preferably about 2 up to about 50 times) with the binding ligand drug delivery conjugate, for example, at 12-72 hour intervals or at 48-72 hour intervals. In other embodiments, additional injections of the binding ligand drug delivery conjugate can be administered to the patient at an interval of days or months after the initial injections(s) and the additional injections prevent recurrence of the disease state caused by the pathogenic cells.

In one embodiment, vitamins, or analogs or derivatives thereof, that can be used in the binding ligand drug delivery conjugates include those that bind to receptors expressed specifically on activated macrophages, such as the folate receptor which binds folate, or an analog or derivative thereof. The folate-linked conjugates, for example, can be used to kill or suppress the activity of activated macrophages that cause disease states in the host. Such macrophage targeting conjugates, when administered to a patient suffering from an activated macrophage-mediated disease state, work to concentrate and associate the conjugated drug in the population of activated macrophages to kill the activated macrophages or suppress macrophage function. Elimination, reduction, or deactivation of the activated macrophage population works to stop or reduce the activated macrophage-mediated pathogenesis characteristic of the disease state being treated. Exemplary of diseases known to be mediated by activated macrophages include rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD) and chronic inflammations. Administration of the drug delivery conjugate is typically continued until symptoms of the disease state are reduced or eliminated.

Illustratively, the binding ligand drug delivery conjugates administered to kill activated macrophages or suppress the function of activated macrophages can be administered parenterally to the animal or patient suffering from the disease state, for example, intradermally, subcutaneously, intramuscularly, intraperitoneally, or intravenously in combination with a pharmaceutically acceptable carrier. In another embodiment, the binding ligand drug delivery conjugates can be administered to the animal or patient by other medically useful procedures and effective doses can be administered in standard or prolonged release dosage forms. In another aspect, the therapeutic method can be used alone or in combination with other therapeutic methods recognized for treatment of disease states mediated by activated macrophages.

The drug delivery conjugates described herein can be prepared by art-recognized synthetic methods. The synthetic methods are chosen depending upon the selection of the optionally addition heteroatoms or the heteroatoms that are already present on the spacer linkers, releasable linkers, the drug, and/or or the binding ligand. In general, the relevant bond forming reactions are described in Richard C. Larock, "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which are incorporated herein by reference.

EXAMPLES

Compound Examples

The compounds described herein may be prepared using the process and syntheses described herein, as well as using general organic synthetic methods. In particular, methods for preparing the compounds are described in U.S. patent application publication 2005/0002942, the disclosure of which is incorporated herein by reference.

General formation of folate-peptides. The folate-containing peptidyl fragment Pte-Glu-(AA)$_n$-NH(CHR$_2$)CO$_2$H (3) is prepared by a polymer-supported sequential approach using standard methods, such as the Fmoc-strategy on an acid-sensitive Fmoc-AA-Wang resin (1), as shown in the following Scheme:

Scheme

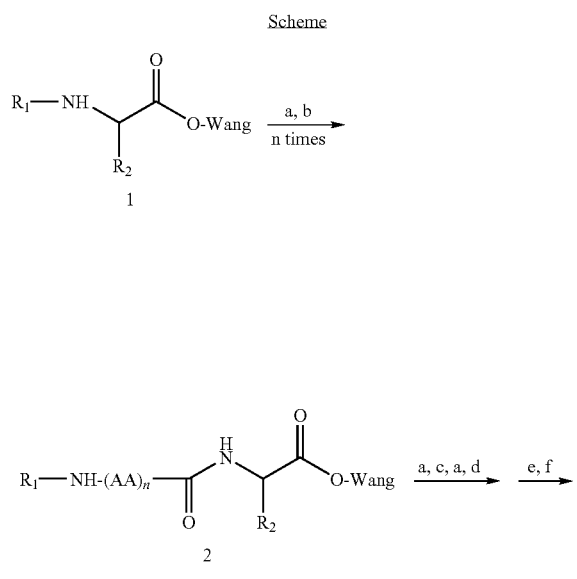

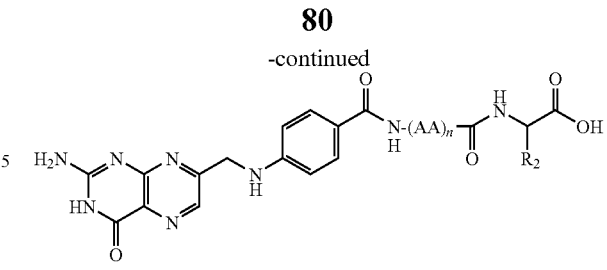

3

(a) 20% piperidine/DMF; (b) Fmoc-AA-OH, PyBop, DIPEA, DMF; (c) Fmoc-Glu(O-t-Bu)-OH, PyBop, DIPEA, DMF; (d) 1. N$^{10}$(TFA)-Pte-OH; PyBop, DIPEA, DMSO; (e) TFAA, (CH$_2$SH)$_2$, i-Pr$_3$SiH; (f) NH$_4$OH, pH 10.3.

In this illustrative embodiment of the processes described herein, R$_1$ is Fmoc, R$_2$ is the desired appropriately-protected amino acid side chain, and DIPEA is diisopropylethylamine. Standard coupling procedures, such as PyBOP and others described herein or known in the art are used, where the coupling agent is illustratively applied as the activating reagent to ensure efficient coupling. Fmoc protecting groups are removed after each coupling step under standard conditions, such as upon treatment with piperidine, tetrabutylammonium fluoride (TBAF), and the like. Appropriately protected amino acid building blocks, such as Fmoc-Glu-OtBu, N$^{10}$-TFA-Pte-OH, and the like, are used, as described in the Scheme, and represented in step (b) by Fmoc-AA-OH. Thus, AA refers to any amino acid starting material, that is appropriately protected. It is to be understood that the term amino acid as used herein is intended to refer to any reagent having both an amine and a carboxylic acid functional group separated by one or more carbons, and includes the naturally occurring alpha and beta amino acids, as well as amino acid derivatives and analogs of these amino acids. In particular, amino acids having side chains that are protected, such as protected serine, threonine, cysteine, aspartate, and the like may also be used in the folate-peptide synthesis described herein. Further, gamma, delta, or longer homologous amino acids may also be included as starting materials in the folate-peptide synthesis described herein. Further, amino acid analogs having homologous side chains, or alternate branching structures, such as norleucine, isovaline, β-methyl threonine, β-methyl cysteine, β,β-dimethyl cysteine, and the like, may also be included as starting materials in the folate-peptide synthesis described herein.

The coupling sequence (steps (a) & (b)) involving Fmoc-AA-OH is performed "n" times to prepare solid-support peptide (2), where n is an integer and may equal 0 to about 100. Following the last coupling step, the remaining Fmoc group is removed (step (a)), and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups that may form part of the appropriately-protected amino acid side chain. The TFA protecting group is removed upon treatment with base (step (f)) to provide the folate-containing peptidyl fragment (3).

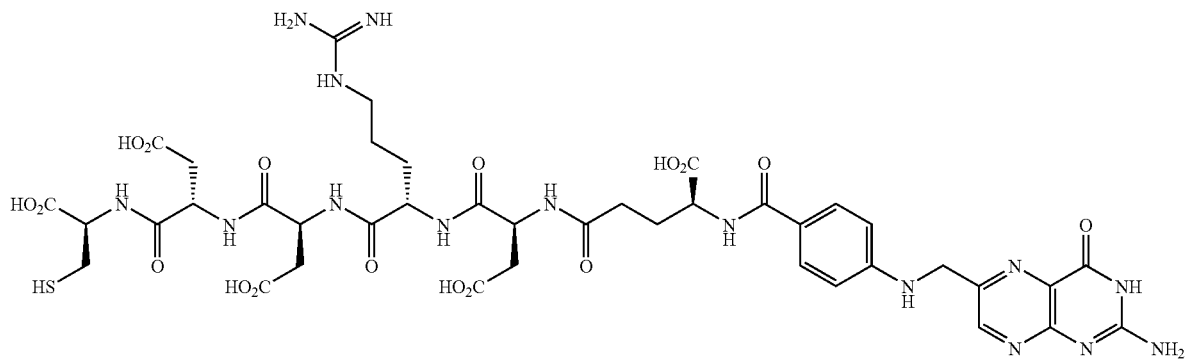 [SMILES: N=C(N)NCCC[C@H](NC(=O)[C@H](CC(=O)O)NC(=O)CC[C@H](NC(=O)c1ccc(NCc2cnc3nc(N)[nH]c(=O)c3n2)cc1)C(=O)O)C(=O)N[C@@H](CC(=O)O)C(=O)N[C@@H](CC(=O)O)C(=O)N[C@@H](CS)C(=O)O]

According to the general procedure described herein, Wang resin bound 4-methoxytrityl (MTT)-protected Cys-NH$_2$ was reacted according to the following sequence: 1) a. Fmoc-Asp(OtBu)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Arg(Pbf)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu-OtBu, PyBOP, DIPEA; b. 20% Piperidine/DMF; 6) N$^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. Selected $^1$H NMR (D$_2$O) δ (ppm) 8.68 (s, 1H, FA H-7), 7.57 (d, 2H, J=8.4 Hz, FA H-12 & 16), 6.67 (d, 2H, J=9 Hz, FA H-13 & 15), 4.40-4.75 (m, 5H), 4.35 (m, 2H), 4.16 (m, 1H), 3.02 (m, 2H), 2.55-2.95 (m, 8H), 2.42 (m, 2H), 2.00-2.30 (m, 2H), 1.55-1.90 (m, 2H), 1.48 (m, 2H); MS (ESI, m+H$^+$) 1046.

| Reagent | (mmol) | equivalents | Amount |
|---|---|---|---|
| H-Cys(4-methoxytrityl)-2-chlorotrityl-Resin (loading 0.56 mmol/g) | 0.56 | 1 | 1.0 g |
| Fmoc-β-aminoalanine(NH-MTT)-OH | 1.12 | 2 | 0.653 g |
| Fmoc-Asp(OtBu)-OH | 1.12 | 2 | 0.461 g |
| Fmoc-Asp(OtBu)-OH | 1.12 | 2 | 0.461 g |
| Fmoc-Asp(OtBu)-OH | 1.12 | 2 | 0.461 g |
| Fmoc-Glu-OtBu | 1.12 | 2 | 0.477 g |
| N$^{10}$TFA-Pteroic Acid (dissolve in 10 ml DMSO) | 0.70 | 1.25 | 0.286 g |
| DIPEA | 2.24 | 4 | 0.390 mL |
| PyBOP | 1.12 | 2 | 0.583 g |

The coupling step was performed as follows: In a peptide synthesis vessel add the resin, add the amino acid solution, DIPEA, and PyBOP. Bubble argon for 1 hr. and wash 3×

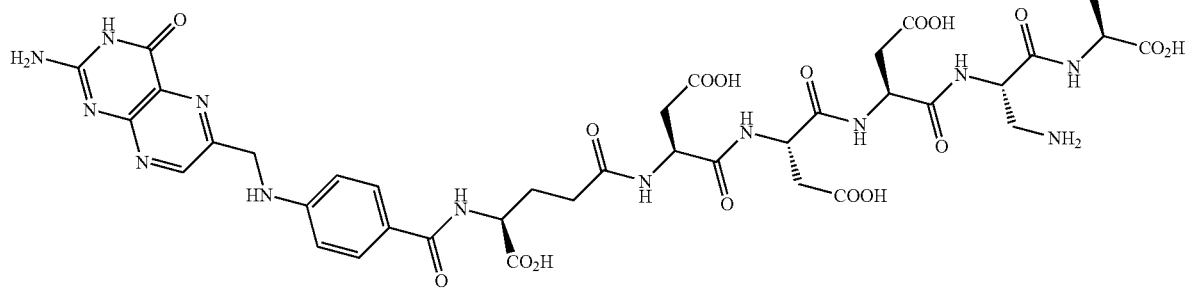

According to the general procedure described herein, Wang resin bound 4-methoxytrityl (MTT)-protected Cys-NH$_2$ was reacted according to the following sequence: 1) a. Fmoc-β-aminoalanine(NH-MTT)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Asp(OtBu)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu-OtBu, PyBOP, DIPEA; b. 20% Piperidine/DMF; 6) N$^{10}$-TFA-pteroic acid, PyBOP, DIPEA. The MTT, tBu, and TFA protecting groups were removed with a. 2% hydrazine/DMF; b. TFA/H$_2$O/TIPS/EDT (92.5:2.5:2.5:2.5).

The reagents shown in the following table were used in the preparation:

with DMF and IPA. Use 20% piperidine in DMF for Fmoc deprotection, 3× (10 min), before each amino acid coupling. Continue to complete all 6 coupling steps. At the end wash the resin with 2% hydrazine in DMF 3× (5 min) to cleave TFA protecting group on Pteroic acid.

Cleave the peptide analog from the resin using the following reagent, 92.5% (50 ml) TFA, 2.5% (1.34 ml) H$_2$O, 2.5% (1.34 ml) Triisopropylsilane, 2.5% (1.34 ml) ethanedithiol, the cleavage step was performed as follows: Add 25 ml cleavage reagent and bubble for 1.5 hr, drain, and wash 3× with remaining reagent. Evaporate to about 5 mL and precipitate in ethyl ether. Centrifuge and dry. Purification was performed as follows: Column-Waters NovaPak C$_{18}$ 300×19 mm; Buffer A=10 mM Ammonium Acetate, pH 5; B=CAN; 1% B to 20% B in 40 minutes at 15 ml/min, to 350 mg (64%); HPLC-RT 10.307 min., 100% pure, $^1$H HMR spectrum consistent with the assigned structure, and MS (ES−): 1624.8, 1463.2, 1462.3, 977.1, 976.2, 975.1, 974.1, 486.8, 477.8.

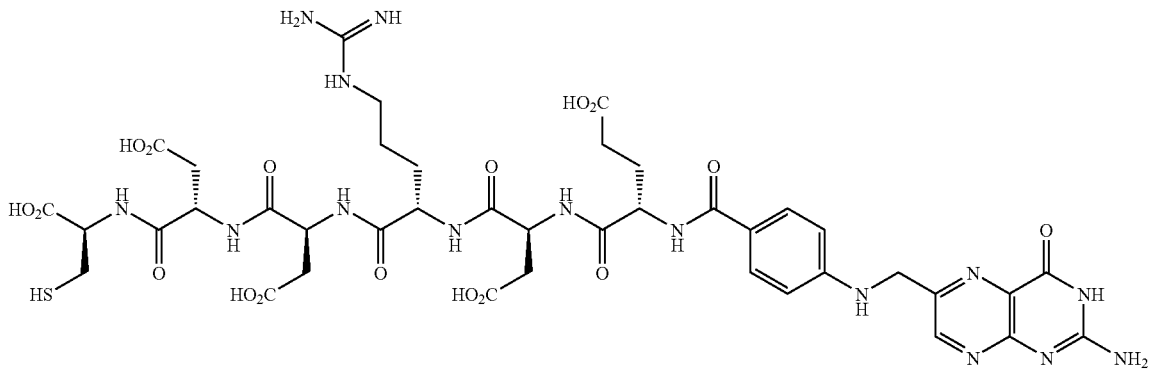 [SMILES: N=C(N)NCCC[C@H](NC(=O)[C@H](CC(=O)O)NC(=O)[C@H](CCC(=O)O)NC(=O)c1ccc(NCc2cnc3nc(N)[nH]c(=O)c3n2)cc1)C(=O)N[C@@H](CC(=O)O)C(=O)N[C@@H](CC(=O)O)C(=O)N[C@@H](CS)C(=O)O]

According to the general procedure described herein, Wang resin bound MTT-protected Cys-NH$_2$ was reacted according to the following sequence: 1) a. Fmoc-Asp(OtBu)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Arg(Pbf)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu(γ-OtBu)-OH, PyBOP, DIPEA; b. 20% Piperidine/DMF; 6) $N^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. The $^1$H NMR spectrum was consistent with the assigned structure.

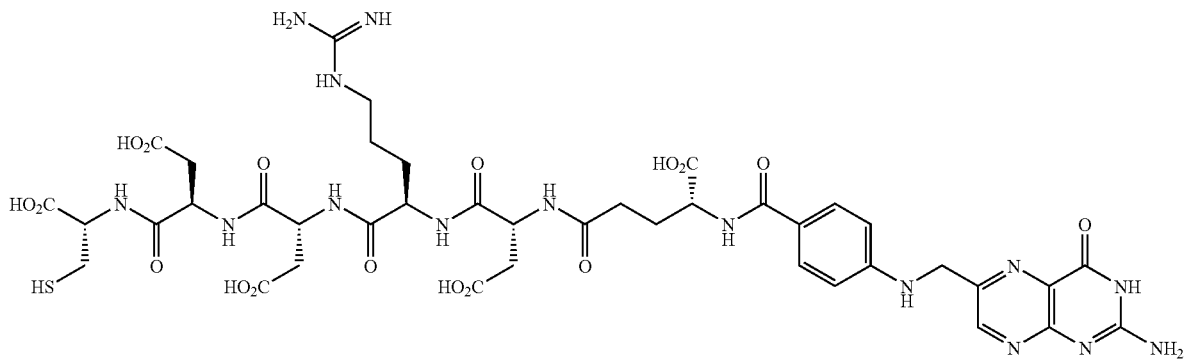 [SMILES: N=C(N)NCCC[C@@H](NC(=O)[C@@H](CC(=O)O)NC(=O)CC[C@@H](NC(=O)c1ccc(NCc2cnc3nc(N)[nH]c(=O)c3n2)cc1)C(=O)O)C(=O)N[C@H](CC(=O)O)C(=O)N[C@H](CC(=O)O)C(=O)N[C@H](CS)C(=O)O]

According to the general procedure described herein, Wang resin bound MTT-protected D-Cys-NH$_2$ was reacted according to the following sequence: 1) a. Fmoc-D-Asp(OtBu)-OH, PyBOP, DIPEA; b. 20% Piperidine/DMF; 2) a. Fmoc-D-Asp(OtBu)-OH, PyBOP, DIPEA; b. 20% Piperidine/DMF; 3) a. Fmoc-D-Arg(Pbf)-OH, PyBOP, DIPEA; b. 20% Piperidine/DMF; 4) a. Fmoc-D-Asp(OtBu)-OH, PyBOP, DIPEA; b. 20% Piperidine/DMF; 5) a. Fmoc-D-Glu-OtBu, PyBOP, DIPEA; b. 20% Piperidine/DMF; 6) $N^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. The $^1$H NMR spectrum was consistent with the assigned structure.

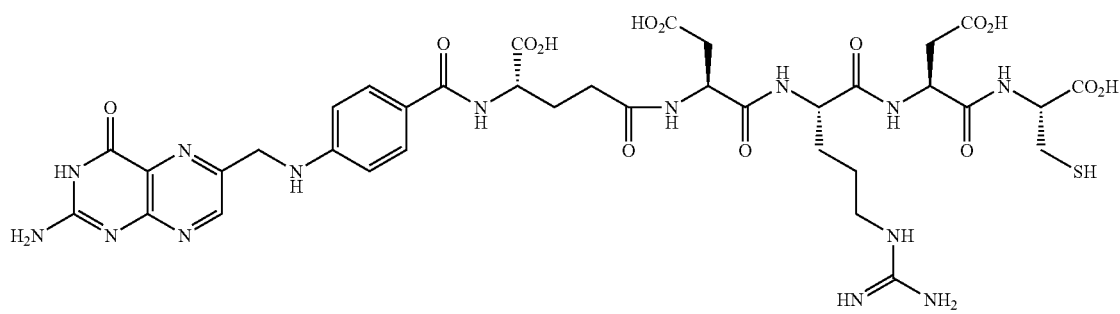 [SMILES: N=C(N)NCCC[C@H](NC(=O)[C@H](CC(=O)O)NC(=O)CC[C@H](NC(=O)c1ccc(NCc2cnc3nc(N)[nH]c(=O)c3n2)cc1)C(=O)O)C(=O)N[C@@H](CC(=O)O)C(=O)N[C@@H](CS)C(=O)O]
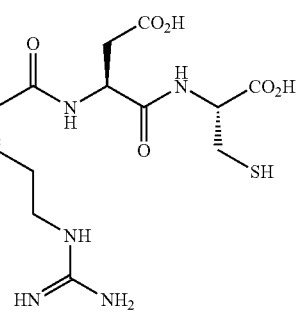

Similarly, EC089 was prepared as described herein.

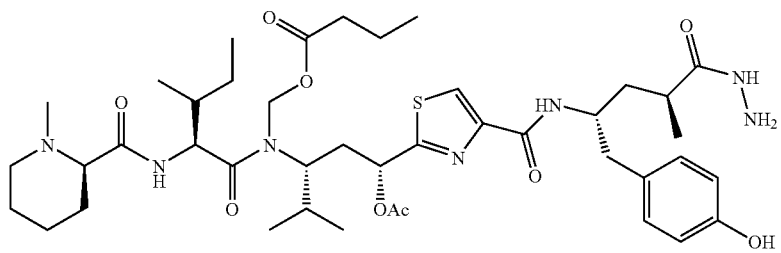 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NN)cs1)C(C)C]

Preparation of tubulysin hydrazides. Illustrated by preparing EC0347. N,N-Diisopropylethylamine (DIPEA, 6.1 µL) and isobutyl chloroformate (3.0 µL) were added with via syringe in tandem into a solution of tubulysin B (0.15 mg) in anhydrous EtOAc (2.0 mL) at −15° C. After stirring for 45 minutes at −15° C. under argon, the reaction mixture was cooled down to −20° C. and to which was added anhydrous hydrazine (5.0 µL). The reaction mixture was stirred under argon at −20° C. for 3 hours, quenched with 1.0 mM sodium phosphate buffer (pH 7.0, 1.0 mL), and injected into a preparative HPLC for purification. Column: Waters XTerra Prep MS $C_{18}$ 10 µm, 19×250 mm; Mobile phase A: 1.0 mM sodium phosphate buffer, pH 7.0; Mobile phase B: acetonitrile; Method: 10% B to 80% B over 20 minutes, flow rate=25 mL/min. Fractions from 15.14-15.54 minutes were collected and lyophilized to produce EC0347 as a white solid (2.7 mg). The foregoing method is equally applicable for preparing other tubulysin hydrazides by the appropriate selection of the tubulysin starting compound.

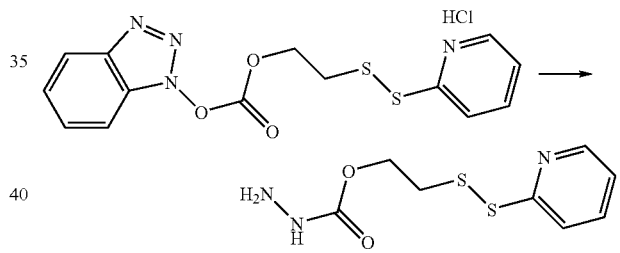

Synthesis of coupling reagent EC0311. DIPEA (0.60 mL) was added to a suspension of HOBt-OCO$_2$—(CH$_2$)$_2$—SS-2-pyridine HCl (685 mg, 91%) in anhydrous DCM (5.0 mL) at 0° C., stirred under argon for 2 minutes, and to which was added anhydrous hydrazine (0.10 mL). The reaction mixture was stirred under argon at 0° C. for 10 minutes and room temperature for an additional 30 minutes, filtered, and the filtrate was purified by flash chromatography (silica gel, 2% MeOH in DCM) to afford EC0311 as a clear thick oil (371 mg), solidified upon standing.

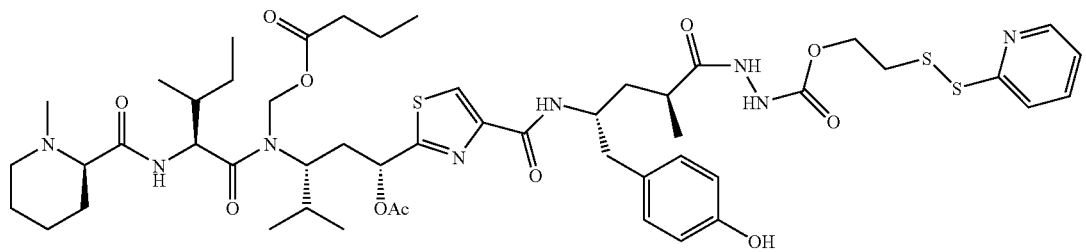 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSc2ccccn2)cs1)C(C)C]

Preparation of tubulysin disulfides (stepwise process). Illustrated for EC0312. DIPEA (36 μL) and isobutyl chloroformate (13 μL) were added with the help of a syringe in tandem into a solution of tubulysin B (82 mg) in anhydrous EtOAc (2.0 mL) at −15° C. After stirring for 45 minutes at −15° C. under argon, to the reaction mixture was added a solution of EC0311 in anhydrous EtOAc (1.0 mL). The resulting solution was stirred under argon at −15° C. for 15 minutes and room temperature for an additional 45 minutes, concentrated, and the residue was purified by flash chromatography (silica gel, 2 to 8% MeOH in DCM) to give EC0312 as a white solid (98 mg). The foregoing method is equally applicable for preparing other tubulysin derivatives by the appropriate selection of the tubulysin starting compound.

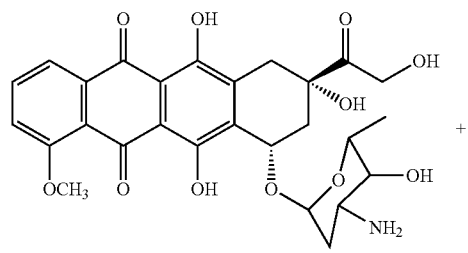

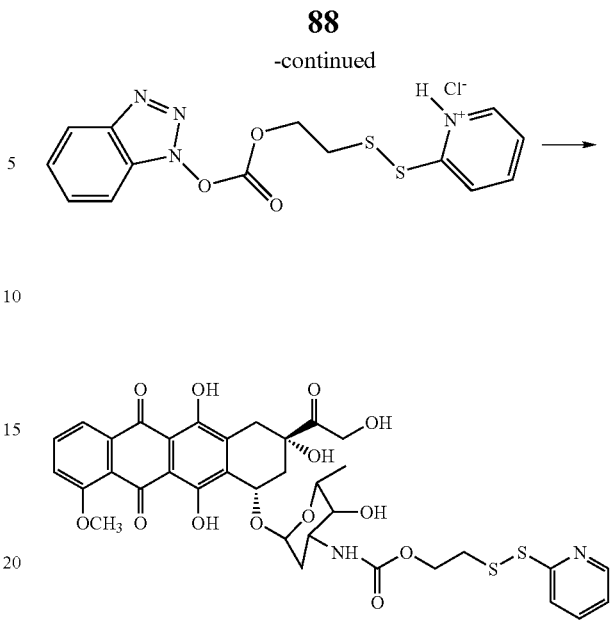

Hydroxydaunorubicin pyridyldisulfide. Similarly, this compound was prepared as described herein in 65% yield, and according to the foregoing scheme.

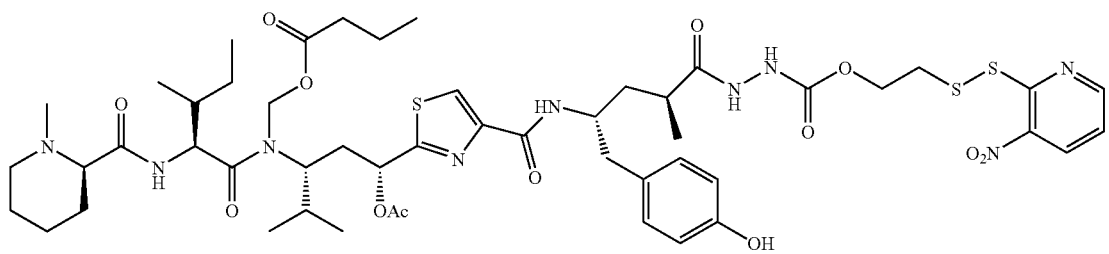 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSc2ncccc2[N+](=O)[O-])cs1)C(C)C]

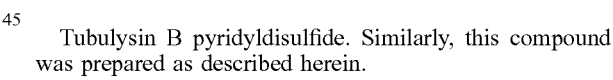

Tubulysin B pyridyldisulfide. Similarly, this compound was prepared as described herein.

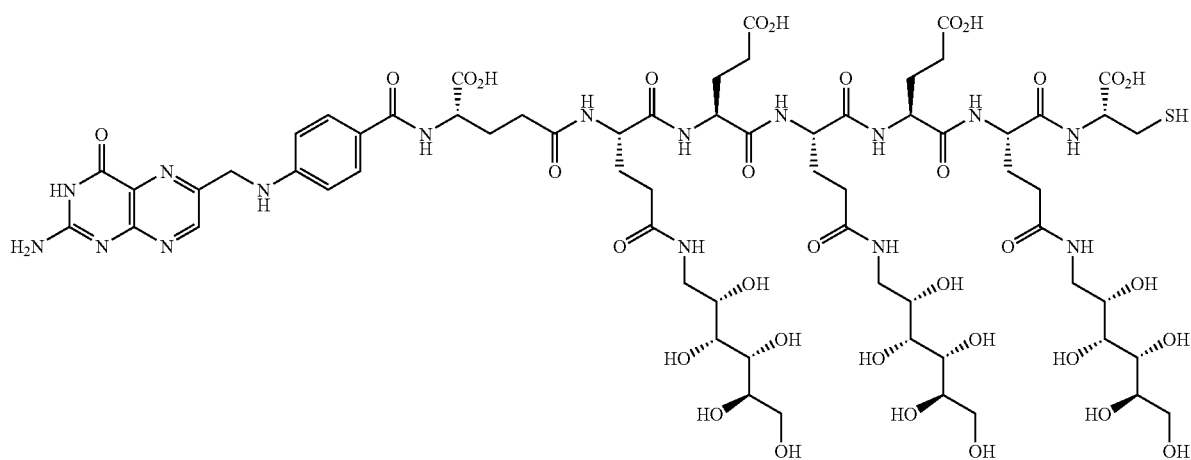 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC0488. This compound was prepared by SPPS according to the general peptide synthesis procedure described herein starting from H-Cys(4-methoxytrityl)-2-chlorotrityl-Resin, and the following SPPS reagents:

| Reagents | mmol | equivalent | MW | amount |
|---|---|---|---|---|
| H-Cys(4-methoxytrityl)-2-chlorotrityl-Resin (loading 0.6 mmol/g) | 0.10 | | | 0.17 g |
| EC0475 | 0.13 | 1.3 | 612.67 | 0.082 g |
| Fmoc-Glu(OtBu)-OH | 0.19 | 1.9 | 425.47 | 0.080 g |
| EC0475 | 0.13 | 1.3 | 612.67 | 0.082 g |
| Fmoc-Glu(OtBu)-OH | 0.19 | 1.9 | 425.47 | 0.080 g |
| EC0475 | 0.13 | 1.3 | 612.67 | 0.082 g |
| Fmoc-Glu-OtBu | 0.19 | 1.9 | 425.47 | 0.080 g |
| $N^{10}$TFA-Pteroic Acid (dissolve in 10 ml DMSO) | 0.16 | 1.6 | 408.29 | 0.066 g |
| DIPEA | | 2.0 eq of AA | | |
| PyBOP | | 1.0 eq of AA | | |

Coupling steps. In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×), IPA (3×), MeOH (3×), and bubble the resin with argon for 30 min.

Cleavage step. Reagent: 92.5% TFA, 2.5% $H_2O$, 2.5% triisopropylsilane, 2.5% ethanedithiol. Treat the resin with cleavage reagent 3× (10 min, 5 min, 5 min) with argon bubbling, drain, wash the resin once with cleavage reagent, and combine the solution. Rotavap until 5 ml remains and precipitate in diethyl ether (35 mL). Centrifuge, wash with diethyl ether, and dry. About half of the crude solid (~100 mg) was purified by HPLC.

HPLC Purification step. Column: Waters Xterra Prep MS C18 10 μm 19×250 mm; Solvent A: 10 mM ammonium acetate, pH 5; Solvent B: ACN; Method: 5 min 0% B to 25 min 20% B 26 mL/min. Fractions containing the product was collected and freeze-dried to give 43 mg EC0488 (51% yield). $^1$H NMR and LC/MS (exact mass 1678.62) were consistent with the product.

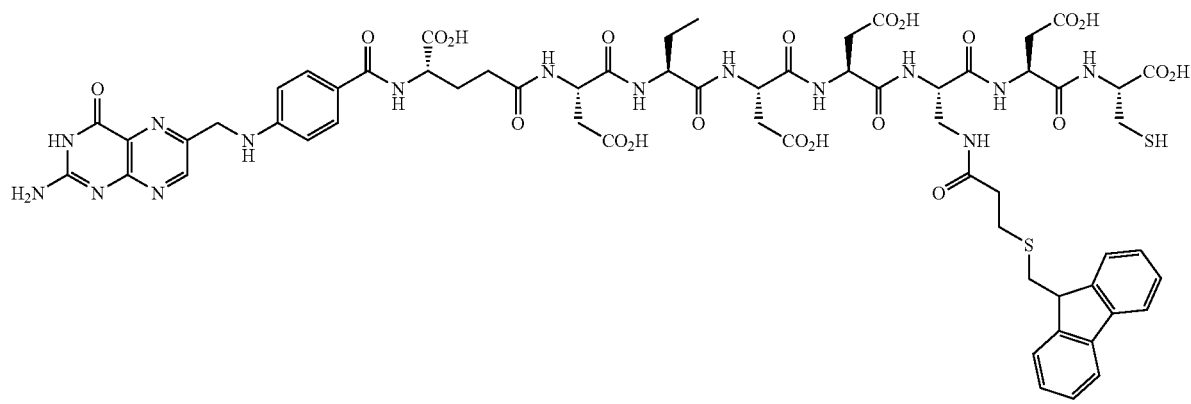 [SMILES: CC[C@H](NC(=O)[C@H](CC(=O)O)NC(=O)CC[C@H](NC(=O)c1ccc(NCc2cnc3nc(N)[nH]c(=O)c3n2)cc1)C(=O)O)C(=O)N[C@@H](CC(=O)O)C(=O)N[C@@H](CC(=O)O)C(=O)N[C@@H](CNC(=O)CCSCC1c2ccccc2-c2ccccc21)C(=O)N[C@@H](CC(=O)O)C(=O)N[C@@H](CS)C(=O)O]

EC0351. Similarly, this compound was prepared as described herein.

General Synthesis of Disulfide Containing Tubulysin Conjugates. Illustrated with pyridinyl disulfide derivatives

B-L-SH +

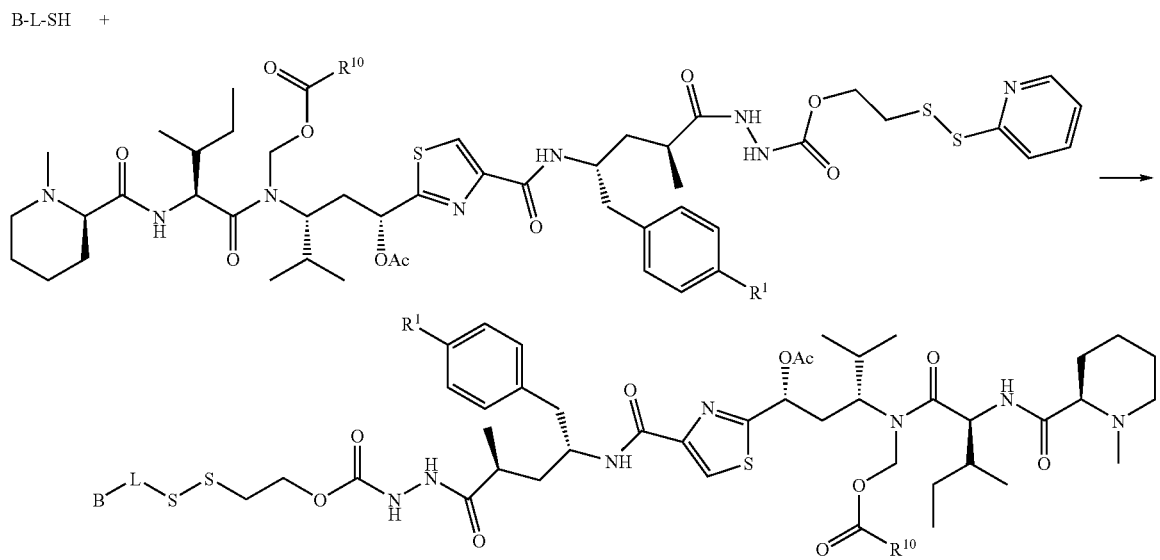

of certain naturally occurring tubulysins, where $R^1$ is H or OH, and $R^{10}$, is alkyl or alkenyl. A binding ligand-linker intermediate containing a thiol group is taken in deionized water (ca. 20 mg/mL, bubbled with argon for 10 minutes prior to use) and the pH of the suspension was adjusted by saturated $NaHCO_3$ (bubbled with argon for 10 minutes prior to use) to about 6.9 (the suspension may become a solution when the pH increased). Additional deionized water is added (ca. 20-25%) to the solution as needed, and to the aqueous solution is added immediately a solution of EC0312 in THF (ca. 20 mg/mL). The reaction mixture becomes homogenous quickly. After stirring under argon, e.g. for 45 minutes, the reaction mixture is diluted with 2.0 mM sodium phosphate buffer (pH 7.0, ca 150 volume percent) and the THF is removed by evacuation. The resulting suspension is filtered and the filtrate may be purified by preparative HPLC (as described herein). Fraction are lyophilized to isolate the conjugates. The foregoing method is equally applicable for preparing other tubulysin conjugates by the appropriate selection of the tubulysin starting compound.

was added a solution of EC0311 (5.8 mg) in anhydrous EtOAc (0.50 mL). The cooling was removed and the reaction mixture was stirred under argon for an additional 45 minutes, concentrated, vacuumed, and the residue was dissolved in THF (2.0 mL). Meanwhile, EC0488 (40 mg) was dissolved in deionized water (bubbled with argon for 10 minutes prior to use) and the pH of the aqueous solution was adjusted to 6.9 by saturated $NaHCO_3$. Additional deionized water was added to the EC0488 solution to make a total volume of 2.0 mL and to which was added immediately the THF solution containing the activated tubulysin. The reaction mixture, which became homogeneous quickly, was stirred under argon for 50 minutes and quenched with 2.0 mM sodium phosphate buffer (pH 7.0, 15 mL). The resulting cloudy solution was filtered and the filtrate was injected into a preparative HPLC for purification. Column: Waters XTerra Prep MS $C_{18}$ 10 μm, 19×250 mm; Mobile phase A: 2.0 mM sodium phosphate buffer, pH 7.0; Mobile phase B: acetonitrile; Method: 1% B for 5 minutes, then 1% B to 60% B over

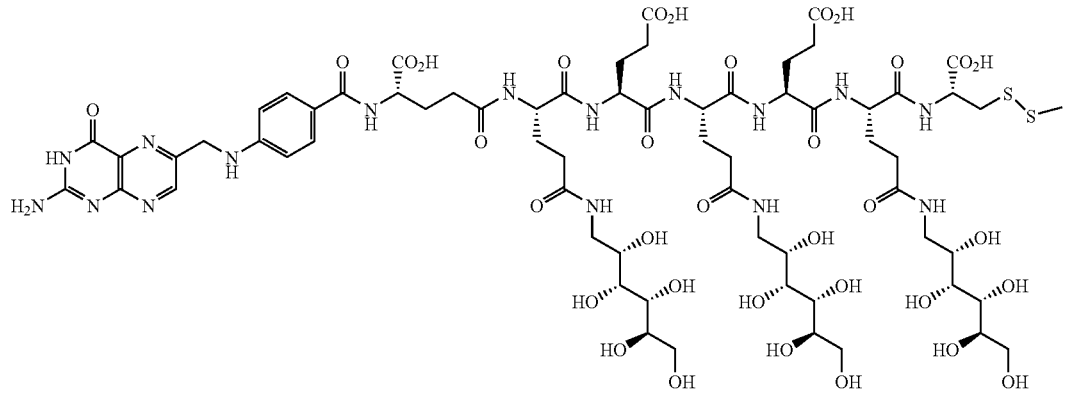

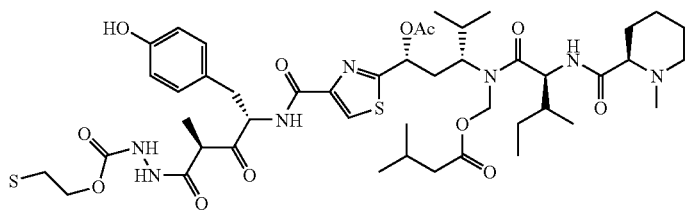

General Method 2 for Preparing Conjugates (one-pot). Illustrated with preparation of EC0543. DIPEA (7.8 μL) and isobutyl chloroformate (3.1 μL) were added with the help of a syringe in tandem into a solution of tubulysin A (18 mg) in anhydrous EtOAc (0.50 mL) at −15° C. After stirring for 35 minutes at −15° C. under argon, to the reaction mixture the next 30 minutes, flow rate=26 mL/min. Fractions from 20.75-24.50 minutes were collected and lyophilized to afford EC0543 as a pale yellow fluffy solid (26 mg). The foregoing method is equally applicable for preparing other tubulysin conjugates by the appropriate selection of the tubulysin starting compound.

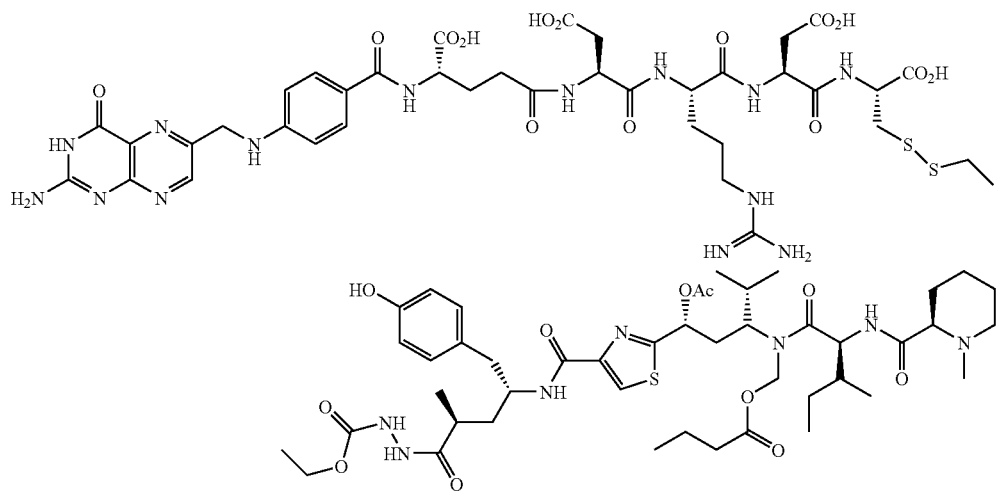

EC0305. EC089 (86 mg) was suspended in deionized water (4.0 mL, bubbled with argon for 10 minutes prior to use) and the pH of the suspension was adjusted by saturated NaHCO$_3$ (bubbled with argon for 10 minutes prior to use) to about 6.9 (the suspension became a solution when the pH increased). Additional deionized water was added to the solution to make a total volume of 5.0 mL and to the aqueous solution was added immediately a solution of EC0312 (97 mg) in THF (5.0 mL). The reaction mixture became homogenous quickly. After stirring under argon for 45 minutes, the reaction mixture was diluted with 2.0 mM sodium phosphate buffer (pH 7.0, 15 mL) and the THF was removed on a Rotavapor. The resulting suspension was filtered and the filtrate was injected into a preparative HPLC for purification (Column: Waters XTerra Prep MS C$_{18}$ 10 μm, 19×250 mm; Mobile phase A: 2.0 mM sodium phosphate buffer, pH 7.0; Mobile phase B: acetonitrile; Method: 5% B to 80% B over 25 minutes, flow rate=25 mL/min). Fractions from 10.04-11.90 minutes were collected and lyophilized to give EC0305 as a pale yellow fluffy solid (117 mg).

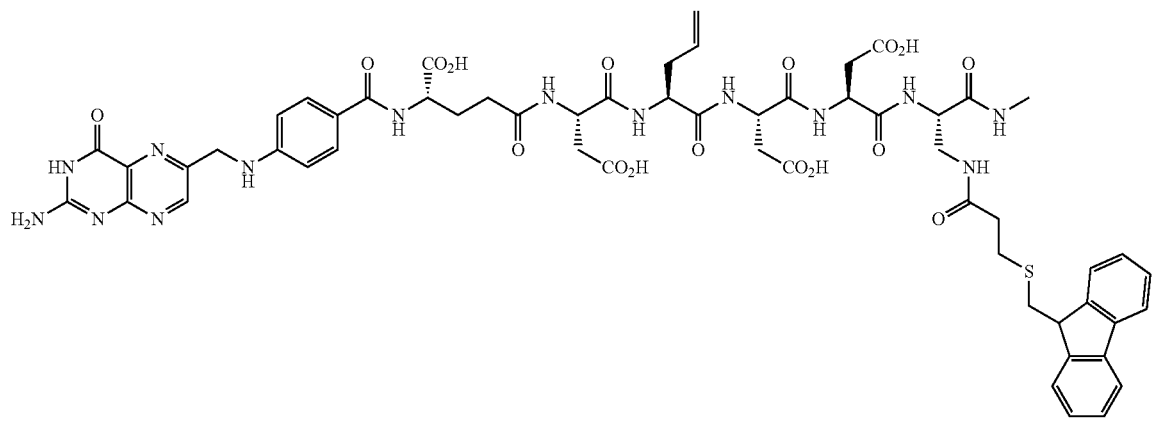

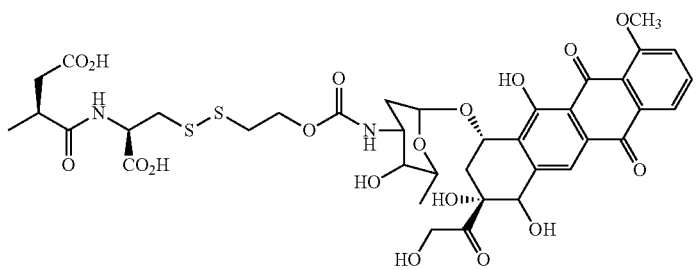

EC0352. Similarly, this compound was prepared as described herein. EC0352 was prepared by forming a disulfide bond between hydroxydaunorubucin pyridyldisulfide and EC0351 in 55% yield.

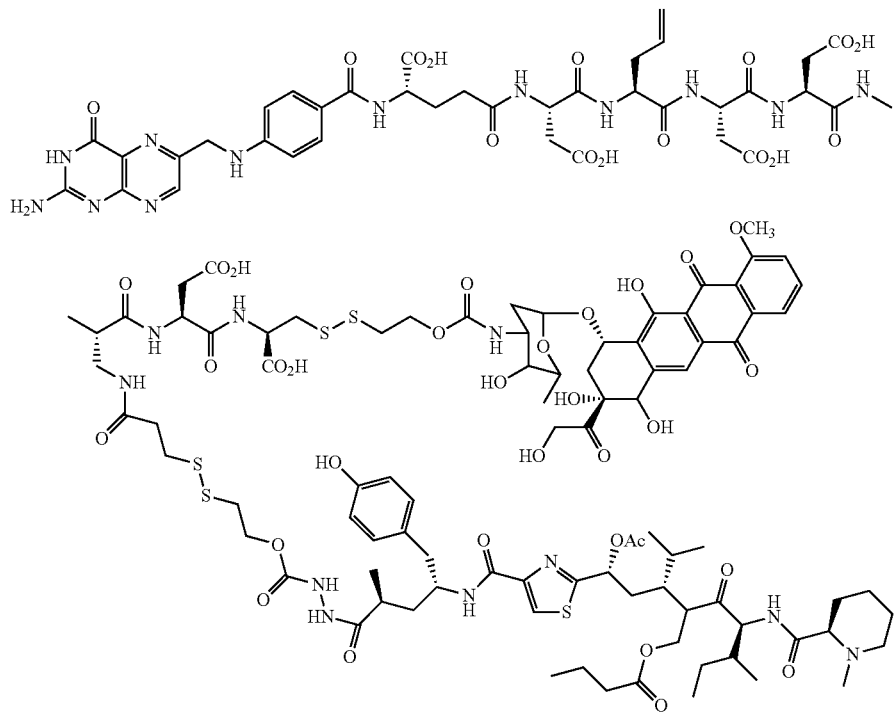

EC0358. Similarly, this compound was prepared as described herein. EC0358 was prepared by forming in DMF/DBU a disulfide bond between EC0352 and tubulysin B pyridyldisulfide in 40% yield.

The following illustrative examples were also prepared using the processes, syntheses, and tubulysins described herein.

97
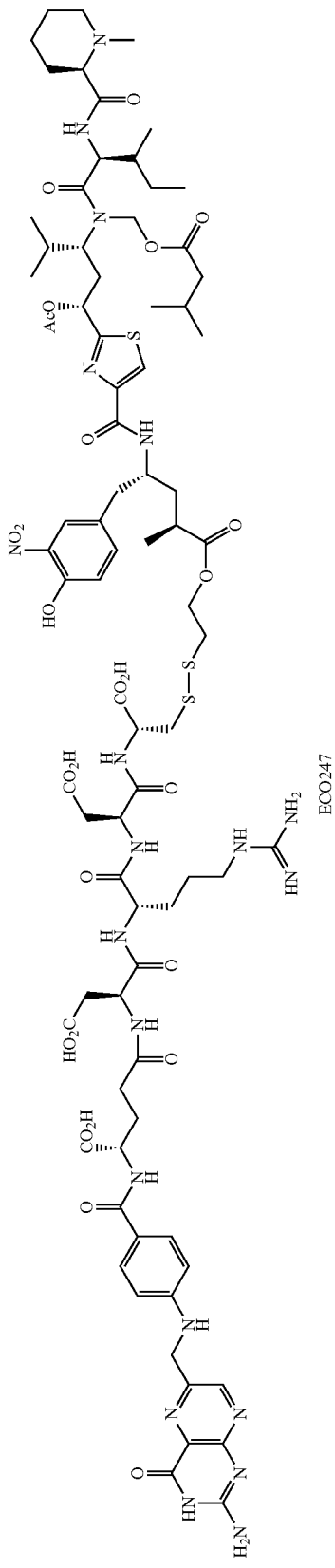
98
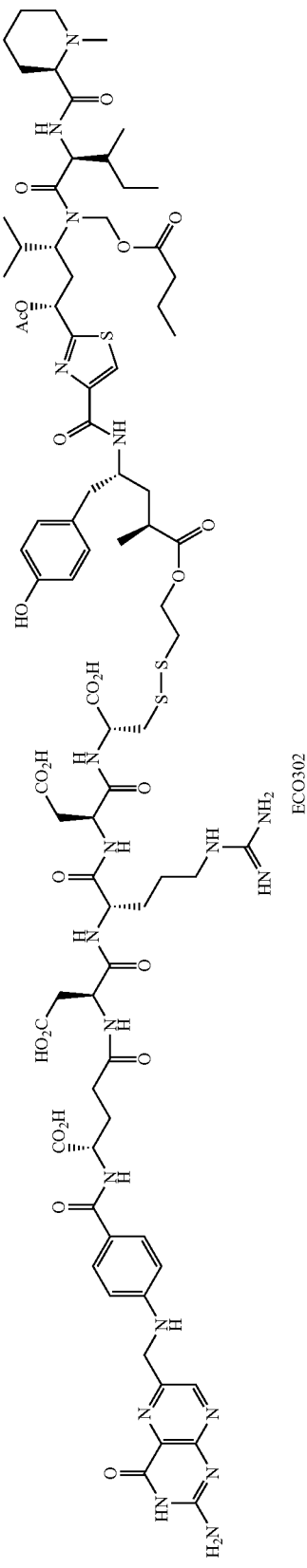
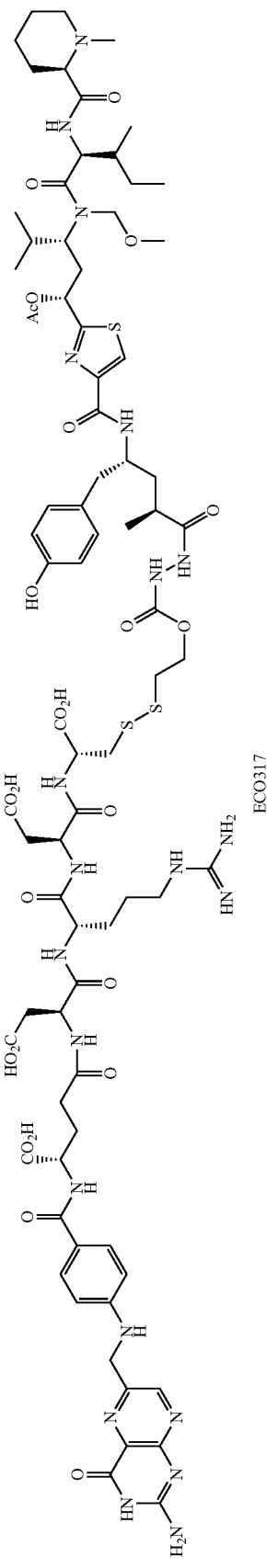

-continued
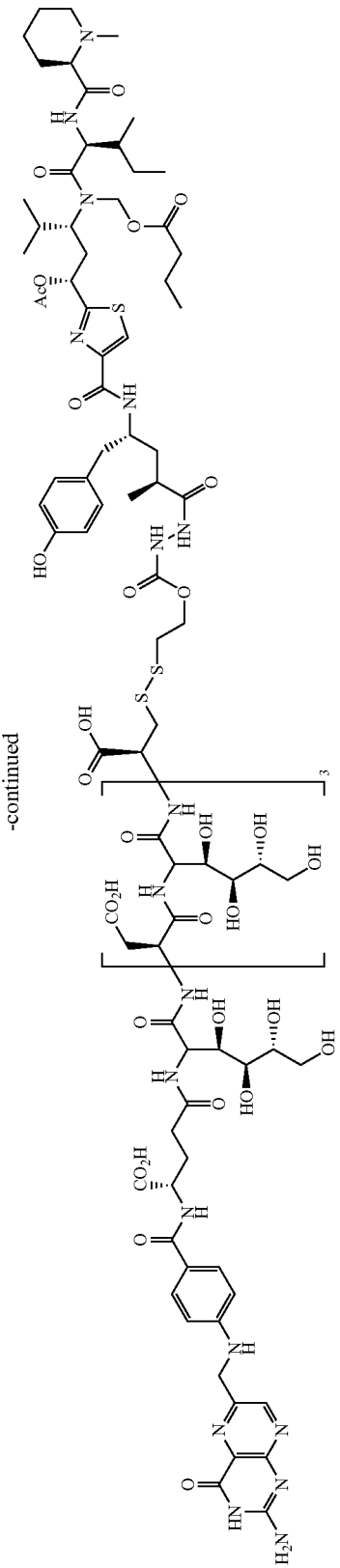
ECO436
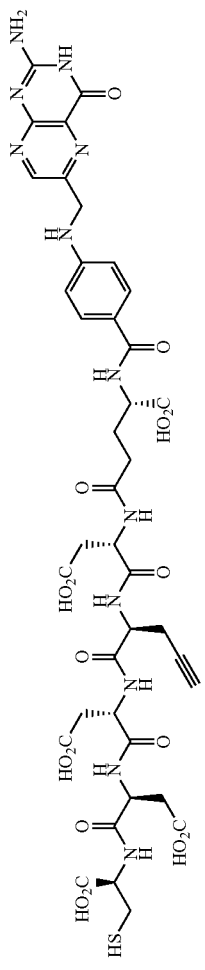
ECO333
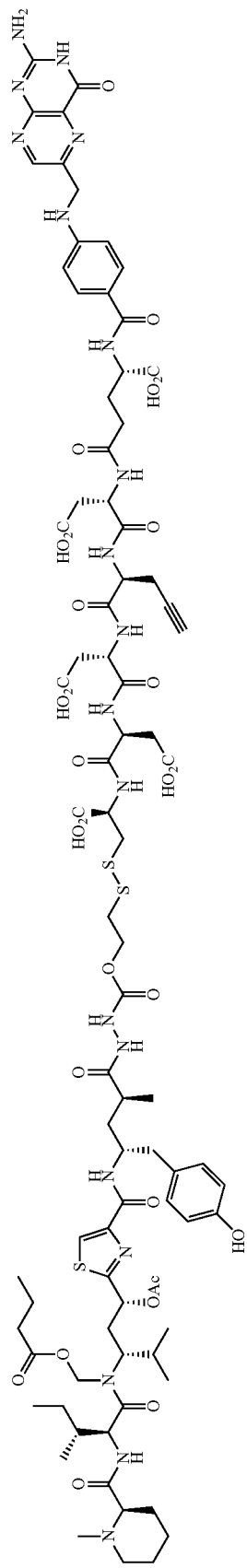
ECO334

-continued
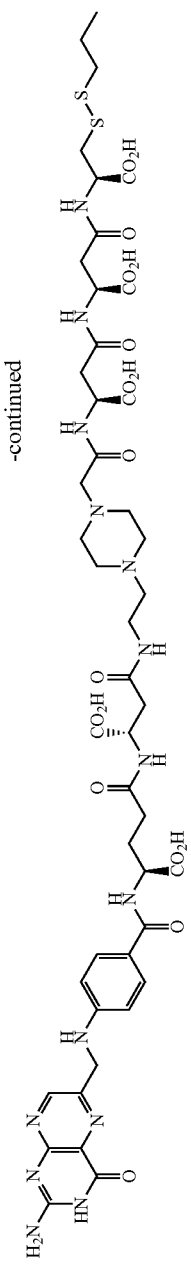
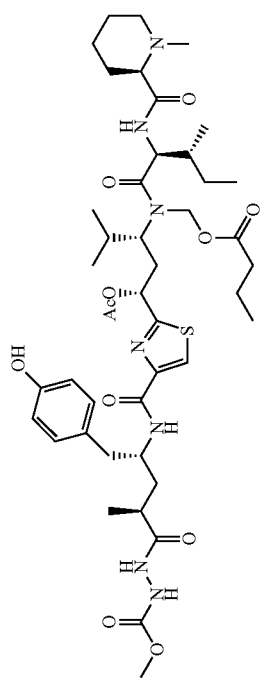
ECO444
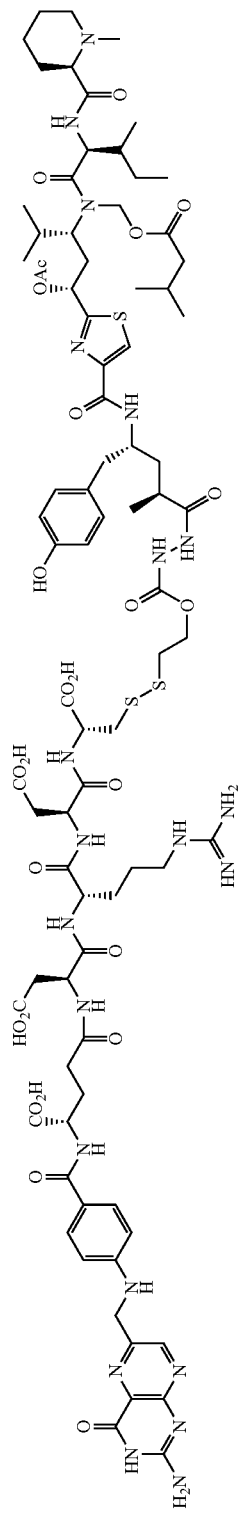
ECO510

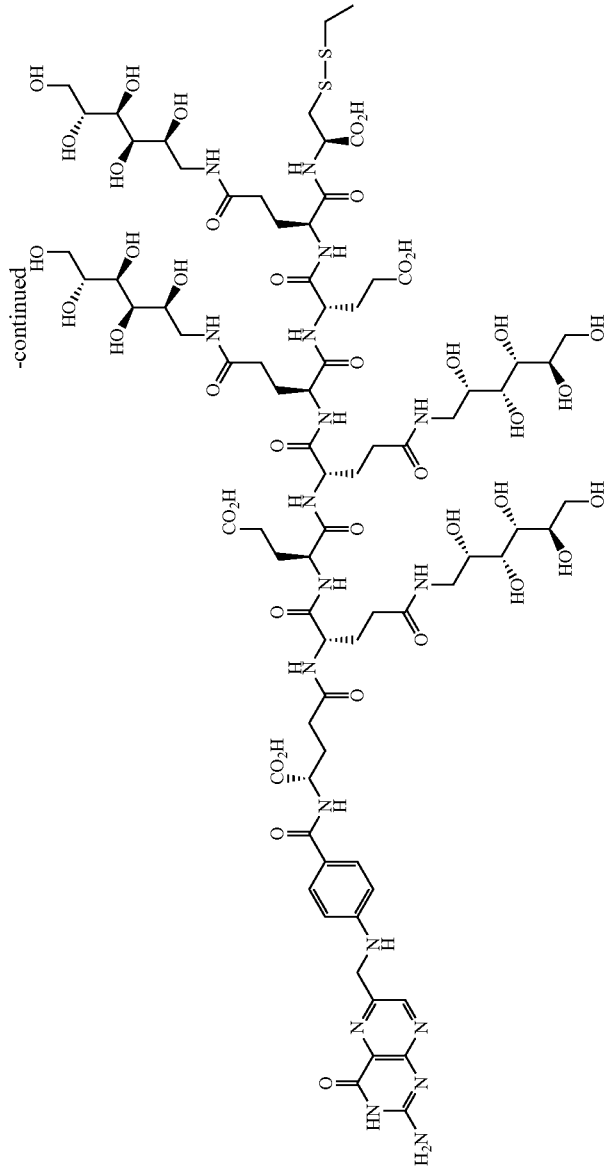
ECO530

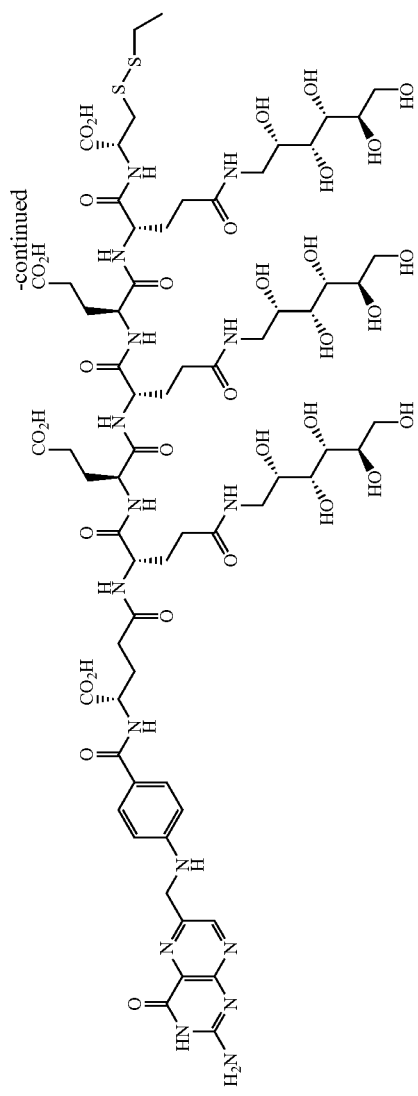
ECO531

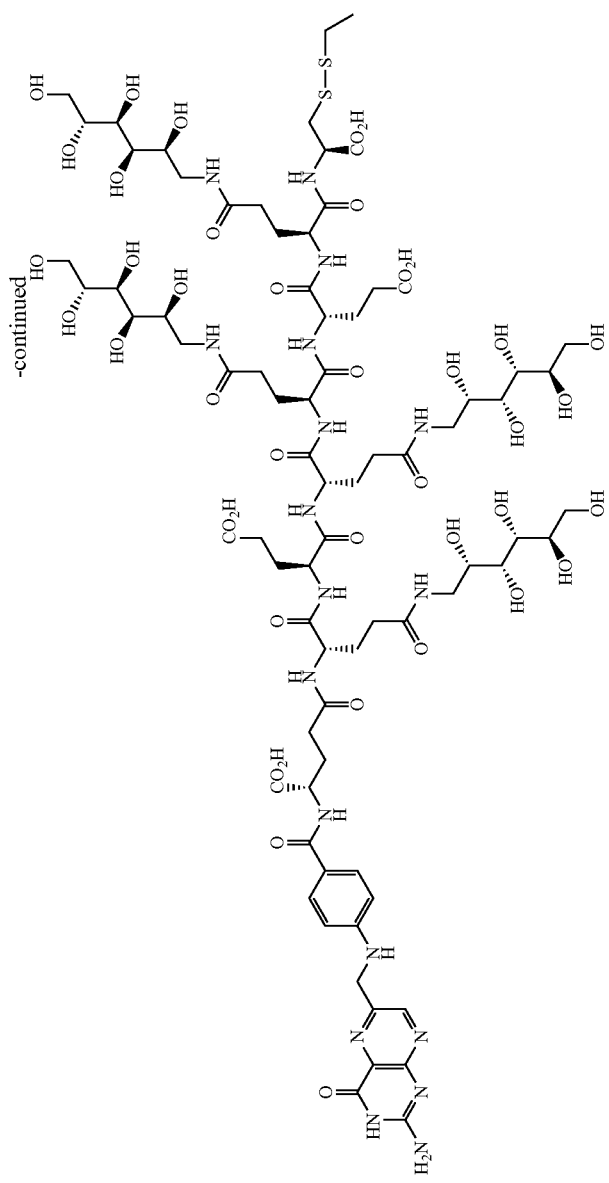

METHOD EXAMPLES

METHOD: Relative Affinity Assay. The affinity for folate receptors (FRs) relative to folate was determined according to a previously described method (Westerhof, G. R., J. H. Schornagel, et al. (1995) Mol. Pharm. 48: 459-471) with slight modification. Briefly, FR-positive KB cells were heavily seeded into 24-well cell culture plates and allowed to adhere to the plastic for 18 h. Spent incubation media was replaced in designated wells with folate-free RPMI (FFRPMI) supplemented with 100 nM $^3$H-folic acid in the absence and presence of increasing concentrations of test article or folic acid. Cells were incubated for 60 min at 37° C. and then rinsed 3 times with PBS, pH 7.4. Five hundred microliters of 1% SDS in PBS, pH 7.4, were added per well. Cell lysates were then collected and added to individual vials containing 5 mL of scintillation cocktail, and then counted for radioactivity. Negative control tubes contained only the $^3$H-folic acid in FFRPMI (no competitor). Positive control tubes contained a final concentration of 1 mM folic acid, and CPMs measured in these samples (representing non-specific binding of label) were subtracted from all samples. Notably, relative affinities were defined as the inverse molar ratio of compound required to displace 50% of $^3$H-folic acid bound to the FR on KB cells, and the relative affinity of folic acid for the FR was set to 1.

Figure 4:
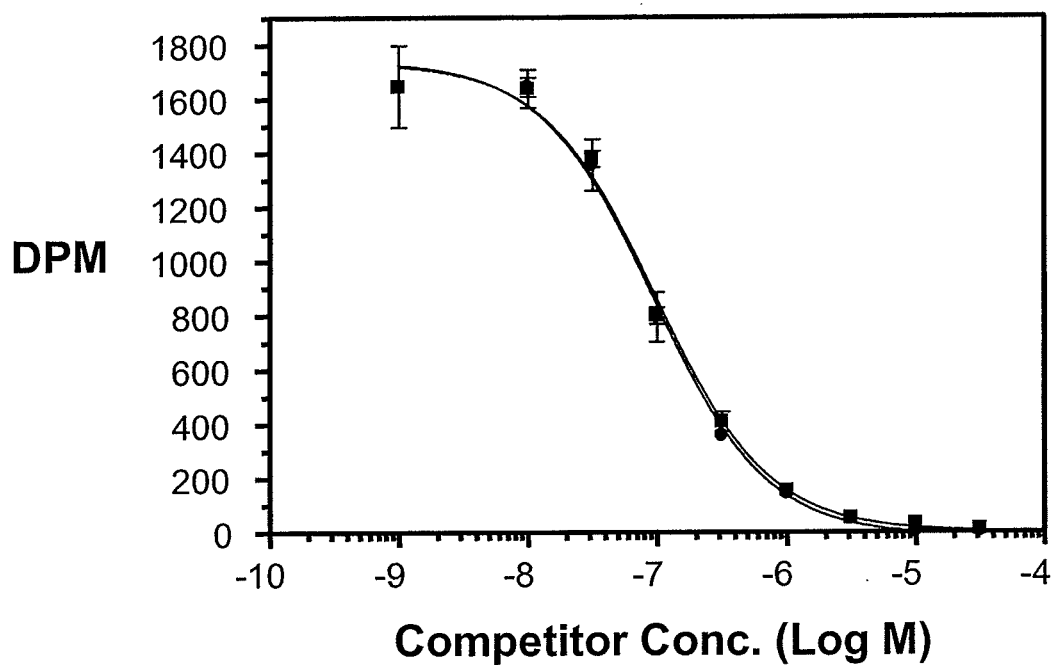
FIG. 4 shows the relative affinity assay results in 10% serum/FDRPMI for EC0305: (●) folic acid, relative affinity=1; (■) EC0305, relative affinity=0.96.

The relative affinity assay results in 10% serum/FDRPMI for EC0305 are shown in the FIG. 4. Compared to folic acid, EC0305 shown 96% relative affinity for the folate receptor.

METHOD: Inhibition of Cellular DNA Synthesis. The compounds described herein were evaluated using an in vitro cytotoxicity assay that predicts the ability of the drug to inhibit the growth of folate receptor-positive KB cells. The compounds were comprised of folate linked to a respective chemotherapeutic drug, as prepared according to the protocols described herein. The KB cells were exposed for up to 7 h at 37° C. to the indicated concentrations of folate-drug conjugate in the absence or presence of at least a 100-fold excess of folic acid. The cells were then rinsed once with fresh culture medium and incubated in fresh culture medium for 72 hours at 37° C. Cell viability was assessed using a $^3$H-thymidine incorporation assay. For compounds described herein, dose-dependent cytotoxicity was generally measurable, and in most cases, the $IC_{50}$ values (concentration of drug conjugate required to reduce $^3$H-thymidine incorporation into newly synthesized DNA by 50%) were in the low nanomolar range. Furthermore, the cytotoxicities of the conjugates were reduced in the presence of excess free folic acid, indicating that the observed cell killing was mediated by binding to the folate receptor.

For example, EC0305 exhibited dose-responsive behavior and specificity for the folate receptor after a 2 hour pulse and a 72 hour chase, as shown in the FIG. 1. The $IC_{50}$ for EC0305 was about 1.5 nM. In addition, the cytotoxic activity of EC0305 was blocked in the presence of an excess of folic acid, as also shown in FIG. 1. Finally, EC0305 displayed no activity against FR-negative cells. These results suggest that EC0305 is acting through a folate selective or folate specific mechanism.

METHOD: In vitro test against the various cancer cell lines. IC50 values were generated for various cell lines and the results are shown in the table below. Cells are heavily seeded in 24-well Falcon plates and allowed to form nearly confluent monolayers overnight. Thirty minutes prior to the addition of the test compound, spent medium is aspirated from all wells and replaced with fresh folate-deficient RPMI medium (FFRPMI). A subset of wells are designated to receive media containing 100 µM folic acid. The cells in the designated wells are used to determine the targeting specificity. Without being bound by theory it is suggested that the cytotoxic activity produced by test compounds in the presence of excess folic acid, i.e. where there is competition for FR binding, corresponds to the portion of the total activity that is unrelated to FR-specific delivery. Following one rinse with 1 mL of fresh FFRPMI containing 10% heat-inactivated fetal calf serum, each well receives 1 mL of medium containing increasing concentrations of test compound (4 wells per sample) in the presence or absence of 100 µM free folic acid as indicated. Treated cells are pulsed for 2 h at 37° C., rinsed 4 times with 0.5 mL of media, and then chased in 1 mL of fresh medium up to 70 h. Spent medium is aspirated from all wells and replaced with fresh medium containing 5 µCi/mL $^3$H-thymidine. Following a further 2 h 37° C. incubation, cells are washed 3 times with 0.5 mL of PBS and then treated with 0.5 mL of ice-cold 5% trichloroacetic acid per well. After 15 min, the trichloroacetic acid is aspirated and the cell material solubilized by the addition of 0.5 mL of 0.25 N sodium hydroxide for 15 min. A 450 µL aliquot of each solubilized sample is transferred to a scintillation vial containing 3 mL of Ecolume scintillation cocktail and then counted in a liquid scintillation counter. Final tabulated results are expressed as the percentage of $^3$H-thymidine incorporation relative to untreated controls.

Results for EC305 are shown in the following table:

| Cell Model | Species | Cancer Type | FR Status | $IC_{50}$ (nM) | Activity Blocked with Excess FA |
|---|---|---|---|---|---|
| KB | Human | Nasophyngeal CA | Positive | 1.5 | Yes |
| OVCAR-3 | Human | Ovarian CA | Positive | 1 | Yes |
| IGROV | Human | Ovarian CA | Positive | 2 | Yes |
| RAW | Mouse | CML | Positive | 2.6 | Yes |
| 4T-1-FR | Mouse | Breast CA | Positive | 10 | Yes |
| 4T-1 Parent | Mouse | Breast | Negative | >1000 | n/a |

Each of the cell lines is commercially available except for 4T-1 parent and 4T-1-FR, which were obtained from Rhone Poulenc Rorer.

Figure 2:
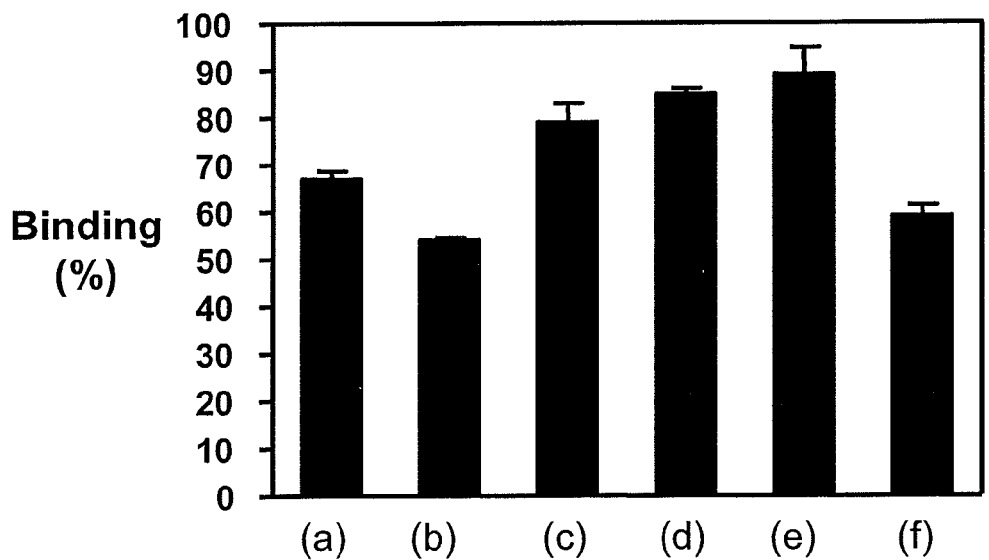
FIG. 2 shows that EC0305 exhibited low serum binding in various species: (a) human, (b) dog, (c) Balb/c mouse, (d) rat, (e) rabbit, and (f) fetal calf serum. Human serum binding was 67%.

METHOD: Serum binding against different species. Compounds are tested with 30K NMWL, subjected to Microcon filtration (10,000 g for 30 minutes), and compounds are detected by HPLC. EC0305 was tested against various animal sera and exhibited low serum binding in various species, as shown in the FIG. 2. In particular, EC0305 showed a low 67% binding in human serum.

Figure 3:
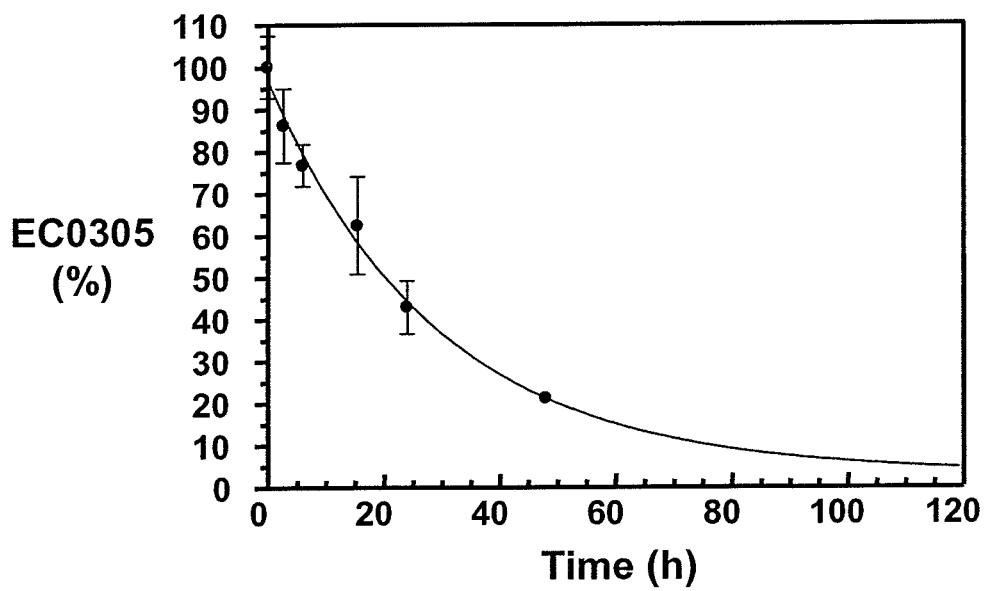
FIG. 3 shows that EC0305 tested in human serum for stability exhibited a half life of about 20 hours.

METHOD: Human serum stability. EC0305 was tested in human serum for stability and exhibited a half life of about 20 hours, as shown in the FIG. 3.

METHOD: Inhibition of Tumor Growth in Mice. Four to seven week-old mice (Balb/c or nu/nu strains) were purchased from Harlan Sprague Dawley, Inc. (Indianapolis, Ind.). Normal rodent chow contains a high concentration of folic acid (6 mg/kg chow); accordingly, mice used were maintained on the folate-free diet (Harlan diet #TD00434) for 1 week before tumor implantation to achieve serum folate concentrations close to the range of normal human serum. For tumor cell inoculation, $1 \times 10^6$ M109 cells (Balb/c strain) or 1×10⁶ KB cells (nu/nu strain) in 100 μL were injected in the subcutis of the dorsal medial area. Tumors were measured in two perpendicular directions every 2-3 days using a caliper, and their volumes were calculated as $0.5 \times L \times W^2$, where L=measurement of longest axis in mm and W=measurement of axis perpendicular to L in mm. Log cell kill (LCK) and treated over control (T/C) values were then calculated according to published procedures (see, e.g., Lee et al., "BMS-247550: a novel epothilone analog with a mode of action similar to paclitaxel but possessing superior antitumor efficacy" *Clin Cancer Res* 7:1429-1437 (2001); Rose, "Taxol-based combination chemotherapy and other in vivo preclinical antitumor studies" *J Natl Cancer Inst Monogr* 47-53 (1993)). Dosing solutions were prepared fresh each day in PBS and administered through the lateral tail vein of the mice. Dosing was initiated when the s.c. tumors had an average volume between 50-100 mm³ ($t_o$), typically 8 days post tumor inoculation (PTI) for KB tumors, and 11 days PTI for M109 tumors.

METHOD: Drug Toxicity determinations. Persistent drug toxicity was assessed by collecting blood via cardiac puncture and submitting the serum for independent analysis of blood urea nitrogen (BUN), creatinine, total protein, AST-SGOT, ALT-SGPT plus a standard hematological cell panel at Ani-Lytics, Inc. (Gaithersburg, Md.). In addition, histopathologic evaluation of formalin-fixed heart, lungs, liver, spleen, kidney, intestine, skeletal muscle and bone (tibia/fibula) were conducted by board-certified pathologists at Animal Reference Pathology Laboratories (ARUP; Salt Lake City, Utah).

METHOD: General KB Tumor Assay. The anti-tumor activity of the compounds described herein, when administered intravenously (i.v.) to tumor-bearing animals, was evaluated in nu/nu mice bearing subcutaneous KB tumors. Approximately 8 days post tumor inoculation in the subcutis of the right axilla with 1×10⁶ KB cells (average tumor volume at $t_o$=50-100 mm³), in mice (5/group) were injected i.v. three times a week (TIW), for 3 weeks with 5 μmol/kg of the drug delivery conjugate or with an equivalent dose volume of PBS (control), unless otherwise indicated. Tumor growth was measured using calipers at 2-day or 3-day intervals in each treatment group. Tumor volumes were calculated using the equation $V = a \times b^2/2$, where "a" is the length of the tumor and "b" is the width expressed in millimeters.

METHOD: General M109 Tumors Assay. The anti-tumor activity of the compounds described herein, when administered intravenously (i.v.) to tumor-bearing animals, was evaluated in Balb/c mice bearing subcutaneous M109 tumors (a syngeneic lung carcinoma). Approximately 11 days post tumor inoculation in the subcutis of the right axilla with 1×10⁶ M109 cells (average tumor volume at $t_o$=60 mm3), mice (5/group) were injected i.v. three times a week (TIW), for 3 weeks with 1500 nmol/kg of the drug delivery conjugate or with an equivalent dose volume of PBS (control). Tumor growth was measured using calipers at 2-day or 3-day intervals in each treatment group. Tumor volumes were calculated using the equation $V = a \times b^2/2$, where "a" is the length of the tumor and "b" is the width expressed in millimeters.

METHOD: General 4T-1 Tumor Assay. Six to seven week-old mice (female Balb/c strain) were obtained from Harlan, Inc., Indianapolis, Ind. The mice were maintained on Harlan's folate-free chow for a total of three weeks prior to the onset of and during this experiment. Folate receptor-negative 4T-1 tumor cells (1×10⁶ cells per animal) were inoculated in the subcutis of the right axilla. Approximately 5 days post tumor inoculation when the 4T-1 tumor average volume was ~100 mm³, mice (5/group) were injected i.v. three times a week (TIW), for 3 weeks with 3 μmol/kg of drug delivery conjugate or with an equivalent dose volume of PBS (control), unless otherwise indicated herein. Tumor growth was measured using calipers at 2-day or 3-day intervals in each treatment group. Tumor volumes were calculated using the equation $V = a \times b^2/2$, where "a" is the length of the tumor and "b" is the width expressed in millimeters.

METHOD: Toxicity as Measured by Weight Loss. The percentage weight change of the mice was determined in mice (5 mice/group) on selected days post-tumor inoculation (PTI), and graphed.

METHOD: Alternate dosing schedule. Each of the foregoing assays may be modified as follows: approximately 8 days post tumor inoculation in the subcutis of the right axilla with 1×10⁶ KB cells (average tumor volume at $t_o$=50-100 mm³), mice (5/group) are injected i.v. three times a week (TIW), for 3 weeks with a drug delivery conjugate described herein, or with an equivalent dose volume of PBS as control. Tumor growth is measured using calipers at 2-day or 3-day intervals in each treatment group. Tumor volumes were calculated using the equation $V = a \times b^2/2$, where "a" is the length of the tumor and "b" is the width expressed in millimeters.

METHOD: Alternate dosing schedule. Each of the foregoing assays may be modified as follows: approximately 8 days post tumor inoculation in the subcutis of the right axilla with 1×10⁶ KB cells (average tumor volume at $t_o$=50-100 mm³), mice (5/group) are injected i.v. five times a week on Monday through Friday for 2 or 3 weeks with a drug delivery conjugate described herein, or with an equivalent dose volume of PBS as control. Tumor growth is measured using calipers at 2-day or 3-day intervals in each treatment group. Tumor volumes were calculated using the equation $V = a \times b^2/2$, where "a" is the length of the tumor and "b" is the width expressed in millimeters.

Figure 5:
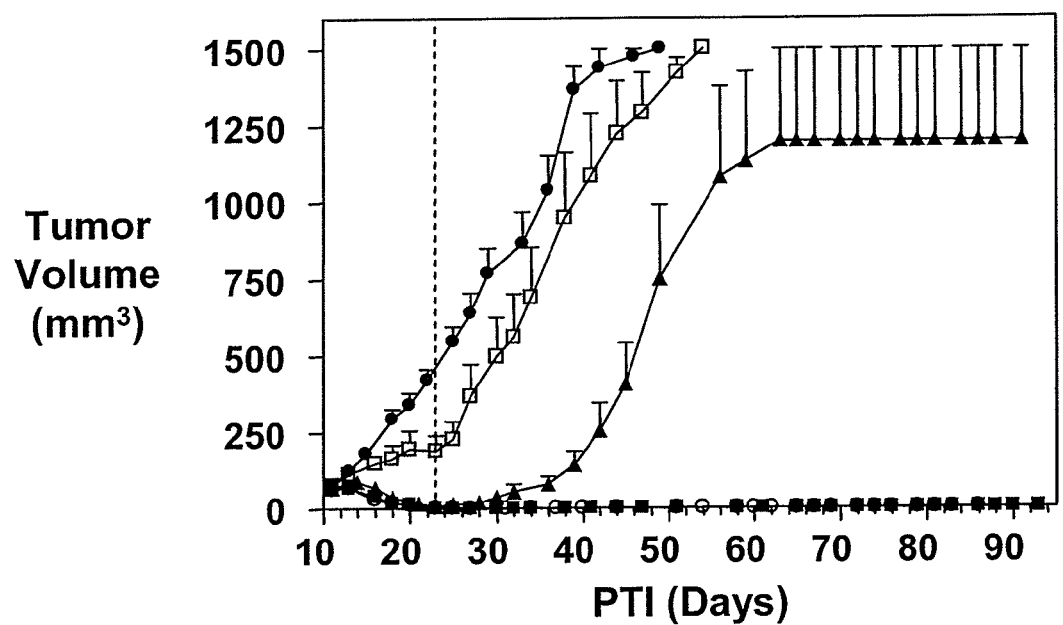
FIG. 5 shows the activity of EC305 against KB tumors dosed three times per week (TIW) post tumor inoculation (PTI) on a two week schedule at various doses, as compared to controls: (●) PBS treated control; (○) EC0305 2 μmol/kg TIW (5/5 complete responses); (■) EC0305 1 μmol/kg TIW (5/5 complete responses); (▲) EC0305 0.5 μmol/kg TIW (1/5 complete responses); (□) EC0305 1 μmol/kg TIW+EC-20 (rhenium) 40 μmol/kg TIW (0/5 complete responses). The vertical dotted line indicates the last day of dosing.

EC305 was tested at TIW on a two week schedule at various doses, and showed complete responses in 5 of 5 animals tested at a dose at or above 1 μmol/kg, as shown in the FIG. 5. In FIG. 5, the vertical dotted line indicates the last day of dosing. In addition, no recurrence or regrowth of the tumors was observed during the entire observation period for those doses in 5 of 5 animals, despite that the last administration of conjugate was given more than 70 days earlier, as also shown in the FIG. 5. In contrast, as also shown in the FIG. 5, the anti-tumor activity of EC0305 was completely abolished (0/5 responses) in EC0305-treated animals that were co-dosed with a competing but tumor inactive folate-containing analog EC20 (rhenium complex). EC20 (rhenium complex) is the compound of the formula

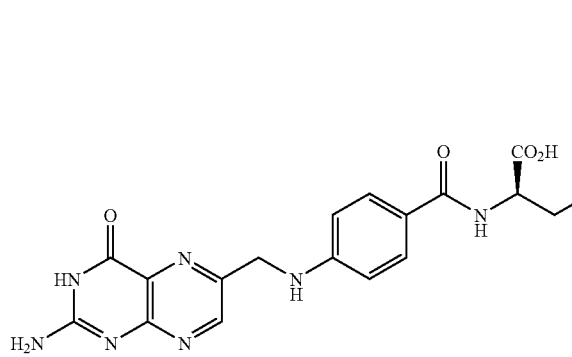
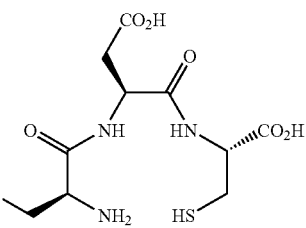

chelated to Rhenium. The preparation of EC20 is described in U.S. patent application publication no. US 2004/0033195 A1, the synthetic procedure description of which is incorporated herein by reference. It is believed that EC20 acts as a competitor of folate targeted conjugates, such as EC0305 at folate receptors, and that therefore the results show the specificity of the effects of EC0305 in targeting the folate receptor.

Figure 6:
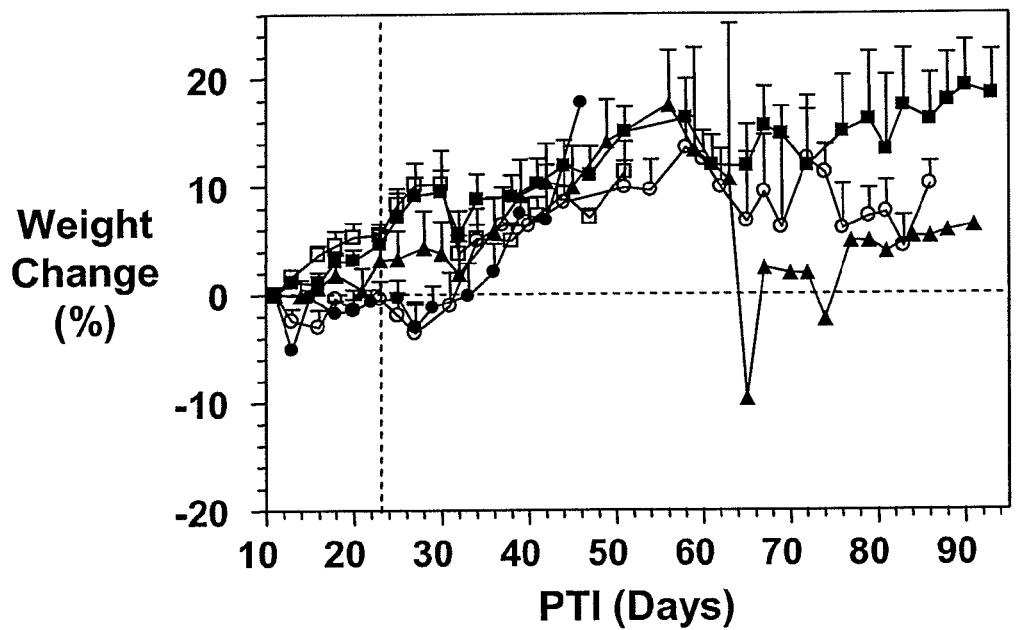
FIG. 6 shows the measure of percent weight change in treated animals, as compared to controls: (●) PBS treated control; (○) EC0305 2 μmol/kg TIW; (■) EC0305 1 μmol/kg TIW; (▲) EC0305 0.5 μmol/kg TIW; (□) EC0305 1 μmol/kg TIW+EC-20 (rhenium) 40 μmol/kg TIW. The vertical dotted line indicates the last day of dosing.

In addition, the observed activity occurred in the apparent absence of weight loss or major organ tissue degeneration, as shown in the FIG. 6, where the vertical dotted line indicates the last day of dosing.

Figure 7:
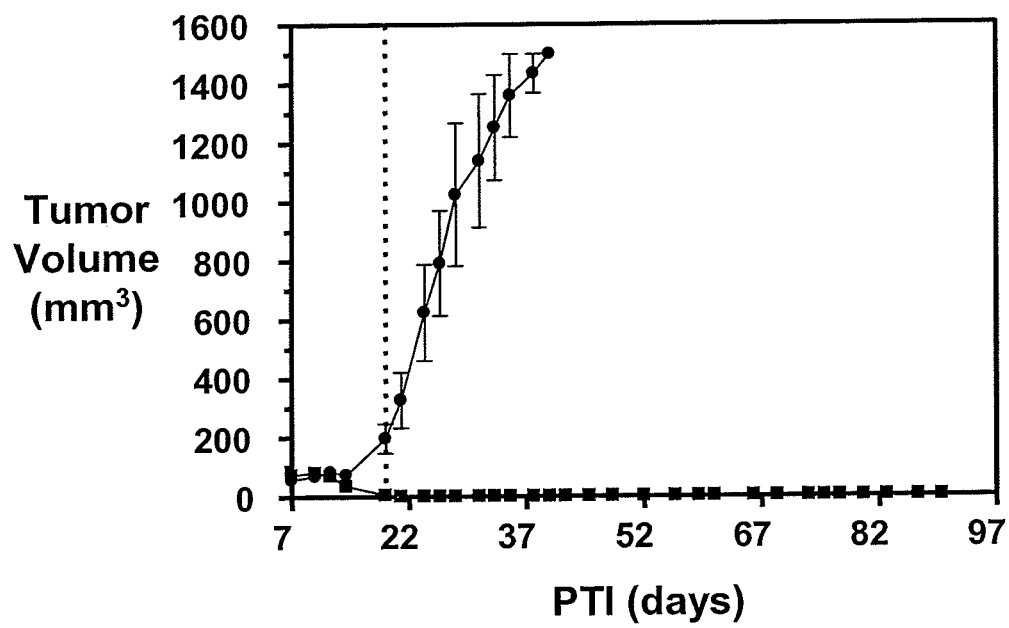
FIG. 7 shows the activity of EC305 against M109 tumors dosed at 2 μmol/kg TIW on a two week schedule at various doses, as compared to controls: (●) PBS treated control; (■) EC0305 (5/5 complete responses). The vertical dotted line indicates the last day of dosing.
Figure 8:
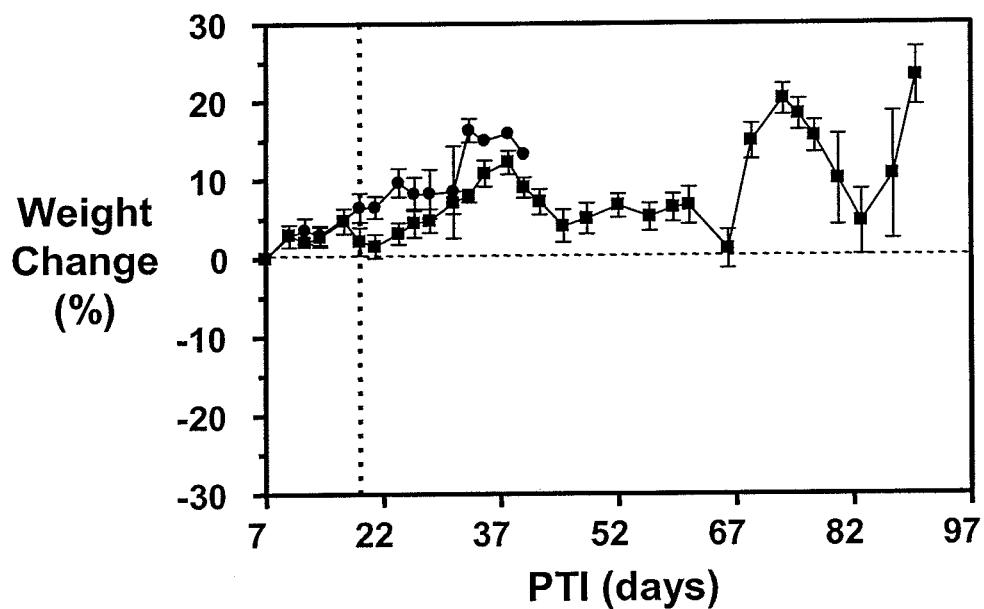
FIG. 8 shows the measure of percent weight change in treated animals, as compared to controls: (●) PBS treated control; (■) EC0305. The vertical dotted line indicates the last day of dosing.

EC305 was repeat tested at 2 μmol/kg TIW on a two week schedule and again showed complete responses in 5 of 5 animals tested. In addition, no recurrence or regrowth of the tumors was observed in 5 of 5 animals during the entire observation period of greater than 90 days, as shown in the FIG. 7. In addition, the observed activity occurred in the apparent absence of weight loss or major organ tissue degeneration, as shown in the FIG. 8.

EC0305 activity was evaluated against FR-positive tumors in mice. Balb/c mice bearing subcutaneous M109 tumors were treated intravenously with EC0305, and in this therapy, complete responses were observed in 5 of 5 test animals. In addition, even after more than 90 days post tumor implantation, and more than 70 days after treatment was discontinued, 5 of 5 test animals remained free of any measurable amounts of tumor. No recurrence or regrowth of the tumors was observed in 5 of 5 animals. Moreover, this observed activity in complete response and non-recurrence of disease, occurred in the apparent absence of weight loss or major organ tissue degeneration. The potency of EC0305 across tumor types was confirmed in a human KB xenograft-nu/nu mice cancer model, as described herein. EC0305 again displayed remarkable anti-tumor activity (5/5 complete responses) in the apparent absence of weight loss or major organ tissue degeneration.

In contrast to the results observed for the conjugates described herein, the unconjugated tubulysin B free drug

Figure 9:
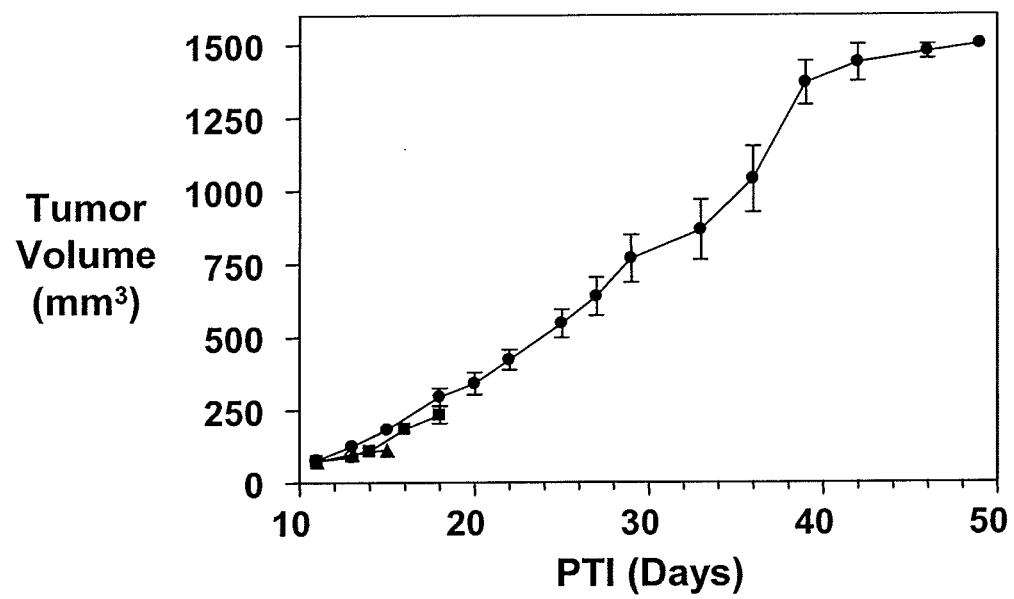
FIG. 9 shows that absence of efficacy (0/5 complete or partial responses) of unconjugated tubulysin B at both tolerable and highly toxic dose levels, as compared to controls: (●) PBS treated control; (○) 0.5 μmol/kg TIW; (▲) 0.2 μmol/kg TIW; (■) 0.1 μmol/kg TIW.
Figure 10:
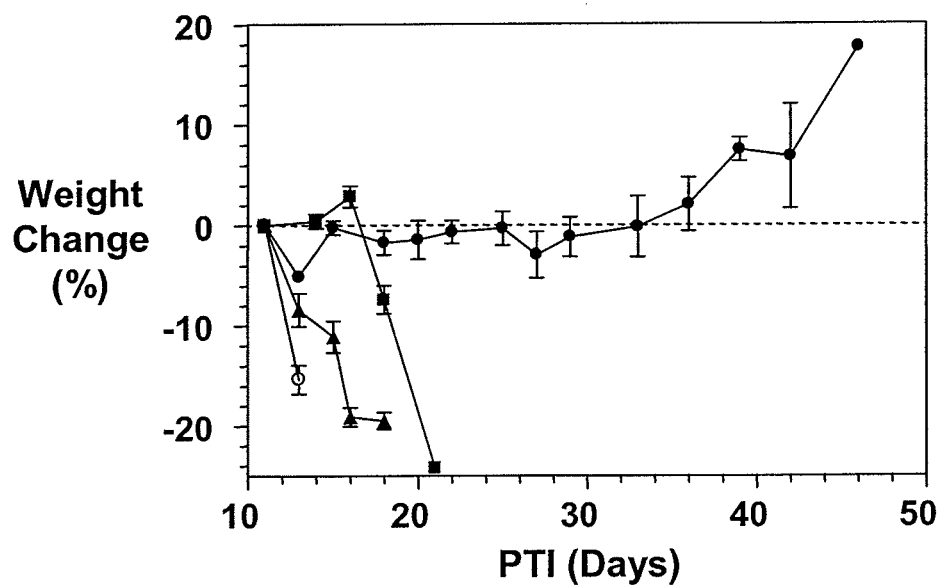
FIG. 10 shows the percent weight change of animals treated with both tolerated and highly toxic dose levels of unconjugated tubulysin B, as compared to controls: (●) PBS treated control; (○) 0.5 μmol/kg TIW; (▲) 0.2 μmol/kg TIW; (■) 0.1 μmol/kg TIW.

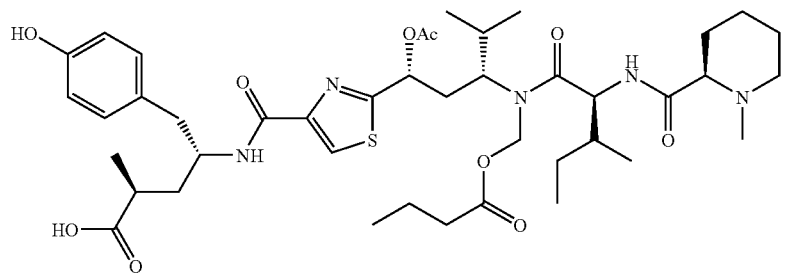 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)O)cs1)C(C)C]

was found to be completely inactive (0/5 responses) at both tolerable and highly toxic dose levels, as shown in the FIG. 9 (dosing was terminated early in each cohort due to excessive toxicity of the unconjugated drug). FIG. 10 shows the dramatic change in percent body weight of animals treated with unconjugated tubulysin B, as compared to controls. As indicated in FIGS. 9 and 10, dosing was terminated early in each cohort due to excessive toxicity of the unconjugated drug.

In addition, the tubulysin conjugate EC0305 was found to be more efficacious than another folate targeted compound, EC145 having the following structure

Figure 11:
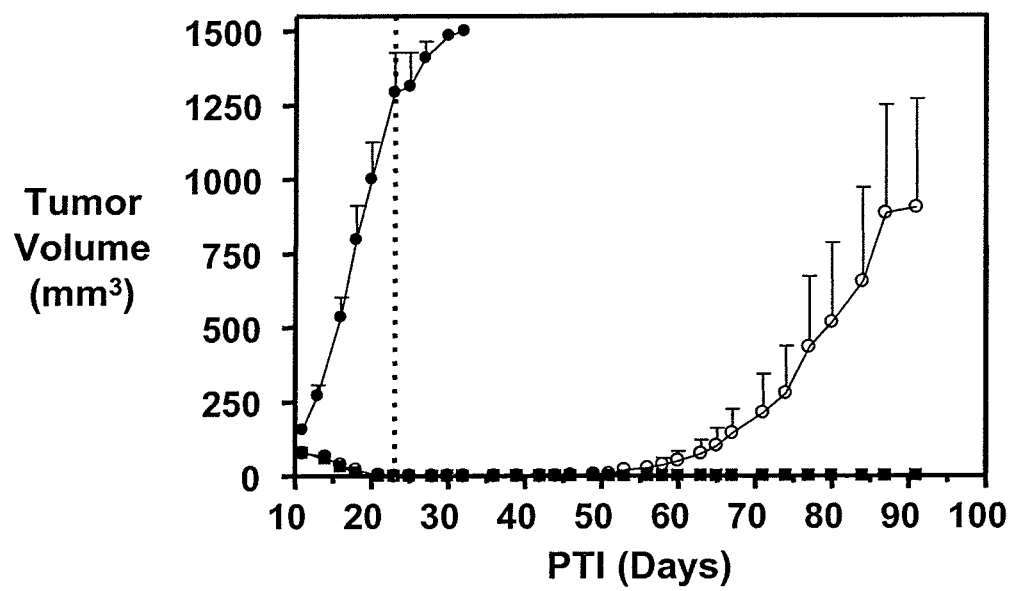
FIG. 11 shows the relative activity of tubulysin conjugate EC0305 compared to vinca alkaloid conjugate EC145, each dosed at 2 μmol/kg TIW on a two-week schedule, and as compared to controls: (●) PBS treated control; (○) EC145 (2/5 complete responses); (■) EC0305 (5/5 complete responses). The vertical dotted line indicates the last day of dosing.

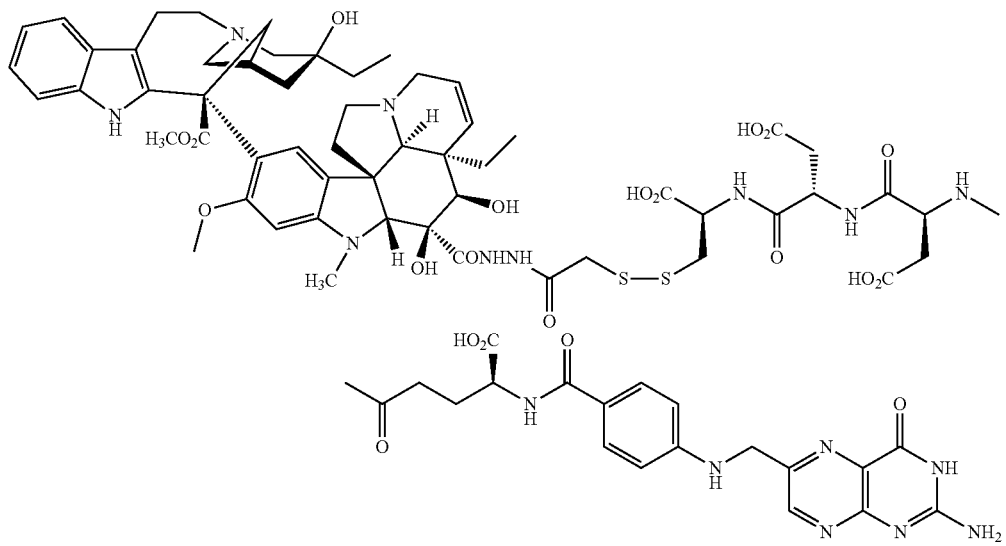

where the drug payload in the latter is a vinca alkaloid. Each was dosed at 2 μmol/kg TIW on a two-week schedule, where the vertical line indicates the last day of dosing, as shown in the FIG. 11. The vinca conjugate EC145 showed 2 of 5 complete responses in treated animals, while the tubulysin conjugate EC0305 showed 5 of 5 complete responses. In addition, no recurrence or regrowth of the tumors was observed in 5 of 5 animals treated with EC0305 over the entire 90 plus day observation period.

Figure 12:
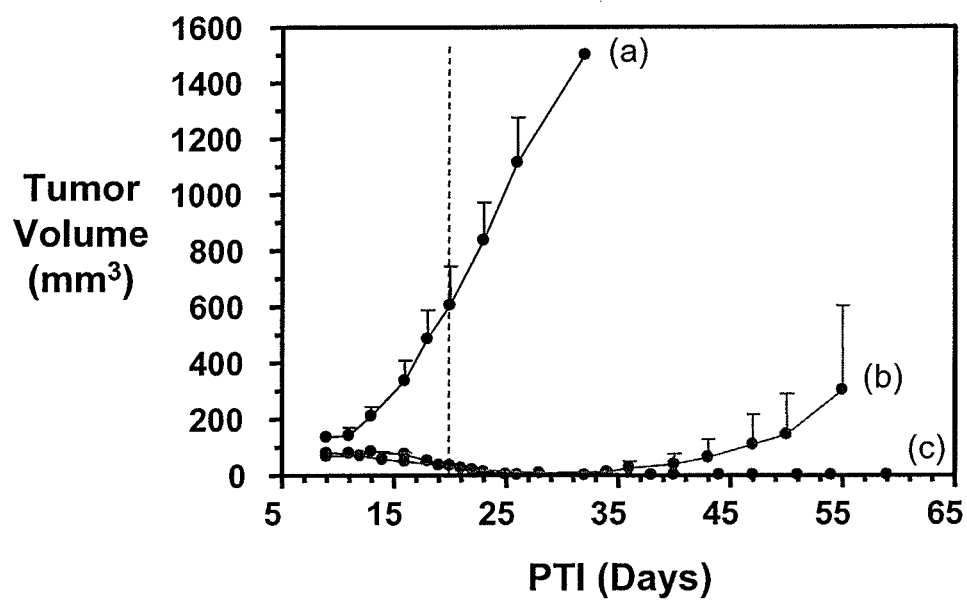
FIG. 12 shows the relative activity of tubulysin conjugates, EC0305 and EC0436, on M109 tumors, each dosed at 2 μmol/kg three times per week for two weeks, as compared to controls: (a) PBS treated control; (b) EC0305 (4/5 complete responses); (c) EC0436 (5/5 complete responses). The vertical dotted line indicates the last day of dosing.
Figure 13:
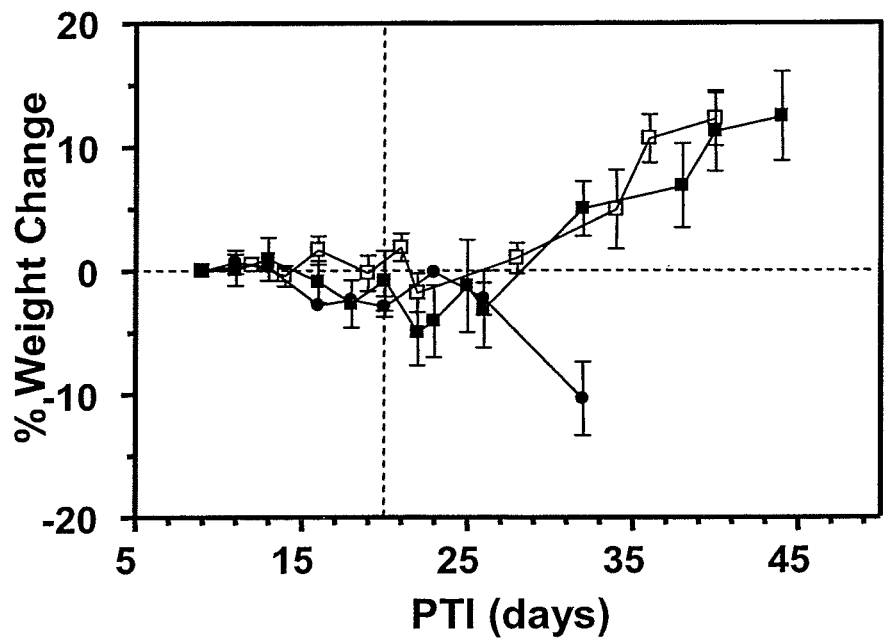
FIG. 13 shows the measure of percent weight change in treated animals, as compared to controls: (●) PBS treated control; (□) is EC0305 (TIW 2 μmol/kg, 2 wks); (■) is EC0436 (TIW 2 μmol/kg, 2 wks). The vertical dotted line indicates the last day of dosing.

FIG. 12 shows the relative activity of two different tubulysin conjugates, EC0305 and EC0436, on M109 tumors compared to controls. Treatment was initiated approximately 11 days after tumor implantation, and each test animal received 2 μmol/kg of EC0305 or EC0436 three times per week for two weeks. The vertical dotted line in FIG. 12 shows that the last day of dosing was on day 20. As shown in FIG. 12, both EC0305 and EC0436 showed complete responses in all animals. However, near about day 35 PTI, the EC0305 treated animals began to show tumor regrowth. In contrast, the EC0436 treated animals not only showed complete responses in 5 of 5 treated animals, but there was no tumor recurrence or regrowth observed in the entire 60-plus day observation period. FIG. 13 shows the percent weight change in treated animals, as compared to controls. In all treated animals, the observed efficacy was not accompanied by any observed gross toxicity as determined by changes in weight of the test animals.

Figure 14:
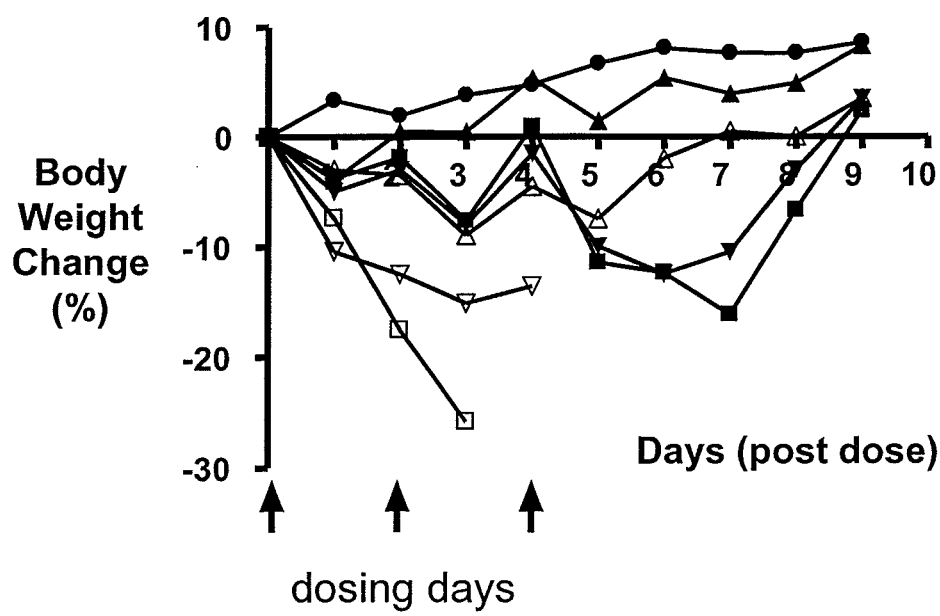
FIG. 14 shows the percentage body weight change of Balb/c mice treated intravenously three times in a week for one week with EC0436 and EC0305 at various doses, as compared to controls: (●) PBS treated control; (▲) 2 μmol/kg TIW EC0436; (▼) 2.5 μmol/kg TIW EC0436; (■) 3 μmol/kg TIW EC0436; (Δ) 2 μmol/kg TIW EC0305; (▽) 2.5 μmol/kg TIW EC0305; (□) 3 μmol/kg EC0305. The vertical dotted line indicates the last day of dosing.

FIG. 14 shows the relative toxicity of two different tubulysin conjugates, EC0305 and EC0436, at doses above their therapeutic doses, as compared to PBS treated controls (●). Each dose was administered three times, every other day, as indicated by the arrows. EC0305 was administered at (Δ) 2 μmol/kg TIW; (∇) 2.5 μmol/kg TIW; and (□) 3 μmol/kg. EC0436 was administered at (▲) 2 μmol/kg TIW; (▼) 2.5 μmol/kg TIW; and (■) 3 μmol/kg TIW. The data suggests that EC0436 may have a higher therapeutic index than EC0305. As shown in FIG. 12, EC0305 provides 4 of 5 complete responses at 2 μmol/kg, while EC0436 provides 5 of 5 complete responses at the same dose. However, EC0305 begins to show toxicity, as determined by changes in weight of the test animals and as shown in FIG. 14, at doses at or above 2.5 μmol/kg. In contrast, no toxicity, as determined by changes in weight of the test animals, was observed with EC0436 even at the highest dose of 3 μmol/kg.

The foregoing exemplary embodiments are set forth to provide a more detailed description of certain aspects of the invention described herein. However, the foregoing are intended to be illustrative and accordingly should not be construed as limiting the invention in any way.

What is claimed is:

1. A drug delivery conjugate B-L-D of the formula

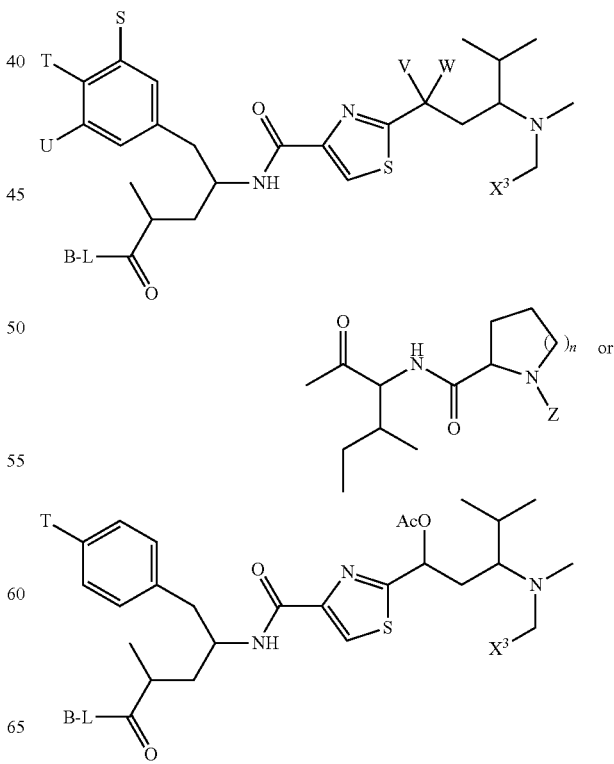

-continued

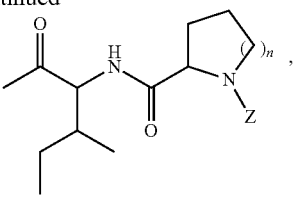

wherein:

n is an integer from 1 to 3;

V is H, $OR^2$, or halo, and W is H, $OR^2$, or alkyl, wherein $R^2$ is independently selected from H, alkyl, or $C(O)R^3$, wherein $R^3$ is alkyl, alkenyl or aryl, provided that $R^2$ is not H when both V and W are $OR^2$; or V and W are taken together with the attached carbon to form a carbonyl;

Z is alkyl or $C(O)R^4$, wherein $R^4$ is alkyl, $CF_3$, or aryl;

T is H or $OR^6$, wherein $R^6$ is H, alkyl, aryl, $COR^7$, $P(O)(OR^8)_2$, or $SO_3R^8$, wherein $R^7$ and $R^8$ are independently selected from the group consisting of H, alkyl, alkenyl, cycloalkyl, heterocyclyl, aryl, and arylalkyl, each of which is optionally substituted, or $R^8$ is a metal cation;

S1 and U are each independently selected from the group consisting of H, halo, nitro, cyano, alkyl, haloalkyl, alkoxy, and haloalkoxy; and $X^3$ is halogen, $OS(O)_2R^{10}$, $OP(O)(OR^{10a})R^{10}$, or $OP(O)(OR^{10a})_2$; wherein $R^{10}$ and $R^{10a}$ are each independently selected from the group consisting of H, alkyl, alkenyl, cycloalkyl, aryl, and arylalkyl, each of which is optionally substituted, or $R^{10a}$ is a metal cation;

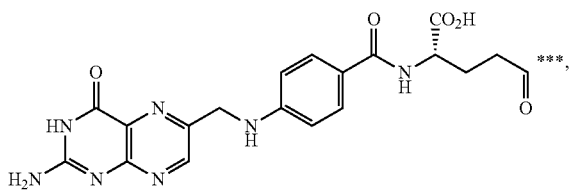

B is of the formula wherein *** represents the point of attachment to the rest of the conjugate;

L is a bivalent linker comprising at least one releasable linker that is not a disulfide releasable linker and at least one spacer linker of the formula

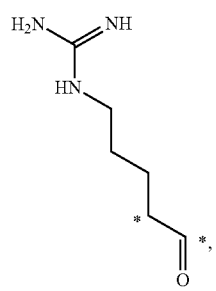

wherein * represents the point of attachment of one or more additional spacer linkers, one or more releasable linkers, D, or B; and D is a tubulysin of the formula

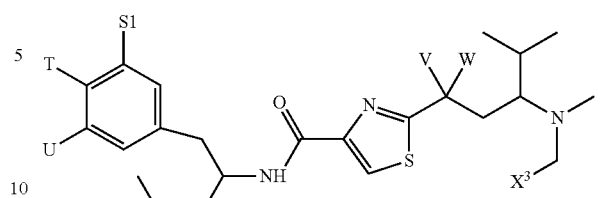

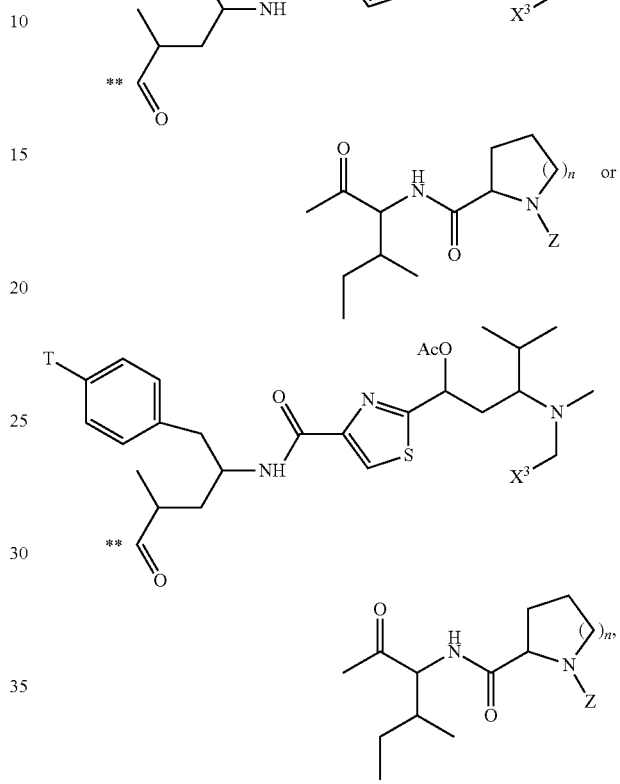

wherein ** represents the point of attachment of D to L; or a pharmaceutically acceptable salt thereof.

2. The drug delivery conjugate of claim wherein the bivalent linker further comprises a releasable linker that includes a disulfide, or a pharmaceutically acceptable salt thereof.

3. The drug delivery conjugate of claim wherein the bivalent linker further comprises a releasable linker that includes a carbonate, or a pharmaceutically acceptable salt thereof.

4. The drug delivery conjugate of claim wherein the bivalent linker further comprises a releasable linker that includes an acyl hydrazide, or a pharmaceutically acceptable salt thereof.

5. The drug delivery conjugate of claim wherein the bivalent linker further comprises one or more groups of the formula

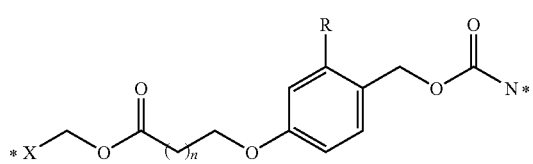

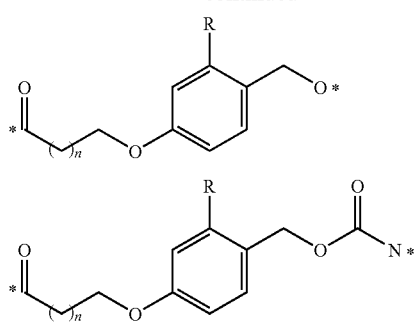

wherein X⁴ is a heteroatom, or a carbonyl group; n1 is an integer from 0 to 4; R is hydrogen or alkoxy; and * represents an open valence, or a pharmaceutically acceptable salt thereof.

6. The drug delivery conjugate of claim wherein the bivalent linker further comprises one or more groups of the formula

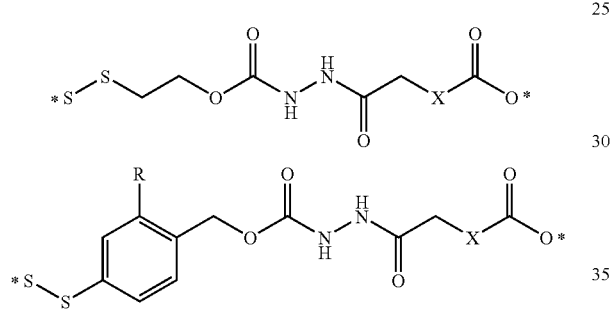

wherein X⁵ is NH, CH₂, or O; R is hydrogen or alkoxy; and * represents an open valence, or a pharmaceutically acceptable salt thereof.

7. The drug delivery conjugate of claim 1, wherein the bivalent linker further comprises one or more groups of the formula

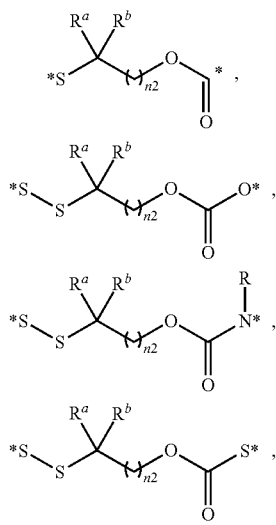

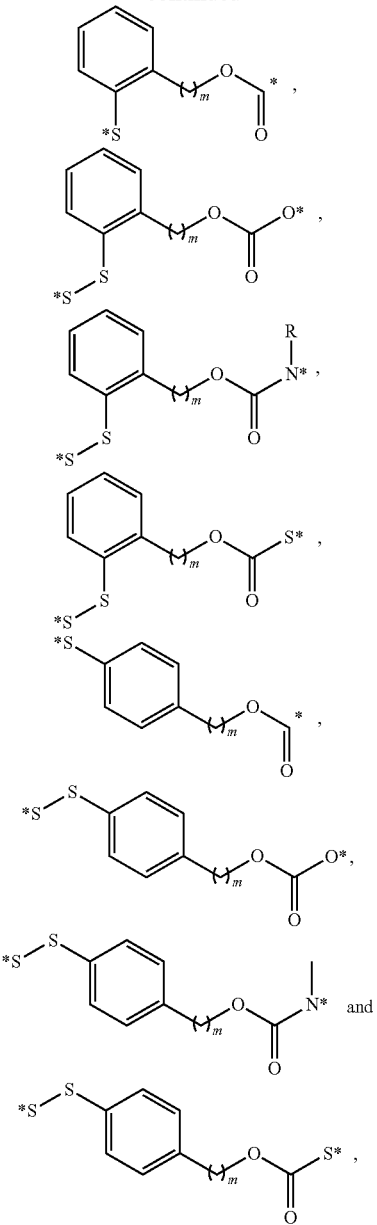

and wherein m and n2 are integers independently selected from 1 to 4; $R^a$ and $R^b$ are each independently selected from the group consisting of hydrogen and alkyl; or $R^a$ and $R^b$ are taken together with the attached carbon atom to form a carbocyclic ring; R is an optionally substituted alkyl group, an optionally substituted acyl group, or a nitrogen protecting group; and * represents an open valence, or a pharmaceutically acceptable salt thereof.

8. The drug delivery conjugate of claim 1, wherein the bivalent linker further comprises a peptide comprising from 2 to about 20 amino acids, or a pharmaceutically acceptable salt thereof.

9. The drug delivery conjugate of claim 1, wherein the bivalent linker further comprises a peptide comprising from 4 to about 8 amino acids, or a pharmaceutically acceptable salt thereof.

10. The drug delivery conjugate of claim 1, wherein the bivalent linker further comprises at least 2 amino acids selected from the group consisting of asparagine, aspartic acid, cysteine, glutamic acid, lysine, glutamine, arginine, serine, ornithine, and threonine, or a pharmaceutically acceptable salt thereof.

11. The drug delivery conjugate of claim 1, wherein the bivalent linker further comprises between 2 and about 5 amino acids selected from the group consisting of asparagine, aspartic acid, cysteine, glutamic acid, lysine, glutamine, arginine, serine, ornithine, and threonine, or a pharmaceutically acceptable salt thereof.

12. The drug delivery conjugate of claim 1, wherein the bivalent linker further comprises a tripeptide, tetrapeptide, pentapeptide, or hexapeptide consisting of amino acids selected from the group consisting of aspartic acid, cysteine, glutamic acid, lysine, arginine, and ornithine, and combinations thereof, or a pharmaceutically acceptable salt thereof.

13. The drug delivery conjugate of claim 1, wherein the bivalent linker further comprises a hydrophilic spacer linker, or a pharmaceutically acceptable salt thereof.

14. The drug delivery conjugate of claim 1, wherein the releasable linker includes a hydrophilic spacer linker of the formulae

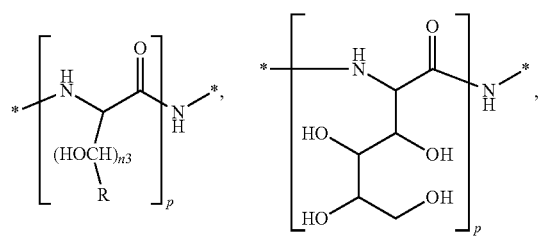

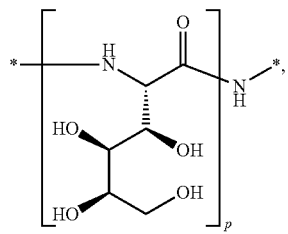

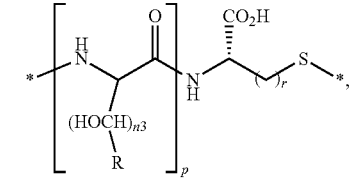

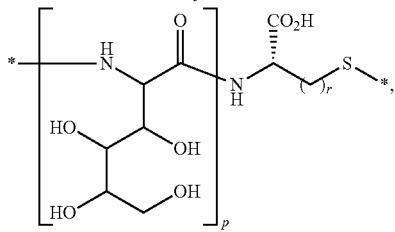

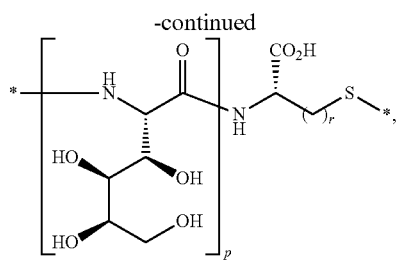

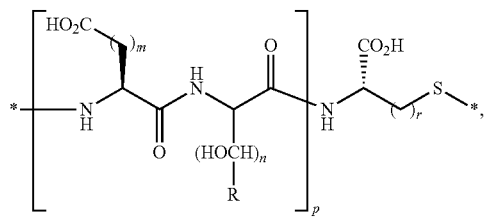

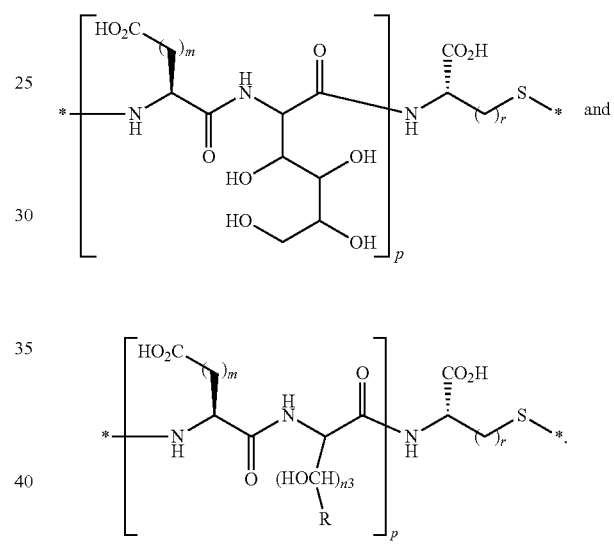

wherein R is H, alkyl, cycloalkyl, or arylalkyl; m is an integer from 1 to 3; n3 is an integer from 1 to 5, p is an integer from 1 to 5, and r is an integer from 1 to 3, wherein each * represents the point of attachment of one or more additional spacer linkers, one or more releasable linkers, D, or B; or a pharmaceutically acceptable salt thereof.

15. A pharmaceutical composition comprising a therapeutically effective amount of the drug delivery conjugate of claim 1, or a pharmaceutically acceptable salt thereof, and a pharmaceutically acceptable carrier, diluent, or excipient therefore, or a combination thereof.

* * * * *